(12) United States Patent
Khan et al.

(10) Patent No.: US 12,012,413 B2
(45) Date of Patent: Jun. 18, 2024

(54) METHODS OF TREATING PAINFUL DIABETIC PERIPHERAL NEUROPATHY

(71) Applicant: Tenacia Biotechnology (Hong Kong) Co., Limited, Sheung Wan (HK)

(72) Inventors: M. Amin Khan, Evanston, IL (US); Mohsen Arghavani, Lake in the Hills, IL (US); Phil Bauer, Highland Park, IL (US); Eduardo Mar, Northbrook, IL (US)

(73) Assignee: Tenacia Biotechnology (Hong Kong) Co., Limited, Hong Kong (HK)

( * ) Notice: Subject to any disclaimer, the term of this patent is extended or adjusted under 35 U.S.C. 154(b) by 120 days.

(21) Appl. No.: 17/094,584

(22) Filed: Nov. 10, 2020

(65) Prior Publication Data

US 2021/0139489 A1    May 13, 2021

Related U.S. Application Data

(60) Provisional application No. 62/933,622, filed on Nov. 11, 2019.

(51) Int. Cl.
| | |
|---|---|
| *C07D 487/10* | (2006.01) |
| *A61K 9/00* | (2006.01) |
| *A61K 9/20* | (2006.01) |
| *A61K 9/48* | (2006.01) |
| *A61P 25/02* | (2006.01) |

(52) U.S. Cl.
CPC .......... *C07D 487/10* (2013.01); *A61K 9/0053* (2013.01); *A61K 9/2013* (2013.01); *A61K 9/2054* (2013.01); *A61K 9/2059* (2013.01); *A61K 9/4858* (2013.01); *A61K 9/4866* (2013.01); *A61P 25/02* (2018.01); *C07B 2200/13* (2013.01)

(58) Field of Classification Search
None
See application file for complete search history.

(56) References Cited

U.S. PATENT DOCUMENTS

| | | |
|---|---|---|
| 4,904,681 A | 2/1990 | Cordi et al. |
| 4,959,493 A | 9/1990 | Ohfume et al. |
| 5,061,721 A | 10/1991 | Cordi et al. |

(Continued)

FOREIGN PATENT DOCUMENTS

| | | |
|---|---|---|
| CN | 101066945 A | 11/2007 |
| CN | 101125817 A | 2/2008 |

(Continued)

OTHER PUBLICATIONS

Genin et al . Design, synthesis and x-ray crystallographic analysis of two novel spirolactam systems as b-turn mimetics. J. Org. Chem. 1993, 58, 860-866. (Year: 1993).*

(Continued)

*Primary Examiner* — Lakshmi S Channavajjala
(74) *Attorney, Agent, or Firm* — Jun He Law Offices P.C.; James J. Zhu

(57) ABSTRACT

Provided herein are methods of treating painful diabetic peripheral neuropathy, such as advanced painful DPN, in a patient by administering to the patient an effective amount of NYX-2925 or a pharmaceutically acceptable salt thereof. Also provided are crystalline forms of 3-hydroxy-2-(5-isobutyryl-1-oxo-2,5-diazaspiro[3,4]octan-2-yl)butanamide.

7 Claims, 21 Drawing Sheets

(56) References Cited

U.S. PATENT DOCUMENTS

| | | |
|---|---|---|
| 5,086,072 A | 2/1992 | Trullas et al. |
| 5,166,136 A | 11/1992 | Ward et al. |
| 5,168,103 A | 12/1992 | Kinney et al. |
| 5,350,769 A | 9/1994 | Kasai et al. |
| 5,523,323 A | 6/1996 | Maccecchini |
| 5,605,911 A | 2/1997 | Olney et al. |
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,521,414 B2 | 2/2003 | Melcher et al. |
| 6,541,453 B2 | 4/2003 | Oldham et al. |
| 6,635,270 B2 | 10/2003 | Hong et al. |
| 6,667,317 B2 | 12/2003 | Chenard et al. |
| 6,821,985 B2 | 11/2004 | Chenard et al. |
| 6,828,318 B2 | 12/2004 | Snape et al. |
| 7,273,889 B2 | 9/2007 | Mermelstein et al. |
| 7,884,080 B2 | 2/2011 | Aslanian et al. |
| 8,097,634 B2 | 1/2012 | Ackermann et al. |
| 8,492,340 B2 | 7/2013 | Moskal |
| 9,504,670 B2 | 11/2016 | Lowe, III et al. |
| 9,512,133 B2 | 12/2016 | Khan et al. |
| 9,512,134 B2 | 12/2016 | Lowe, III et al. |
| 9,579,304 B2 | 2/2017 | Lowe, III et al. |
| 9,708,335 B2 | 7/2017 | Lowe, III et al. |
| 9,738,650 B2 | 8/2017 | Lowe, III et al. |
| 9,758,525 B2 | 9/2017 | Lowe, III et al. |
| 9,802,946 B2 | 10/2017 | Khan et al. |
| 9,828,384 B2 | 11/2017 | Lowe, III et al. |
| 9,925,169 B2 | 3/2018 | Khan |
| 9,932,347 B2 | 4/2018 | Khan |
| 10,052,308 B2 | 8/2018 | Lowe, III et al. |
| 10,150,769 B2 | 12/2018 | Khan |
| 10,195,179 B2 | 2/2019 | Khan |
| 10,196,401 B2 | 2/2019 | Khan |
| 10,253,032 B2 | 4/2019 | Lowe, III et al. |
| 10,273,239 B2 | 4/2019 | Lowe, III et al. |
| 10,316,041 B2 | 6/2019 | Lowe, III et al. |
| 10,441,571 B2 | 10/2019 | Lowe, III et al. |
| 10,441,572 B2 | 10/2019 | Lowe, III et al. |
| 10,906,913 B2 | 2/2021 | Khan et al. |
| 10,918,637 B2 | 2/2021 | Khan |
| 10,961,189 B2 | 3/2021 | Khan |
| 11,028,095 B2 | 6/2021 | Khan |
| 2002/0103335 A1 | 8/2002 | Oldham et al. |
| 2003/0022253 A1 | 1/2003 | Moskal |
| 2003/0064921 A1 | 4/2003 | Millhauser et al. |
| 2003/0175734 A1 | 9/2003 | Kroes et al. |
| 2005/0037433 A1 | 2/2005 | Nakanishi et al. |
| 2005/0118286 A1 | 6/2005 | Suffin et al. |
| 2006/0063707 A1 | 3/2006 | Baudry et al. |
| 2006/0241046 A1 | 10/2006 | Olivera et al. |
| 2007/0087404 A1 | 4/2007 | Stahl et al. |
| 2007/0208001 A1 | 9/2007 | Zhuo et al. |
| 2009/0221544 A1 | 9/2009 | Stein et al. |
| 2010/0102616 A1 | 4/2010 | Yamasaki et al. |
| 2011/0306586 A1 | 12/2011 | Khan et al. |
| 2012/0295852 A1 | 11/2012 | Moskal |
| 2013/0005662 A1 | 1/2013 | Moskal |
| 2013/0035292 A1 | 2/2013 | Moskal et al. |
| 2013/0053325 A1 | 2/2013 | Moskal et al. |
| 2013/0310323 A1 | 11/2013 | Moskal |
| 2013/0316954 A1 | 11/2013 | Moskal |
| 2014/0107037 A1 | 4/2014 | Moskal |
| 2015/0051262 A1 | 2/2015 | Khan et al. |
| 2015/0105364 A1 | 4/2015 | Khan et al. |
| 2015/0336969 A1 | 11/2015 | Khan et al. |
| 2015/0368252 A1 | 12/2015 | Lowe, III et al. |
| 2015/0368253 A1 | 12/2015 | Lowe, III et al. |
| 2015/0368254 A1 | 12/2015 | Lowe, III et al. |
| 2015/0376195 A1 | 12/2015 | Lowe, III et al. |
| 2016/0122359 A1 | 5/2016 | Lowe, III et al. |
| 2016/0289240 A1 | 10/2016 | Lowe, III et al. |
| 2016/0368926 A1 | 12/2016 | Lowe, III et al. |
| 2017/0231956 A1 | 8/2017 | Lowe et al. |
| 2017/0333395 A1 | 11/2017 | Khan |
| 2017/0334922 A1 | 11/2017 | Khan |
| 2018/0092879 A1 | 4/2018 | Khan |
| 2018/0093994 A1 | 4/2018 | Khan |
| 2018/0127430 A1 | 5/2018 | Lowe, III et al. |
| 2018/0155354 A1 | 6/2018 | Lowe, III et al. |
| 2018/0179217 A1 | 6/2018 | Lowe, III et al. |
| 2018/0179218 A1 | 6/2018 | Lowe, III et al. |
| 2018/0215767 A1 | 8/2018 | Lowe, III et al. |
| 2018/0244680 A1 | 8/2018 | Lowe, III et al. |
| 2018/0250267 A1 | 9/2018 | Lowe, III et al. |
| 2018/0250268 A1 | 9/2018 | Lowe, III et al. |
| 2018/0291023 A1 | 10/2018 | Khan |
| 2019/0077807 A1 | 3/2019 | Khan et al. |
| 2019/0161442 A1 | 5/2019 | Khan |
| 2019/0175588 A1 | 6/2019 | Khan |
| 2019/0177334 A1 | 6/2019 | Khan |
| 2019/0194200 A1 | 6/2019 | Khan |
| 2019/0330209 A1 | 10/2019 | Khan |
| 2020/0181159 A1 | 6/2020 | Khan |
| 2020/0206189 A1 | 7/2020 | Lowe, III et al. |
| 2021/0002279 A1 | 1/2021 | Khan |
| 2021/0040095 A1 | 2/2021 | Khan |
| 2021/0047324 A1 | 2/2021 | Khan |
| 2021/0139489 A1 | 5/2021 | Madsen et al. |
| 2021/0155632 A1 | 5/2021 | Lowe, III et al. |

FOREIGN PATENT DOCUMENTS

| | | |
|---|---|---|
| CN | 103974712 A | 8/2014 |
| CN | 104321071 A | 1/2015 |
| EP | 0180398 A1 | 5/1986 |
| EP | 2542254 A1 | 1/2013 |
| EP | 2771021 A0 | 5/2013 |
| JP | 2013519683 A | 5/2013 |
| JP | 2014520072 A | 8/2014 |
| RU | 2039035 C1 | 7/1995 |
| WO | WO-1996/032105 A1 | 10/1996 |
| WO | WO-1997/043306 A1 | 11/1997 |
| WO | WO-1999/024584 A1 | 5/1999 |
| WO | WO-1999/051985 A1 | 10/1999 |
| WO | WO-2000/028090 A2 | 5/2000 |
| WO | WO-2001/36685 A2 | 5/2001 |
| WO | WO-2001/96606 A2 | 12/2001 |
| WO | WO-2001/98367 A2 | 12/2001 |
| WO | WO-2002/47535 A2 | 6/2002 |
| WO | WO-2002/072609 A2 | 9/2002 |
| WO | WO-2003/010540 A1 | 2/2003 |
| WO | WO-2004/005293 A2 | 1/2004 |
| WO | WO-2005/020973 A2 | 3/2005 |
| WO | WO-2005/035535 A1 | 4/2005 |
| WO | WO-2007/088041 A1 | 8/2007 |
| WO | WO-2007/103719 A2 | 9/2007 |
| WO | WO-2009/039390 A2 | 3/2009 |
| WO | WO-2009/105718 A1 | 8/2009 |
| WO | WO-2009/156369 A1 | 12/2009 |
| WO | WO-2009/156396 A1 | 12/2009 |
| WO | WO-2010/015545 A1 | 2/2010 |
| WO | WO-2010/018213 A2 | 2/2010 |
| WO | WO-2010/033757 A1 | 3/2010 |
| WO | WO-2010/065709 A2 | 6/2010 |
| WO | WO-2010/102616 A1 | 9/2010 |
| WO | WO-2011/003064 A2 | 1/2011 |
| WO | WO-2011/044089 A2 | 4/2011 |
| WO | WO-2011/100585 A1 | 8/2011 |
| WO | WO-2012/021712 A1 | 2/2012 |
| WO | WO-2012/149389 A2 | 11/2012 |
| WO | WO-2013/001448 A1 | 1/2013 |
| WO | WO-2013/014448 A1 | 1/2013 |
| WO | WO-2013/063120 A2 | 5/2013 |
| WO | WO-2014/011590 A2 | 1/2014 |

(56) References Cited

FOREIGN PATENT DOCUMENTS

| WO | WO-2014/120783 A1 | 8/2014 |
|----|-------------------|--------|
| WO | WO-2014/120784 A1 | 8/2014 |
| WO | WO-2014/120789 A1 | 8/2014 |
| WO | WO-2014/120800 A1 | 8/2014 |
| WO | WO-2014120786 A1 | 8/2014 |
| WO | WO-2017/201283 A1 | 11/2017 |
| WO | WO-2017/201285 A1 | 11/2017 |
| WO | WO-2018/026763 A1 | 2/2018 |
| WO | WO-2018/026779 A1 | 2/2018 |
| WO | WO-2018/026782 A1 | 2/2018 |
| WO | WO-2018/026792 A1 | 2/2018 |
| WO | WO-2018/026798 A1 | 2/2018 |

OTHER PUBLICATIONS

Alonso et al. Spiro b-lactams as b-turn mimetics, design, synthesis and NMR conforatioal analysis. J. org. chem. 2001, 66, 6333-6338 (Year: 2001).*

Rasenack et al. Crystal habit and tableting behavior. . International Journal of Pharmaceutics, 244, 45-57. (Year: 2002).*

Ghoreishi-Haack et al., NYX-2925 Is a Novel N-Methyl-d-Aspartate Receptor Modulator that Induces Rapid and Long-Lasting Analgesia in Rat Models of Neuropathic Pain, Neuropharmacology, Sep. 2018, 366 (3) 485-497. (Year: 2018).*

U.S. Appl. No. 13/051,237, NMDA Receptor Modulators, Abandoned, filed Mar. 18, 2011, US 2011-0306586 Published on Dec. 15, 2011.

U.S. Appl. No. 14/050,641, NMDA Receptor Modulators Uses Thereof, filed Oct. 10, 2013, Patented, U.S. Pat. No. 9,512,133 Issued Dec. 6, 2016.

U.S. Appl. No. 14/580,803, NMDA Receptor Modulators and Uses Thereof, filed Dec. 23, 2014, Patented, U.S. Pat. No. 9,802,946 Issued Oct. 31, 2017.

U.S. Appl. No. 15/785,603, NMDA Receptor Modulators Uses Thereof, filed Oct. 17, 2017, Patented, U.S. Pat. No. 10,906,913 Issued on Feb. 2, 2021.

U.S. Appl. No. 17/111,657, NMDA Receptor Modulators Uses, Pending, filed Dec. 4, 2020.

U.S. Appl. No. 16/006,125, Spiro-Lactam NMDA Modulators and Methods of Using Same, filed Jun. 12, 2018, Patented, U.S. Pat. No. 10,150,769 Issued on Dec. 11, 2018.

U.S. Appl. No. 16/197,584, Spiro-Lactam NMDA Methods of Using Same, filed Nov. 21, 2018, Abandoned, US 2019-0330209 Published on Oct. 31, 2019.

U.S. Appl. No. 16/322,604, Spiro-Lactam NMDA Modulators and Methods of Using Same, filed Feb. 1, 2019, Published, US 2019-0194200 Published on Jun. 27, 2019.

U.S. Appl. No. 16/781,141, Spiro-Lactam NMDA Modulators and Methods of Using Same, filed Feb. 4, 2020, Published, US 2021-0002279 Published on Jan. 7, 2021.

U.S. Appl. No. 14/764,395, Spiro-Lactam NMDA Receptor Modulators and Uses Thereof, filed Jul. 29, 2015, Patented, U.S. Pat. No. 9,512,134 Issued Dec. 6, 2016.

U.S. Appl. No. 14/932,579, Spiro-Lactam NMDA Receptor Modulators and Uses Thereof, filed Nov. 4, 2015, Patented, U.S. Pat. No. 9,504,670 Issued Nov. 29, 2016.

U.S. Appl. No. 15/049,577, Spiro-Lactam NMDA Receptor Modulators and Uses Thereof, filed Feb. 22, 2016, Patented, U.S. Pat. No. 9,579,304 Issued Feb. 28, 2017.

U.S. Appl. No. 15/337,605, Spiro-Lactam NMDA Receptor Modulators and Uses Thereof, filed Oct. 28, 2016, Patented, U.S. Pat. No. 10,052,308 Issued on Aug. 21, 2018.

U.S. Appl. No. 15/969,186, Spiro-Lactam NMDA Receptor Modulators and Uses Thereof, filed May 2, 2018, Patented, U.S. Pat. No. 10,441,571 Issued Oct. 15, 2019.

U.S. Appl. No. 15/969,200, Spiro-Lactam NMDA Receptor Modulators and Uses Thereof, filed May 2, 2018, Patented, U.S. Pat. No. 10,441,572 Issued Oct. 15, 2019.

U.S. Appl. No. 16/536,582, Spiro-Lactam NMDA Receptor Modulators and Uses Thereof, filed Aug. 9, 2019, Published, US 2020-0206189 Published on Jul. 2, 2020.

U.S. Appl. No. 14/764,402, Spiro-Lactam NMDA Receptor Modulators and Uses Thereof, filed Jul. 29, 2015, Patented, U.S. Pat. No. 9,828,384 Issued Nov. 28, 2017.

U.S. Appl. No. 15/671,409, Spiro-Lactam NMDA Receptor Modulators and Uses Thereof, filed Aug. 8, 2017, Abandoned, US 2018-0179218 Published on Jun. 28, 2018.

U.S. Appl. No. 15/938,040, Spiro-Lactam NMDA Receptor Modulators and Uses Thereof, filed Mar. 28, 2018, Abandoned, US 2018-0215767 Published on Aug. 2, 2018.

U.S. Appl. No. 15/968,976, Spiro-Lactam NMDA Receptor Modulators and Uses Thereof, filed May 2, 2018, Abandoned, US 2018-0244680 Published on Aug. 30, 2018.

U.S. Appl. No. 16/919,438, Spiro-Lactam NMDA Receptor Modulators and Uses Thereof, filed Jul. 2, 2020, Published, US 2021-0155632 Published on May 27, 2021.

U.S. Appl. No. 14/764,411, Spiro-Lactam NMDA Receptor Modulators and Uses Thereof, filed Jul. 29, 2015, Patented, U.S. Pat. No. 9,758,525 Issued Sep. 12, 2017.

U.S. Appl. No. 15/667,014, Spiro-Lactam NMDA Receptor Modulators and Uses Thereof, filed Aug. 2, 2017, Patented, U.S. Pat. No. 10,273,239 Issued Apr. 30, 2019.

U.S. Appl. No. 14/764,419, Spiro-Lactam NMDA Receptor Modulators and Uses Thereof, filed Jul. 29, 2015, Patented, U.S. Pat. No. 9,738,650 Issued Aug. 22, 2017.

U.S. Appl. No. 15/653,738, Spiro-Lactam NMDA Receptor Modulators and Uses Thereof, filed Jul. 19, 2017, Patented, U.S. Pat. No. 10,253,032 Issued Apr. 9, 2019.

U.S. Appl. No. 14/764,426, Spiro-Lactam NMDA Receptor Modulators and Uses Thereof, filed Jul. 29, 2015, Patented, U.S. Pat. No. 9,708,335 Issued Jul. 18, 2017.

U.S. Appl. No. 15/625,163, Spiro-Lactam NMDA Receptor Modulators and Uses Thereof, filed Jun. 16, 2017, Patented, U.S. Pat. No. 10,316,041 Issued Jun. 11, 2019.

U.S. Appl. No. 16/321,901, Spiro-Lactam NMDA Receptor Modulators and Uses Thereof, filed Jan. 30, 2019, Patented, U.S. Pat. No. 10,961,189 Issued on Mar. 30, 2021.

U.S. Appl. No. 17/177,336, Spiro-Lactam NMDA Receptor Modulators and Uses Thereof, filed Feb. 17, 2021, Pending.

U.S. Appl. No. 16/321,903, Spiro-Lactam NMDA Receptor Modulators and Uses Thereof, filed Jan. 30, 2019, Patented, U.S. Pat. No. 10,918,637 Issued on Feb. 16, 2021.

U.S. Appl. No. 17/108,199, Spiro-Lactam NMDA Receptor Modulators and Uses Thereof, filed Dec. 1, 2020, Pending.

U.S. Appl. No. 16/321,905, Spiro-Lactam NMDA Receptor Modulators and Uses Thereof, filed Jan. 30, 2019, Published, US 2019-0177334 Published on Jun. 13, 2019.

U.S. Appl. No. 16/505,947, Methods of Identifying Compounds for Treating Depression and Other Related Disease, filed Jul. 9, 2019, Abandoned.

U.S. Appl. No. 16/321,906, Spiro-Lactam and Bis-Spiro-Lactam NMDA Receptor Modulators and Uses Thereof, filed Jan. 30, 2019, Published, U.S. Pat. No. 11,028,095 Issued on Jun. 8, 2021.

U.S. Appl. No. 17/314,174, Spiro-Lactam and Bis-Spiro-Lactam NMDA Receptor Modulators and Uses Thereof, filed May 7, 2021, Pending.

U.S. Appl. No. 15/638,669, Spiro-Lactam NMDA Receptor Modulators and Uses Thereof, filed Jun. 30, 2017, Patented, U.S. Pat. No. 9,932,347 Issued Apr. 3, 2018.

U.S. Appl. No. 15/830,378, Spiro-Lactam NMDA Receptor Modulators and Uses Thereof, filed Dec. 4, 2017, Patented, U.S. Pat. No. 10,196,401 Issued on Feb. 5, 2019.

U.S. Appl. No. 16/225,538, Spiro-Lactam NMDA Receptor Modulators and Uses Thereof, filed Dec. 19, 2018, Abandoned.

U.S. Appl. No. 15/636,888, Spiro-Lactam NMDA Receptor Modulators and Uses Thereof, filed Jun. 29, 2017, Patented, U.S. Pat. No. 9,925,169 Issued Mar. 27, 2018.

U.S. Appl. No. 15/830,383, Spiro-Lactam NMDA Receptor Modulators and Uses Thereof, filed Dec. 4, 2017, Patented, U.S. Pat. No. 10,195,179 Issued on Feb. 5, 2019.

(56) References Cited

OTHER PUBLICATIONS

U.S. Appl. No. 16/966,176, Spiro-Lactam NMDA Receptor Modulators and Uses Thereof, filed Jul. 30, 2020, Published, US 2021-0047324 Published on Feb. 18, 2021.

U.S. Appl. No. 16/966,170, Spiro-Lactam NMDA Receptor Modulators and Uses Thereof, filed Jul. 30, 2020, Published, US 2021-0040095 Published on Feb. 11, 2021.

U.S. Appl. No. 17/094,595, Methods of Treating Fibromyalgia, filed Nov. 10, 2020, Pending.

U.S. Appl. No. 17/110,481, Methods of Treating Cognitive Impairment Associated with Neurodegenerative Disease, filed Dec. 3, 2020, Pending.

Abbott AV et al., 'The Formalin Test: Scoring Properties of the First and Second Phases of the Pain Response in Rats,' Pain, Jan. 1995 (Jan. 1995), 60(1):91-102.

Abramets, II, 'Neurophysiological and Neurochemical Aspects of the Effects of Antidepressants and Mood Stabilizers,' Neurophysiol, Jan. 2008 (Jan. 2008), 40(1):64-78.

Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.

Anonymous, Database Accession No. 1031928-30-9, Database Registry [Online] Chemical Abstracts Service, Columbus, Ohio, US; Jul. 1, 2008 (Jan. 7, 2008), XP002668992.

Anonymous, Database Accession No. 1053605-89-2, Database Registry [Online] Chemical Abstracts Service, Columbus, Ohio, US; Sep. 28, 2008 (Sep. 28, 2008), XP002668993.

Anonymous, NCBI Submission NM_000149, '*Homo Sapiens* Fucosyltransferase 3 (galactoside 3(4)-L-fucosyltransferase, Lewis Blood Group)(FUT3), Transcript Variant 1, mRNA,' 1990 (1990), Retrieved from the internet; «URL:http://www.ncbi.nlm.nih.gov/nuccore/148277008», pp. 1-5.

Anonymous, NCBI Submission NM_001276, '*Homo Sapiens* Chitinase 3-like 1 (cartilage glycoprotein-39)(CHI3L1), mRNA,' 1989 (1989), Retrieved from the internet; <URL:http://www.ncbi.nlm.nih.gov/nuccore/144226250>, pp. 1-5.

Anonymous, NCBI Submission NM_030979.1, '*Homo Sapiens* poly(A) Binding Protein, Cytoplasmic 3 (PABPC3), mRNA,' 2003 (2003), Retrieved from the internet; <URL:http://www.ncbi.nlm.nih.gov/nuccore/13569957>, p. 1.

Anonymous, NCBI Submission NM_173216, '*Homo Sapiens* ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Aptinyx Press Release, "Aptinyx Announces Results of Phase 2 Fibromyalgia Study of NYX-2925 Have Been Selected for Late-Breaking Presentation at the American College of Rheumatology Annual Meeting," dated Oct. 28, 2019, 2 pages.

Aptinyx Press Release, "Aptinyx Exploratory Clinical Studies Provide First Evidence that NYX-2925 Elicits Rapid, Persistent, NMDAr-Mediated Pharmacodynamic Activity in Humans," dated Nov. 12, 2018, 2 pages.

Aptinyx Press Release, "Aptinyx Initiates Two Phase 2 Studies of NYX-2925 in Patients with Chronic Centralized Pain Conditions," dated Nov. 12, 2019, 2 pages.

Aptinyx Press Release, "Aptinyx Reports Positive Data from Interim Analysis of Exploratory Study of NYX-2925 in Subjects with Fibromyalgia," dated Dec. 3, 2018, 2 pages.

Aptinyx Press Release, "Aptinyx Reports Top-line Results from Phase 2 Clinical Study of NYX-2925 in Painful Diabetic Peripheral Neuropathy," dated Jan. 16, 2019, 2 pages.

Aptinyx Press Release, "Robust Analgesic Activity of Aptinyx's NYX-2925 in Advanced DPN Patients Revealed Through Further Analysis of Data from Phase 2 Study," dated Apr. 18, 2019, 2 pages.

Bennett GJ and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.

Burch RM et al., 'GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), p. 1 (Poster #unknown).

Burgdorf JS et al., 'Neurobiology of 50-KHz Ultrasonic Vocalizations in Rats: Electrode, Lesion, and Pharmacology Studies,' Behav Brain Res, Mar. 19, 2007 (Mar. 19, 2007) (ePub), 182(2):274-83.

Burgdorf JS et al., 'The Antidepressant and Anxiolytic Properties of GLYX-13: A Novel NMDA Receptor Glycine Site Functional Partial Agonist,' ACNP 2010 Meeting, Dec. 6, 2010 (Dec. 6, 2010), p. 1 (Poster #198).

Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.

Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.

Burgdorf JS et al., 'Uncovering the Molecular Basis of Positive Affect Using Rough-and-Tumble Play in Rats: A Role for the NMDA Receptor and Implications for Depression,' Neuroscience, Jul. 14, 2010, (Jul. 14, 2010) (ePub), 168(3):769-77.

Burgdorf JS et al., 'Uncovering the Molecular Basis of Positive Affect Using Rough-and-Tumble Play in Rats: A Role for the NMDA Receptor and Implications for Depression,' Neuroscience 38th Annual Meeting, Washington DC, Nov. 17, 2008 (Nov. 17, 2008), pp. 1-2 (Poster #393.1/UU11) [Electronically available Sep. 2008].

Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4):174-80.

Coates C et al., 'Product Class 9: Beta-Lactams,' *Science of Synthesis*, Georg Thieme Verlag KG, Stuttgart, DE (Pub), 2000 (2000), 21:609-46.

Cremonesi G et al., 'Enantiomerically Pure Polyheterocyclic Spiro-beta-Lactams from trans-4-Hydroxy-L-proline,' J Org Chem, Mar. 19, 2010 (Mar. 19, 2010), 75(6):2010-7.

Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.

Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.

Del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.

Duman RS, 'Pathophysiology of Depression: The Concept of Synaptic Plasticity,' Eur Psychiatry, Jul. 2002 (Jul. 2002), 17(Suppl 3):306-10.

Erick M Carreira and Lisbet Kvaerno, Classics in Stereoselective Synthesis, (1st ed. 2009), Wiley-VCH Verlag GmbH & Co. KGaA, Weinham, DE (Publ), pp. 19-102 ISBN: 978-3-527-32452-1.

European Patent Office, Supplementary European Search Report (Form 1503) for EP 09 81 5233 (Fink D), completed at Munich DE on Feb. 8, 2012 (Feb. 8, 2012) pp. 1-3.

European Patent Office, Supplementary European Search Report (Form 1503) for EP 10 82 2514 (Fink D), completed at Munich DE on Feb. 1, 2013 (Feb. 1, 2013) pp. 1-2.

Export Data for 3 hydroxy 2 5 sulfonyl oxo2 5 diazaspiro, Apr. 22, 2016, Feb. 3, 2016, Jan. 30, 2016 and Mar. 26, 2015.

(56) References Cited

OTHER PUBLICATIONS

FDA mulls drug to slow late-stage Alzheimer's [online] retrieved from the internet; Sep. 24, 2003; URL: http://www.cnn.com/ 2003/HEALTH/conditions/09/24/alzheimers.drug.ap/index.html.

Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.

Foster AC and Fagg GE, 'Neurobiology: Taking Apart NMDA Receptors,' Nature, Oct. 1, 1987 (Oct. 1, 1987), 329(6138):395-6.

Golik U, 'Synthesis of Malonimide Derivatives as Potential Penicillin Analogs,' J Heterocycl Chem, Feb. 1972 (Feb. 1972), 9(1):21-4.

Golub et al, "Molecular Classification of Cancer: Class Discovery and Class Prediction by Gene Expression Monitoring," Science, 286:531-536, Oct. 15, 1999.

Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.

Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.

Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.

Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.

Haring R et al., 'Multiple Mode of Binding of Phencyclidines: High Affinity Association Between Phencyclidine Receptors in Rat Brain and A Monovalent Ion-Sensitive Polypeptide,' Biochem Biophys Res Commun, Jan. 30, 1987 (Jan. 30, 1987), 142(2):501-10.

Holderbach R et al., 'Enhanced Long-Term Synaptic Depression in an Animal Model of Depression,' Biol Psychiatry, Dec. 4, 2006 (Dec. 4, 2006) (ePub), 62(1):92-100.

Ikeda et al. Document No. 101:54757, retrieved from STN; entered in STN on Aug. 18, 1984.

International Searching Authority, International Search Report (ISA/210) for Application No. PCT/US08/77045, (Young LW), completed on Mar. 28, 2009 (Mar. 28, 2009) and dated Apr. 29, 2009 (Apr. 29, 2009), pp. 1-3.

International Searching Authority, International Search Report (ISA/210) for Application No. PCT/US09/57401, (Young LW), completed Dec. 6, 2009 (Dec. 12, 2009) and dated Dec. 24, 2009 (Dec. 24, 2009), pp. 1-2.

International Searching Authority, International Search Report (ISA/210) for Application No. PCT/US09/66536, (Kang YJ), completed Aug. 9, 2010 (Aug. 9, 2010) and dated Aug. 9, 2010 (Aug. 9, 2010), pp. 1-5.

International Searching Authority, International Search Report (ISA/210) for Application No. PCT/US2014/013619, (Wolf C), completed Mar. 6, 2014 (Mar. 6, 2014) and dated Mar. 20, 2014 (Mar. 20, 2014), pp. 1-3.

International Searching Authority, International Search Report (ISA/210) for Application No. PCT/US2014/013621, (Wolf C), completed Feb. 27, 2014 (Feb. 27, 2014) and dated Mar. 13, 2014 (Mar. 13, 2014), pp. 1-2.

International Searching Authority, International Search Report (ISA/210) for Application No. PCT/US2014/013623, (Wolf C), completed Mar. 3, 2014 (Mar. 3, 2014) and dated Mar. 13, 2014 (Mar. 13, 2014), pp. 1-3.

International Searching Authority, International Search Report (ISA/210) for Application No. PCT/US2014/013626, (Rudolf M), completed Mar. 10, 2014 (Mar. 10, 2014) and dated Mar. 18, 2014 (Mar. 18, 2014), pp. 1-4.

International Searching Authority, International Search Report (ISA/210) for Application No. PCT/US2014/013639, (Wolf C), completed Feb. 28, 2014 (Feb. 28, 2014) and dated Mar. 13, 2014 (Mar. 13, 2014), pp. 1-3.

International Searching Authority, Written Opinion of Application No. PCT/US2008/077045 (ISA/237), (Young LW), completed Mar. 28, 2009 (Mar. 28, 2009) and dated Mar. 24, 2010 (Mar. 24, 2010), pp. 1-8.

International Searching Authority, Written Opinion of Application No. PCT/US2009/057401 (ISA/237), (Young LW), completed Dec. 6, 2009 (Dec. 6, 2009) and dated Mar. 22, 2011 (Mar. 22, 2011), pp. 1-6.

International Searching Authority, Written Opinion of Application No. PCT/US2009/066536 (ISA/237), (Kang YJ), completed Aug. 9, 2010 (Aug. 9, 2010) and dated Jun. 7, 2011 (Jun. 7, 2011), pp. 1-8.

International Searching Authority, Written Opinion of Application No. PCT/US2014/013619 (ISA/237), (Wolf C), completed Mar. 6, 2014 (Mar. 6, 2014) and dated Aug. 4, 2015 (Aug. 4, 2015), pp. 1-4.

International Searching Authority, Written Opinion of Application No. PCT/US2014/013621 (ISA/237), (Wolf C), completed Feb. 27, 2014 (Feb. 27, 2014) and dated Aug. 4, 2015 (Aug. 4, 2015), pp. 1-6.

International Searching Authority, Written Opinion of Application No. PCT/US2014/013623 (ISA/237), (Wolf C), completed Mar. 3, 2014 (Mar. 3, 2014) and dated Aug. 4, 2015 (Aug. 4, 2015), pp. 1-4.

International Searching Authority, Written Opinion of Application No. PCT/US2014/013626 (ISA/237), (Rudolf M, completed Mar. 10, 2014 (Mar. 10, 2014) and dated Aug. 4, 2015 (Aug. 4, 2015), pp. 1-6.

International Searching Authority, Written Opinion of Application No. PCT/US2014/013639 (ISA/237), (Wolf C), completed Feb. 28, 2014 (Feb. 28, 2014) and dated Aug. 4, 2015 (Aug. 4, 2015), pp. 1-4.

Johnson JA et al., 'The Preparation of a Double Metallahelicate Containing 28 Copper Atoms,' Angew Chem Int Ed Engl, Feb. 3, 2003 (Feb. 3, 2003), 42(5):546-9.

Johnson KM and Jones SM, 'Neuropharmacolgy of Phencyclidine: Basic Mechanisms and Therapeutic Potential,' Annu Rev Pharmacol Toxicol, 1990 (1990), 30:707-50.

Khasanov AB et al., 'Novel Asymmetric Approach to Proline-Derived Spiro-beta-Lactams,' J Org Chem., Aug. 20, 2004 (Aug. 20, 2004), 69(17):5766-9.

Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.

Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.

Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.

Kroes RA et al., 'Development of a Novel Glycobiologic Therapy for Glioblastoma,' Neuro-oncol, Oct. 2006 (Oct. 2006), 8(4):397-8, (Abstract #CB-14).

Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).

Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep.-Oct. 1999), 7(3):125-43.

Lala et al., "Role of nitric oxide in tumor progression: Lessons from experimental tumors," Cancer and Metastasis Reviews, 17:91-106, 1998.

Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).

(56) References Cited

OTHER PUBLICATIONS

Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.
Liu et al. Document No. 120:244445, retrieved from STN; entered in STN on May 14, 1994.
Lynch G et al., 'Synaptic Pasticity in Early Aging,' Ageing Res Rev, Aug. 28, 2006 (Aug. 28, 2006) (ePub), 5(3):255-80.
Macias A et al., 'Diastereoselective [2+2]-Cycloaddition Reactions of Unsymmetrical Cyclic Ketenes with Imines: Synthesis of Modified Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.
Macias A et al., 'Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands,' Tetrahedron Lett, Jun. 2004 (Jun. 2004), 45(24):4657-60.
Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.
Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.
McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.
McMaster et al. Document No. 157:133191, retrieved from STN; entered in STN on Jun. 3, 2012.
Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.
Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.
Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).
Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.
Moskal JR et al., 'A Novel Approach to Unlocking the Therapeutic Potential of the NMDA Receptor,' Vital Signs e-Magazine, Sep. 2010 (Sep. 2010), pp. 1-2.
Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.
Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.
Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).
Myers SM and Johnson CP, 'Management of Children with Autism Spectrum Disorders,' Pediatrics, Oct. 29, 2007 (Oct. 29, 2007) (ePub), 120(5):1162-82.
Nagamori et al. Document No. 163:374386, retrieved from STN; entered in STN on Aug. 27, 2015.
Narahashi T et al., 'Mechanisms of Action of Cognitive Enhancers on Neuroreceptors,' Biol Pharm Bull, Nov. 2004 (Nov. 2004), 27(11):1701-6.
Newcomer et al. "NMDA receptor function, memory, and brain aging," Dialogues in Clinical Neuroscience, 2(3):219-232 (2000).
Overman LE and Osawa T, 'A Convenient Synthesis of 4-Unsubstituted beta-Lactams,' J Am Chem Soc, Mar. 1985 (Mar. 1985), 107(6):1698-701.
Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.
Patani et al., "Bioisosterism: A Rational Approach in Drug Design," Chem. Rev., Jan. 1, 1997, 96(8):3147-3176.
Pittenger C et al., 'The NMDA Receptor as a Therapeutic Target in Major Depressive Disorder,' CNS Neurol Disord Targets, Apr. 2007 (Apr. 2007), 6(2):101-15.
Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.
Ransom RW and Stec NL, 'Cooperative Modulation of [3H]MK-801 Binding to the N-Methyl-d-Asparate Receptor-Ion Channel Complex by I-Glumate, Glycine, and Polyamines,' J Neurochem, Sep. 1988 (Sep. 1988), 51(3):830-6.
Rasmusson GH et al., '6-Substituted Penicillin Derivatives,' Tetrahedron Lett, 1973 (1973), 14(2):145-8.
Rautio J et al., 'Prodrugs: Design and Clinical Applications,' Nat Rev Drug Discov, Mar. 2008 (Mar. 2008), 7(3):255-70.
Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.
Shankar GM and Walsh DM, 'Alzheimer's Disease: Synaptic Dysfunction and A-beta,' Mol Neurodegener, Nov. 23, 2009 (Nov. 23, 2009), 4:48-61.
Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.
Simplício Al et a;. , 'Prodrugs for Amines,' Molecules, Mar. 2008 (Mar. 2008), 13(3):519-47.
Singapore Search Report and Written Opinion Issued for corresponding Singapore application No. 11201505860X, dated Apr. 18, 2016.
Singapore Search Report and Written Opinion Issued for corresponding Singapore application No. 11201505862T, dated Apr. 18, 2016.
Singapore Search Report and Written Opinion Issued for corresponding Singapore application No. 11201505934X, dated Apr. 27, 2016.
Singapore Search Report and Written Opinion Issued for corresponding Singapore application No. 11201505937S, dated May 5, 2016.
Singapore Search Report and Written Opinion Issued for corresponding Singapore application No. 11201505942Y, dated Mar. 22, 2016.
Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.
Stanton PK et al., Neuroprotection by a Novel NMDAR Functional Glycine Site Partial Agonist, GLYX-13,' Neuroreport, Aug. 26, 2009 (Aug. 26, 2009), 20(13):1193-7.
Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.
Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.

(56) References Cited

OTHER PUBLICATIONS

Turturro A et al., 'Growth Curves and Survival Characteristics of the Animals Used in the Biomarkers of Aging Program,' J Gerentol A Biol Sci Med Sci, Nov. 1999 (Nov. 1999), 54A(11): B492-B501.
Various, *The NMDA Receptor*, (2nd ed. 1994), GL Collingridge and JC Watkins Eds., Oxford University Press, Inc., New York, New York US (Publ), pp. 1-479 ISBN: 0-19-262371-0.
Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10):1061-3.
Wood PL, 'The NMDA Receptor Complex: A Long and Winding Road to Therapeutics,' IDrugs, Mar. 2005 (Mar. 2005), 8(3):229-35.
Wood SG et al., 'Tetrapeptide Inhibitors of the IgA1 Proteinases from Type I Neisseria gonorrhoeae,' J Med Chem, Oct. 1989 (Oct. 1989), 32(10):2407-11.
Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.

\* cited by examiner

Difference versus PBO at Week 4

| Dose | Delta | P-value |
|---|---|---|
| 10mg | -0.38 | 0.35 |
| 50mg | -0.58 | 0.13 |
| 200mg | -0.52 | 0.20 |

FIG. 14

| Endpoint | Week 4 Change vs. Baseline | | Diff. | P-value |
|---|---|---|---|---|
| | 50mg (n=26) | PBO (n=33) | | |
| SF-MPQ – Total pain score | -2.00 | -1.46 | -0.54 | 0.236[1] |
| Insomnia Severity | -5.11 | -2.68 | -2.42 | 0.085[2] |
| BPI-DN (pain severity) | -2.02 | -0.97 | -1.05 | 0.036 |
| BPI-DN (pain interference) | -1.27 | -1.03 | -0.24 | 0.665 |
| QOL-DN (total)[3] | -8.24 | -5.08 | -3.16 | 0.397 |
| PGI-C[4] | 42.3% improved | 21.2% improved | 21.1% | 0.081 |

[1] Sig. separation on Neuropathic Descriptors subset (p=0.029)
[2] Insomnia severity was stat. sig better than PBO at week 2 (p=0.005)
[3] QOL scores were relatively low at baseline – ~30-35 out of possible 136 (lower scores represent better quality of life)
[4] PGI-C: improved includes patients who are "much improved" or "very much improved"

METHODS OF TREATING PAINFUL DIABETIC PERIPHERAL NEUROPATHY

This application claims priority to and the benefit of U.S. Provisional Patent Application No. 62/933,622, filed on Nov. 11, 2019; the contents of which are hereby incorporated by reference herein in their entirety.

BACKGROUND

Glutamate is the major excitatory neurotransmitter in the central nervous system and acts through activation of glutamate receptors. A portion of the receptors bind preferentially to N-methyl-D-aspartate (NMDA), and are therefore, termed NMDARs. Unlike other glutamate receptors found in the brain, such as α-amino-3-hydroxy-5-methyl-4-isoxazolepropionic acid or kainic acid receptors, the NMDARs are unique in that they have distinct binding sites for both glutamate and glycine, and binding by both ligands is required for receptor activation. The NMDARs are implicated in a number of physiological and pathological processes, including anxiety, cognition, learning, stroke, schizophrenia, Parkinson's disease, and neuropathic pain.

The central nervous system modulates the experience of pain in people with neuropathic pain, with the rostroventral medial medulla, the dorsal anterior cingulate cortex, the insula and other brain regions all thought to be involved.

Neuropathic pain is caused by disease or injury that affects the somatosensory system. Neuropathic pain occurs in conditions of persistent activation of pain mediators, resulting in changes to pain processing pathways in the brain. While neuropathic pain can initially arise within the central or the peripheral nervous system through a wide range of etiologies, central nervous system modulation of the experience of pain is common, regardless of the specific precipitating factors or initial location of the pain.

The prevalence of neuropathic pain is approximately 8% in the population in the United States. Individuals suffering from neuropathic pain, irrespective of the underlying disorder, currently have limited treatment options available. Current treatment options predominantly include antidepressants and antiepileptics. These therapies have shown some efficacy in treating neuropathic pain symptoms, although for a large proportion of patients, treatment is insufficient. Diabetic peripheral neuropathy (DPN) is one example of neuropathic pain.

A need continues to exist in the art for novel and more specific and/or potent compounds that are capable of treating neuropathic pain and, in particular, painful DPN such as advanced painful DPN.

SUMMARY

In one aspect, provided herein are methods of treating painful diabetic peripheral neuropathy (DPN), such as advanced painful DPN, in a patient in need thereof, comprising administering to the patient a therapeutically effective amount of (2S,3R)-3-hydroxy-2-((R)-5-isobutyryl-1-oxo-2,5-diazaspiro[3.4]octan-2-yl)butanamide ("NYX-2925"), or a pharmaceutically acceptable salt thereof. In some embodiments, administering is administering orally. In some embodiments, administering is administering once daily. In certain embodiments, the therapeutically effective amount is between about 10 mg to about 200 mg NYX-2925, or a pharmaceutically acceptable salt thereof.

In another aspect, provided herein are anhydrous and monohydrate crystalline forms of 3-hydroxy-2-(5-isobutyryl-1-oxo-2,5-diazaspiro[3.4]octan-2-yl)butanamide. For example, provided herein is a monohydrate crystalline form of NYX-2925 characterized by a powder X-ray diffraction pattern comprising characteristic peaks in degrees 2θ at about 10.8, 13.4, and 18.4.

BRIEF DESCRIPTION OF FIGURES

FIG. 14 is a table of other secondary endpoints for patients administered NYX-2925 vs. placebo for patients with advanced DPN (patients who have had DPN for ≥4 years).

DETAILED DESCRIPTION

Figure 1:
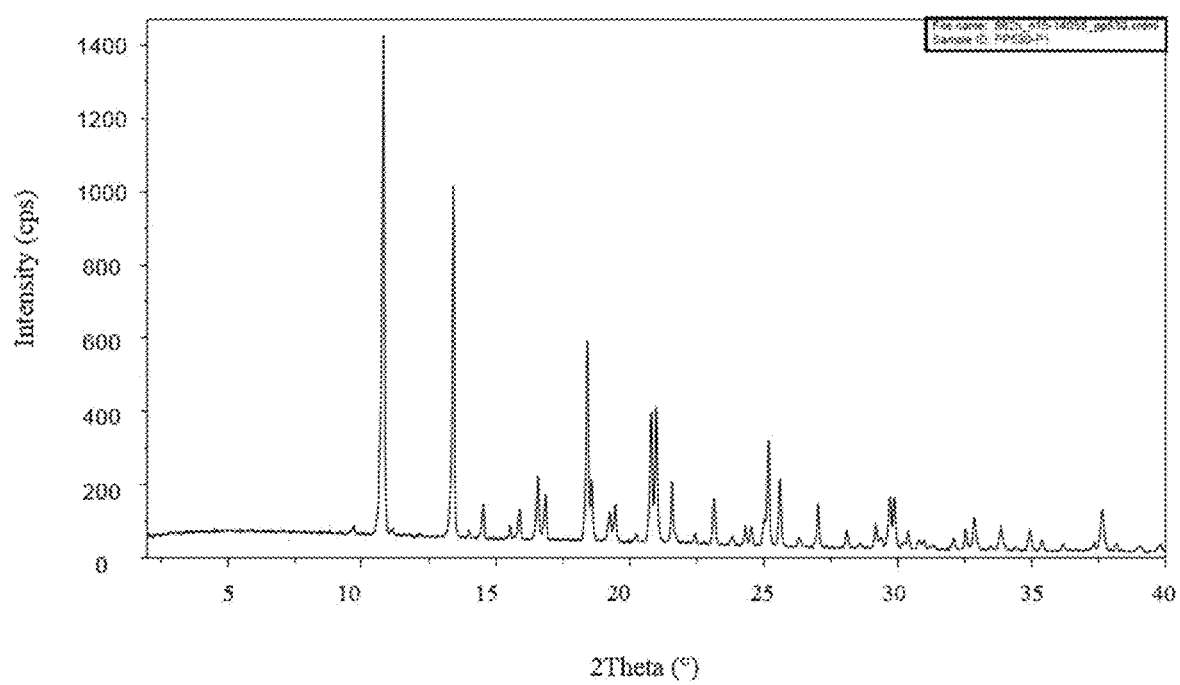
FIG. 1 depicts the X-ray powder diffraction (XRPD) pattern of Form MH of NYX-2925.

As generally described herein, the present disclosure provides methods of treating painful diabetic peripheral neuropathy ("DPN"), including advanced painful DPN, using a compound of the disclosure, namely, (2S,3R)-3-hydroxy-2-((R)-5-isobutyryl-1-oxo-2,5-diazaspiro[3.4]octan-2-yl)butanamide ("NYX-2925"), or a pharmaceutically acceptable salt thereof.

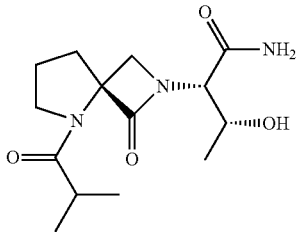

NYX-2925

NYX-2925 is an N-methyl-D-aspartate receptor (NMDAR) modulator, and at low concentrations of endogenous agonist (glycine or D-serine) and in the presence of glutamate, NYX-2925 partially activates the NMDAR. NYX-2925 appears to act at a binding site that is distinct from NMDAR agonists or antagonists studied to date, such as D-cycloserine, ketamine, MK-801, or kynurenic acid. The mode of action of NYX-2925 seems to be distinct from that of all existing and emerging drugs that are indicated for the treatment of neuropathic pain. While current medications target individual elements of pain signal transmission or modulation, NYX-2925 can modulate multiple synaptic relays within pain circuits.

The present disclosure also provides anhydrous and monohydrate crystalline forms of 3-hydroxy-2-(5-isobutyryl-1-oxo-2,5-diazaspiro[3.4]octan-2-yl)butanamide. For example, provided herein is a drug substance comprising at least a detectable amount of a disclosed crystalline form of (2S,3R)-3-hydroxy-2-((R)-5-isobutyryl-1-oxo-2,5-diaz-aspiro[3.4]octan-2-yl)butanamide. Also provided herein is a drug substance comprising a substantially pure crystalline form of NYX-2925. The disclosure also provides for a pharmaceutical formulation comprising a disclosed crystalline form of 3-hydroxy-2-(5-isobutyryl-1-oxo-2,5-diaz-aspiro[3.4]octan-2-yl)butanamide acid; and a pharmaceutically acceptable excipient.

Definitions

To facilitate an understanding of the present invention, a number of terms and phrases are defined below.

Unless defined otherwise, all technical and scientific terms used herein have the same meaning as commonly understood by one of ordinary skill in the art to which this invention belongs. The abbreviations used herein have their conventional meaning within the chemical and biological arts. The chemical structures and formulae set forth herein are constructed according to the standard rules of chemical valency known in the chemical arts.

Throughout the description, where formulations and kits are described as having, including, or comprising specific components, or where processes and methods are described as having, including, or comprising specific steps, it is contemplated that, additionally, there are formulation sand kits of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a formulation or a method described herein can be combined in a variety of ways without departing from the spirit and scope of the present invention, whether explicit or implicit herein. For example, where reference is made to a particular compound, that compound can be used in various embodiments of formulations of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, formulations specifying a percentage are by weight unless otherwise specified. Further, if a variable is not accompanied by a definition, then the previous definition of the variable controls.

As used herein, "pharmaceutical composition" or "pharmaceutical formulation" refers to the combination of a therapeutically active agent with a pharmaceutically acceptable excipient, making the composition especially suitable for diagnostic or therapeutic use in vivo or ex vivo.

"Pharmaceutically acceptable" refers to compounds, molecular entities, compositions, materials and/or dosage forms that do not produce an adverse, allergic or other untoward reaction when administered to an animal, or a human, as appropriate, and/or that are approved or approvable by a regulatory agency of the federal or a state government or the corresponding agency in countries other than the United States, or that is listed in the U.S. Pharmacopoeia or other generally recognized pharmacopoeia for use in animals, and more particularly, in humans.

As used herein, "pharmaceutically acceptable salt" refers to any salt of an acidic or a basic group that is present in a compound of the present invention (e.g., NYX-2925), which salt is compatible with pharmaceutical administration.

As is known to those of skill in the art, "salts" of compounds may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid.

Other acids, such as oxalic, while not in themselves pharmaceutically acceptable, may be employed in the preparation of salts useful as intermediates in obtaining the compounds described herein and their pharmaceutically acceptable acid addition salts.

Examples of bases include, but are not limited to, alkali metal (e.g., sodium and potassium) hydroxides, alkaline earth metal (e.g., magnesium and calcium) hydroxides, ammonia, and compounds of formula $NW_4^+$, wherein W is $C_{1-4}$ alkyl, and the like.

Examples of salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $K^+$, $Ca^{2+}$, $NH_4^+$, and $NW_4^+$ (where W can be a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, "pharmaceutically acceptable excipient" refers to a substance that aids the administration of an active agent to and/or absorption by a subject and can be included in the compositions or formulations of the present invention without causing a significant adverse toxicological effect on the patient. Non-limiting examples of pharmaceutically acceptable excipients include water, NaCl, normal saline solutions, such as a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. For examples of excipients, see Martin, Remington's Pharmaceutical Sciences, 15th Ed., Mack Publ. Co., Easton, PA (1975).

The term "AUC" refers to the area under the time/plasma concentration curve after administration of the pharmaceutical formulation. $AUC_{0\text{-}infinity}$ denotes the area under the plasma concentration versus time curve from time 0 to infinity; $AUC_{0\text{-}t}$ denotes the area under the plasma concentration versus time curve from time 0 to time t. It should be appreciated that AUC values can be determined by known methods in the art.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

The term "$C_{max}$" refers to the maximum concentration of a therapeutic agent (e.g., NYX-2925) in the blood (e.g., plasma) following administration of the pharmaceutical formulation.

The term "$t_{max}$" refers to the time in hours when $C_{max}$ is achieved following administration of the pharmaceutical formulation comprising a therapeutic agent (e.g., NYX-2925).

As used herein, "solid dosage form" means a pharmaceutical dose(s) in solid form, e.g., tablets, capsules, granules, powders, sachets, reconstitutable powders, dry powder inhalers and chewables.

By "co-administer" it is meant that a formulation described herein is administered at the same time, just prior to, or just after the administration of one or more additional therapies (e.g., analgesic, anti-cancer agent, chemotherapeutic, or treatment for a neurodegenerative disease). NYX-2925, or a pharmaceutically acceptable salt thereof, can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The terms "disease," "disorder," and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (e.g., "therapeutic treatment").

In general, an "effective amount" or "therapeutically effective amount" of a compound or a pharmaceutical formulation refers to an amount sufficient to elicit the desired biological response, e.g., to treat painful DPN. As will be appreciated by those of ordinary skill in this art, the effective amount of a compound of the disclosure may vary depending on such factors as the desired biological endpoint, the pharmacokinetics of the compound, the disease being treated, the mode of administration, and the age, weight, health, and condition of the subject.

As used herein, "PBO" is placebo.

As used herein, "MMRM" is mixed-effect model repeated measure.

As used herein, "NRS Score" for assessing pain assesses average pain intensity. The score is based on an 11 point numerical rating scale (NRS)/Likert scale ranging from 0 to 10, where 0 represents no pain and 10 is the worst pain imaginable.

As used herein, The "Michigan Neuropathy Screening Instrument" ("MNSI") is a 15-item, self-administered questionnaire and a lower extremity examination that includes inspection of vibratory sensation and ankle reflexes. It can be used to assess distal symmetrical peripheral neuropathy in diabetes. The history portion of the Michigan Neuropathy Screening Instrument answered by the subjects contains 15 questions with each question having a yes or no response. Each yes response has a numeric value of 1, and 0 is assigned to no responses. The History Total Score is the sum of all 15 questions with values ranging from 0 to 15. No missing values were imputed. The physical assessment portion of the Michigan Neuropathy Screening Instrument was completed by a study site health professional and was assessed individually for the right and left feet. Each foot has the following assessment with following numeric scores:

Appearance of Feet—Normal: Yes=0; No=1
Ulceration: Absent=0; Present=1
Ankle Reflexes: Present=0; Present/Reinforcement=0.5; Absent=1
Vibration Perception at Great Toe: Present=0; Decreased=0.5; Absent=1
Monofilament: Normal=0; Reduced=0.5; Absent=1

A subscale score was determined for both the right and left feet individually. The subscale scores ranged from 0 to 5 and no missing values were imputed. The Physical Assessment Total Score was the sum of both the right and left subscale scores if they were both calculated. Other details were collected if the appearance of the foot was not normal: deformities; dry skin, callus; infection; fissure; and other specified. That data collected was presented in subject listings, but was not part of the numeric subscale and total scores.

Both the Michigan Neuropathy Screening Instrument History Total Score and Physical Assessment Total Score were summarized using descriptive statistics in a table.

As used herein, "PGI-C" is patient global impression of change. PGI-C is a 7 point Likert scale that allows subjects to rate the change in the disease state from study initiation to specific time points during the study or at the end of the study. It provides the subject's impression of overall change since beginning the study. Below are the numeric values assigned in the 7-point scale along with categorical values and analysis categorical values:

| Numeric Value | Categorical Value | Analysis Categorical Value |
|---|---|---|
| 1 | Very Much Improved | Improved |
| 2 | Much Improved | Improved |
| 3 | Minimally Improved | Minimally Improved to Worse |
| 4 | No Change Minimally | Improved to Worse |
| 5 | Minimally Worse | Minimally Improved to Worse |
| 6 | Much Worse | Minimally Improved to Worse |
| 7 | Very Much Worse | Minimally Improved to Worse |
| Missing | Missing | Minimally Improved to Worse |

As used herein, "SF-MPQ-2" is short-form McGill pain questionnaire, version 2. The SF-MPQ-2 measures the sensory, affective, and evaluative qualities of pain, including symptoms relevant to neuropathic pain. The tool includes visual analogue as well as verbal rating scales of pain intensity on a total of 22 neuropathic and non-neuropathic pain descriptors that are each evaluated on a 10-point numerical rating scale/Likert scale ranging from 0 to 10. Where 0 represents none and 10 is worst possible.

The following questions that make up each published summary scale score:

Continuous Descriptors:
Throbbing Pain, Cramping Pain, Gnawing Pain, Aching Pain, Heavy Pain, and Tender Intermittent Descriptors:
Shooting Pain, Stabbing Pain, Sharp Pain, Splitting Pain, Electric-Shock Pain, and Piercing Neuropathic Descriptors:
Hot-Burning Pain, Cold-Freezing Pain, Pain Caused by Light Touch, Itching, Tingling or 'Pins and Needles', and Numbness Affective Descriptors:
Tiring-Exhausting, Sickening, Fearful, and Punishing-Cruel As used herein, "QOL-DN" is Norfolk quality of life Questionnaire-diabetic neuropathy. The Norfolk QOL-DN is a 47-item, subject-reported questionnaire designed to measure the relationship between symptomatic diabetic neuropathy and quality of life from the perspective of the patient. It is composed of 2 parts: questions related to symptoms experienced by the subject and questions related to the impact of the subject's neuropathy on activities of daily life. As a comprehensive questionnaire it addresses the entire spectrum of neuropathy including the concentration of symptoms in the extremities, subtle loss of function such as fine motor impairments and sensory changes, unique problems with proprioception and balance, and autonomic symptoms that are not captured in existing instruments. An initial biographical page collects twelve health related background history items, which are not scored. These are followed by 35 scored questions—numbered items comprising the entire scale. Lower scores represent a better quality of life.

As used herein, "insomnia severity index" (ISI) is a 7-item self-report questionnaire assessing the nature, severity, and impact of insomnia. The usual recall period is the "last month" and the dimensions evaluated are: severity of sleep onset, sleep maintenance and early morning awakening problems, sleep dissatisfaction, interference of sleep difficulties with daytime functioning, noticeability of sleep problems by others, and distress caused by the sleep difficulties. A 5-point Likert scale is used to rate each item (i.e. 0=none; 4=very severe).

As used herein, "BPI-DN" is brief pain inventory for diabetic peripheral neuropathy. The BPI is a patient-completed numeric rating scale that assesses the severity of pain (Severity scale), its impact on daily functioning (Interference scale), and other aspects of pain (e.g., location of pain, relief from medications). A modified version of the BPI, including the 4-item pain Severity scale (Worst Pain, Least Pain, Average Pain, and Pain Now) and the 7-item pain Interference scale (General Activity, Mood, Walking Ability, Normal Work, Relations with Others, Sleep, Enjoyment of Life) has been validated in patients with painful diabetic peripheral neuropathy, which distinguishes between pain due to DPN and pain due to other causes. Each BPI item uses a 0 to 10 numeric rating scale anchored at zero for "no pain" and 10 for "pain as bad as you can imagine" for Severity, and "does not interfere" to "completely interferes" for Interference.

Crystalline Forms

The present disclosure provides a monohydrate crystalline form of (2S,3R)-3-hydroxy-2-((R)-5-isobutyryl-1-oxo-2,5-diazaspiro[3.4]octan-2-yl)butanamide characterized by a powder X-ray diffraction pattern having a characteristic peak in degrees 2θ at about 10.8 (referred to herein as "Form MH"). The term "about" in the context of peaks at degrees 2θ means that there is an uncertainty in the measurements of the 2θ of ±0.5 (expressed in 2θ) or that there is an uncertainty in the measurements of the 2θ of ±0.2 (expressed in 2θ).

The crystalline Form MH of NYX-2925 can be characterized by a powder X-ray diffraction pattern that has a characteristic peak in degrees 2θ at about 13.4, can be characterized by a powder X-ray diffraction pattern that has a characteristic peak in degrees 2θ at about 16.6, can be characterized by a powder X-ray diffraction pattern that has a characteristic peak in degrees 2θ at about 18.4, can be characterized by a powder X-ray diffraction pattern that has a characteristic peak in degrees 2θ at about 18.6, can be characterized by a powder X-ray diffraction pattern that has a characteristic peak in degrees 2θ at about 20.8, can be characterized by a powder X-ray diffraction pattern that has a characteristic peak in degrees 2θ at about 21.0, can be characterized by a powder X-ray diffraction pattern that has a characteristic peak in degrees 2θ at about 21.6, can be characterized by a powder X-ray diffraction pattern that has a characteristic peak in degrees 2θ at about 23.1, can be characterized by a powder X-ray diffraction pattern that has a characteristic peak in degrees 2θ at about 25.2, can be characterized by a powder X-ray diffraction pattern that has a characteristic peak in degrees 2θ at about 25.6, can be characterized by a powder X-ray diffraction pattern that has a characteristic peak in degrees 2θ at about 29.7, and/or can be characterized by a powder X-ray diffraction pattern that has a characteristic peak in degrees 2θ at about 29.9.

The crystalline Form MH of NYX-2925 can be characterized by a powder X-ray diffraction pattern having at least one or more characteristic peaks in degrees 2θ at about 10.8, 13.4, and 18.4. The crystalline Form MH can be characterized by a powder X-ray diffraction pattern having at least one or more characteristic peaks in degrees 2θ at about 10.8, 13.4, and 18.4, 20.8, 21.0, and 25.2. The crystalline Form MI-1 can be characterized by a powder X-ray diffraction pattern having at least one or more characteristic peaks in degrees 2θ at about 10.8, 13.4, 16.6, 18.4, 18.6, 20.8, 21.0, 21.6, 25.2, 25.6, 29.7, and 29.9. For example, the crystalline Form MH can be characterized by a powder X-ray diffraction pattern substantially similar to FIG. 1. A powder X-ray diffraction pattern of the crystalline Form MI-1 can be obtained using Cu Kα radiation.

The crystalline Form MH of NYX-2925 can be characterized by a Fourier Transform-Raman (FT-Raman) spectrum that can have at least one or more characteristic aliphatic C—H stretching vibrations between about 2800 $cm^{-1}$ to about 3200 $cm^{-1}$ and/or at least one or more characteristic amide group bands between about 1620 $cm^{-1}$ to about 1740 $cm^{-1}$. In this context, the term "about" means that the $cm^{-1}$ values can vary, for example, up to ±5 $cm^{-1}$.

The crystalline Form MH of NYX-2925 can be characterized by a Thermogravimetric Fourier Transform Infrared (TG-FTIR) absorption spectrum that can show weight loss of about 5.4% in the temperature range of 40-150° C., and/or a chemical decomposition event starting above 210° C. For example, the crystalline Form MI-1 of NYX-2925 can be characterized by a TG-FTIR thermogram substantially similar to FIG. 2.

The crystalline Form MH of NYX-2925 can be characterized by a melting point of about 126° C., a melting enthalpy of about 145 J/g, and/or a differential scanning calorimetry (DSC) profile with a sharp endothermic peak due to melting at about 128° C. For example, the crystalline Form MI-1 of NYX-2925 can be characterized by a differential scanning calorimetry profile substantially similar to FIG. 3.

The crystalline Form MH of NYX-2925 can be characterized by a dynamic vapor sorption (DVS) profile showing reversible weight loss of about 5.5 wt. % in the 0-15% relative humidity (RH) range, with some observable hysteresis and about 1.5 wt. % continuous reversible weight gain up to about 95% relative humidity, or above about 90% relative humidity. For example, the crystalline Form MH can be characterized by a dynamic vapor sorption (DVS) profile substantially similar to FIG. 4.

The crystalline Form MH of NYX-2925 can be characterized as having a crystal space group of $P2_12_12_1$. For example, the crystalline Form MH of NYX-2925 can be characterized by the X-ray crystal structure shown in FIG. 5.

The crystalline Form MH of NYX-2925 can be characterized as having a solubility in acetone of about 57 mg/mL to about 76 mg/mL at ambient temperature (about 22° C.), a solubility in aniline of greater than about 200 mg/mL at ambient temperature, a solubility in anisole of about 3 mg/mL at ambient temperature, a solubility in cyclohexane of about 1 mg/mL about 1.16 g/100 g at ambient temperature, a solubility in dichloromethane of about 55 mg/mL to about 73 mg/mL at ambient temperature, a solubility in diisopropyl ether of less than about 1 mg/mL at ambient temperature, a solubility in 1.4-dioxane of about 28 mg/mL to about 31 mg/mL at ambient temperature, a solubility in dimethylformamide of greater than about 200 mg/mL at ambient temperature, a solubility in dimethyl sulfoxide of greater than about 200 mg/mL at ambient temperature, a solubility in ethyl acetate of about 13 mg/mL to about 15 mg/mL at ambient temperature, a solubility in ethanol of greater than about 200 mg/mL at ambient temperature, a solubility in heptane of less than about 1 mg/mL at ambient temperature, a solubility in acetonitrile of about 118 mg/mL to about 230 mg/mL at ambient temperature, a solubility in methanol of greater than about 200 mg/mL at ambient temperature, a solubility in methyl ethyl ketone of about 32 mg/mL to about 38 mg/mL at ambient temperature, a solubility in isopropyl acetate of about 5 mg/mL to about 6 mg/mL at ambient temperature, a solubility in isopropanol of about 45 mg/mL to about 60 mg/mL at ambient temperature, a solubility in tert-butyl methyl ether of less than about 1 mg/mL at ambient temperature, a solubility in tetrahydrofuran of about 31 mg/mL to about 36 mg/mL at ambient temperature, a solubility in toluene of less than about 1 mg/mL at ambient temperature, a solubility in trimethylamine of less than about 1 mg/mL at ambient temperature, a solubility in water of about 26 mg/mL to about 30 mg/mL at ambient temperature, a solubility in 1/1 dichloromethane/methanol of greater than about 200 mg/mL at ambient temperature, a solubility in 10/1 ethyl acetate/ethanol of about 32 mg/mL to about 39 mg/mL at ambient temperature, a solubility in ethyl acetate saturated with water of about 6 mg/mL to about 8 mg/mL at ambient temperature, a solubility in 1/1 ethanol/water of about 69 mg/mL to about 103 mg/mL at ambient temperature, a solubility in 1/1 methanol/water of greater than about 200 mg/mL at ambient temperature, a solubility in 1/1 isopropanol/water of about 71 mg/mL to about 107 mg/mL at ambient temperature, a solubility in 10/1 isopropanol/water of about 36 mg/mL to about 41 mg/mL at ambient temperature, and/or a solubility in tert-butyl methyl ether saturated with water of less than about 1 mg/mL at ambient temperature.

The crystalline Form MH of NYX-2925 can be characterized as having a solubility in an aqueous solvent (e.g., an aqueous solution that may include a buffer) with a pH of about 2 of about 54.1 mg/mL at ca. 25° C. after about 1 day, about 53.5 mg/mL after about 4 days, and/or about 53.5 mg/mL after about 7 days. The crystalline Form MEI can be characterized as having a solubility in an aqueous solvent with a pH of about 3 of about 54.2 mg/mL at ca. 25° C. after about 1 day, about 53.2 mg/mL after about 4 days, and/or about 52.4 mg/mL after about 7 days. The crystalline Form MH can be characterized as having a solubility in an aqueous solvent with a pH of about 5 of about 52.5 mg/mL at ca. 25° C. after about 1 day, about 53.2 mg/mL after about 4 days, and/or about 52.4 mg/mL after about 7 days. The crystalline Form MEI can be characterized as having a solubility in an aqueous solvent with a pH of about 7 of about 52.6 mg/mL at ca. 25° C. after about 1 day, about 53.0 mg/mL after about 4 days, and/or about 52.3 mg/mL after about 7 days. The crystalline Form can be characterized as having a solubility in an aqueous solvent with a pH of about 8 of about 52.7 mg/mL at ca. 25° C. after about 1 day, about 51.6 mg/mL after about 4 days, and/or about 52.6 mg/mL after about 7 days.

The present disclosure also provides anhydrous crystalline forms of 3-hydroxy-2-(5-isobutyryl-1-oxo-2,5-diazaspiro[3.4]octan-2-yl)butanamide. For example, the present disclosure provides an anhydrous crystalline form of 3-hydroxy-2-(5-isobutyryl-1-oxo-2,5-diazaspiro[3.4]octan-2-yl)butanamide characterized by a powder X-ray diffraction pattern having a characteristic peak in degrees 2θ at 13.9±0.2 (referred to herein as "Form A").

The anhydrous crystalline Form A of 3-hydroxy-2-(5-isobutyryl-1-oxo-2,5-diazaspiro[3.4]octan-2-yl)butanamide can be characterized by a powder X-ray diffraction pattern that has a characteristic peak in degrees 2θ at about 9.7, can be characterized by a powder X-ray diffraction pattern that has a characteristic peak in degrees 2θ at about 10.8, can be characterized by a powder X-ray diffraction pattern that has a characteristic peak in degrees 2θ at about 11.3, can be characterized by a powder X-ray diffraction pattern that has a characteristic peak in degrees 2θ at about 13.4, can be characterized by a powder X-ray diffraction pattern that has a characteristic peak in degrees 2θ at about 16.9, can be characterized by a powder X-ray diffraction pattern that has a characteristic peak in degrees 2θ at about 18.4, can be characterized by a powder X-ray diffraction pattern that has a characteristic peak in degrees 2θ at about 18.9, can be characterized by a powder X-ray diffraction pattern that has a characteristic peak in degrees 2θ at about 19.5, can be characterized by a powder X-ray diffraction pattern that has a characteristic peak in degrees 2θ at about 20.9, can be characterized by a powder X-ray diffraction pattern that has a characteristic peak in degrees 2θ at about 22.2, can be characterized by a powder X-ray diffraction pattern that has a characteristic peak in degrees 2θ at about 24.2, and/or can be characterized by a powder X-ray diffraction pattern that has a characteristic peak in degrees 2θ at about 25.5.

The crystalline Form A can be characterized by a powder X-ray diffraction pattern having at least one or more characteristic peaks in degrees 2θ at about 11.3, 13.9, and 18.9. The crystalline Form A can be characterized by a powder X-ray diffraction pattern having at least one or more characteristic peaks in degrees 2θ at about 10.8, 11.3, 13.9, 16.9, 18.9, and 20.9. The crystalline Form A can be characterized by a powder X-ray diffraction pattern having at least one or more characteristic peaks in degrees 2θ at about 9.7, 10.8, 11.3, 13.4, 13.9, 16.9, 18.9, 19.5, 20.9, 22.2, 23.4, and 25.5. A powder X-ray diffraction pattern of the crystalline Form A can be obtained using Cu Kα radiation.

The crystalline Form A of 3-hydroxy-2-(5-isobutyryl-1-oxo-2,5-diazaspiro[3.4]octan-2-yl)butanamide can be characterized by a melting point of about 144° C.

The crystalline Form A of 3-hydroxy-2-(5-isobutyryl-1-oxo-2,5-diazaspiro[3.4]octan-2-yl)butanamide can be characterized as having a solubility in water of about 54-55 mg/mL at room temperature (about 22° C.). The crystalline Form A of 3-hydroxy-2-(5-isobutyryl-1-oxo-2,5-diazaspiro[3.4]octan-2-yl)butanamide can be characterized as having a solubility in isopropyl acetate of about 8 mg/mL at room temperature (about 22° C.).

The present disclosure provides another anhydrous crystalline form of 3-hydroxy-2-(5-isobutyryl-1-oxo-2,5-diazaspiro[3.4]octan-2-yl)butanamide characterized by a powder X-ray diffraction pattern having a characteristic peak in degrees 2θ at about 15.5 (referred to herein as "Form B").

The anhydrous crystalline Form B of 3-hydroxy-2-(5-isobutyryl-1-oxo-2,5-diazaspiro[3.4]octan-2-yl)butanamide can be characterized by a powder X-ray diffraction pattern that has a characteristic peak in degrees 2θ at about 10.8, can be characterized by a powder X-ray diffraction pattern that has a characteristic peak in degrees 2θ at about 13.4, can be characterized by a powder X-ray diffraction pattern that has a characteristic peak in degrees 2θ at about 14.0, can be characterized by a powder X-ray diffraction pattern that has a characteristic peak in degrees 2θ at about 16.6, can be characterized by a powder X-ray diffraction pattern that has a characteristic peak in degrees 2θ at about 18.4, can be characterized by a powder X-ray diffraction pattern that has a characteristic peak in degrees 2θ at about 20.2, can be characterized by a powder X-ray diffraction pattern that has a characteristic peak in degrees 2θ at about 20.6, can be characterized by a powder X-ray diffraction pattern that has a characteristic peak in degrees 2θ at about 22.3, can be characterized by a powder X-ray diffraction pattern that has a characteristic peak in degrees 2θ at about 22.8, can be characterized by a powder X-ray diffraction pattern that has a characteristic peak in degrees 2θ at about 24.9, can be characterized by a powder X-ray diffraction pattern that has a characteristic peak in degrees 2θ at about 26.0, and/or can be characterized by a powder X-ray diffraction pattern that has a characteristic peak in degrees 2θ at about 26.6.

The crystalline Form B can be characterized by a powder X-ray diffraction pattern having at least one or more characteristic peaks in degrees 2θ at about 10.8, 15.5, and 20.2. The crystalline Form B can be characterized by a powder X-ray diffraction pattern having at least one or more characteristic peaks in degrees 2θ at about 10.8, 14.0, 15.5, 16.6, 18.4, and 20.2. The crystalline Form B can be characterized by a powder X-ray diffraction pattern having at least one or more characteristic peaks in degrees 2θ at about 10.8, 13.4, 14.0, 15.5, 16.6, 18.4, 20.2, 20.6, 22.8, 24.9, 26.0, and 26.6. A powder X-ray diffraction pattern of the crystalline Form B can be obtained using Cu Kα radiation.

The crystalline Form B of 3-hydroxy-2-(5-isobutyryl-1-oxo-2,5-diazaspiro[3.4]octan-2-yl)butanamide can be characterized by a melting point of about 154° C.

The crystalline Form B of 3-hydroxy-2-(5-isobutyryl-1-oxo-2,5-diazaspiro[3.4]octan-2-yl)butanamide can be characterized as having a solubility in water of about 54 mg/mL after 10 minutes at room temperature, a solubility in water of about 54 mg/mL after 1 hour at room temperature, and/or a solubility in water of about 48 mg/mL after 6 hours at room temperature. The crystalline Form B of 3-hydroxy-2-(5-isobutyryl-1-oxo-2,5-diazaspiro[3.4]octan-2-yl)butanamide can be characterized as having a solubility in isopropyl acetate of about 9 mg/mL after 10 minutes, 1 hour, and/or 6 hours at room temperature.

The present disclosure provides yet another anhydrous crystalline form of 3-hydroxy-2-(5-isobutyryl-1-oxo-2,5-diazaspiro[3.4]octan-2-yl)butanamide characterized by a powder X-ray diffraction pattern having a characteristic peak in degrees 2θ at about 17.7 (referred to herein as "Form C").

The anhydrous crystalline Form C of 3-hydroxy-2-(5-isobutyryl-1-oxo-2,5-diazaspiro[3.4]octan-2-yl)butanamide can be characterized by a powder X-ray diffraction pattern that has a characteristic peak in degrees 2θ at about 8.8, can be characterized by a powder X-ray diffraction pattern that has a characteristic peak in degrees 2θ at about 9.6, can be characterized by a powder X-ray diffraction pattern that has a characteristic peak in degrees 2θ at about 12.6, can be characterized by a powder X-ray diffraction pattern that has a characteristic peak in degrees 2θ at about 15.7, can be characterized by a powder X-ray diffraction pattern that has a characteristic peak in degrees 2θ at about 16.7, can be characterized by a powder X-ray diffraction pattern that has a characteristic peak in degrees 2θ at about 17.0, can be characterized by a powder X-ray diffraction pattern that has a characteristic peak in degrees 2θ at about 17.7, can be characterized by a powder X-ray diffraction pattern that has a characteristic peak in degrees 2θ at about 20.5, can be characterized by a powder X-ray diffraction pattern that has a characteristic peak in degrees 2θ at about 21.9, can be characterized by a powder X-ray diffraction pattern that has a characteristic peak in degrees 2θ at about 22.5, can be characterized by a powder X-ray diffraction pattern that has a characteristic peak in degrees 2θ at about 26.4, can be characterized by a powder X-ray diffraction pattern that has a characteristic peak in degrees 2θ at about 29.3, and/or can be characterized by a powder X-ray diffraction pattern that has a characteristic peak in degrees 2θ at about 33.5.

The crystalline Form C can be characterized by a powder X-ray diffraction pattern having at least one or more characteristic peaks in degrees 2θ at about 15.7, 16.7, and 17.7. The crystalline Form C can be characterized by a powder X-ray diffraction pattern having at least one or more characteristic peaks in degrees 2θ at about 8.8, 15.7, 16.7, 17.0, 17.7, and 26.4. The crystalline Form C can be characterized by a powder X-ray diffraction pattern having at least one or more characteristic peaks in degrees 2θ at about 8.8, 9.6, 12.6, 15.7, 16.7, 17.0, 17.7, 20.5, 21.9, 16.4, 29.3, and 33.5. A powder X-ray diffraction pattern of the crystalline Form C can be obtained using Cu Kα radiation.

The present disclosure also provides an amorphous form of 3-hydroxy-2-(5-isobutyryl-1-oxo-2,5-diazaspiro[3.4]octan-2-yl)butanamide. The amorphous form of 3-hydroxy-2-(5-isobutyryl-1-oxo-2,5-diazaspiro[3.4]octan-2-yl)butanamide can be characterized by a differential scanning calorimetry (DSC) profile with a glass transition of the amorphous form at about 59° C.

Pharmaceutical Formulations

In one aspect, provided herein is a pharmaceutical formulation comprising (2S,3R)-3-hydroxy-2-((R)-5-isobutyryl-1-oxo-2,5-diazaspiro[3.4]octan-2-yl)butanamide ("NYX-2925"), or a pharmaceutically acceptable salt thereof, and a pharmaceutically acceptable excipient, which can be used for the treatment of painful diabetic peripheral neuropathy.

In some embodiments, the pharmaceutical formulation comprises NYX-2925, or a pharmaceutically acceptable salt thereof, present in a therapeutically effective amount; and a pharmaceutically acceptable excipient. In some embodiments, the pharmaceutically acceptable excipient is one or more of microcrystalline cellulose; pregelatinized starch, and magnesium stearate.

In some embodiments, the pharmaceutical formulation is encapsulated in a capsule. In some embodiments, the capsule comprises hydroxyl-propyl cellulose. In some embodiments, the capsule comprises about 10 mg of NYX-2925, or a pharmaceutically acceptable salt thereof; about 50 mg of NYX-2925, or a pharmaceutically acceptable salt thereof; about 100 mg NYX-2925, or a pharmaceutically acceptable salt thereof; or about 200 mg NYX-2925, or a pharmaceutically acceptable salt thereof.

In some embodiments, the pharmaceutical formulation is in the form of a tablet. In some embodiments, the tablet comprises about 10 mg of NYX-2925, or a pharmaceutically acceptable salt thereof; about 50 mg of NYX-2925, or a pharmaceutically acceptable salt thereof; about 100 mg NYX-2925, or a pharmaceutically acceptable salt thereof; or about 200 mg NYX-2925, or a pharmaceutically acceptable salt thereof.

In some embodiments, NYX-2925 comprises a crystalline form of NYX-2925 monohydrate. In some embodiments, the crystalline form of NYX-2925 monohydrate is characterized by a powder X-ray diffraction pattern comprising characteristic peaks in degrees 2θ at about 10.8, 13.4, and 18.4.

In certain embodiments, the amount of NYX-2925, or a pharmaceutically acceptable salt thereof, in the pharmaceutical formulation is from about 25 mg to about 150 mg, about 50 mg to about 150 mg, about 75 mg to about 150 mg, about 100 mg to about 150 mg, about 125 mg to about 150 mg, about 25 mg to about 125 mg, about 25 mg to about 100 mg, about 25 mg to about 75 mg, about 25 mg to about 50 mg, about 50 mg to about 125 mg, about 50 mg to about 100 mg, about 50 mg to about 75 mg, about 75 mg to about 125 mg, about 75 mg to about 100 mg, or about 100 mg to about 125 mg.

In certain embodiments, the amount of NYX-2925, or a pharmaceutically acceptable salt thereof, in the pharmaceutical formulation is about 25 mg, about 50 mg, about 75 mg, about 100 mg, about 125 mg, about 150 mg, about 175 mg, or about 200 mg. In some embodiments, the amount of NYX-2925, or a pharmaceutically acceptable salt thereof, in the pharmaceutical formulation is about 50 mg. In some embodiments, the amount of NYX-2925, or a pharmaceutically acceptable salt thereof, in the pharmaceutical formulation is about 100 mg. In some embodiments, the amount of NYX-2925, or a pharmaceutically acceptable salt thereof, in the pharmaceutical formulation is about 25 mg.

In certain embodiments, the pharmaceutical formulation comprises an effective amount of a pharmaceutically acceptable salt of NYX-2925.

In certain embodiments, the pharmaceutical formulation comprises an effective amount of a pharmaceutically acceptable solvate of NYX-2925, or a solvate of a pharmaceutically acceptable salt of NYX-2925. In some embodiments, the solvate is a hydrate. In some embodiments, the solvate is a monohydrate.

In certain embodiments, the pharmaceutical formulation provided herein can be in a solid dosage form. In some embodiments, the solid dosage form is a capsule.

In some embodiments, about 50 mg of NYX-2925 or a pharmaceutically acceptable salt thereof is provided as a unit dose. In some embodiments, about 100 mg of NYX-2925 or a pharmaceutically acceptable salt thereof is provided as a unit dose. In some embodiments, about 200 mg of NYX-2925 or a pharmaceutically acceptable salt thereof is provided as a unit dose.

In certain embodiments, the pharmaceutical formulation comprises NYX-2925 or a pharmaceutically acceptable salt thereof; and a pharmaceutically acceptable excipient.

In certain embodiments, the pharmaceutical formulation is a formulation for oral administration.

Although the descriptions of pharmaceutical formulations provided herein are principally directed to pharmaceutical formulations which are suitable for administration to humans, it will be understood by the skilled artisan that such formulations are generally suitable for administration to animals of all sorts. Modification of pharmaceutical formulations suitable for administration to humans in order to render the formulations suitable for administration to various animals is well understood, and the ordinarily skilled veterinary pharmacologist can design and/or perform such modification with ordinary experimentation. General considerations in the formulation and/or manufacture of pharmaceutical formulations can be found, for example, in Remington: The Science and Practice of Pharmacy 21$^{st}$ ed., Lippincott Williams & Wilkins, 2005.

Methods of Use and Treatment

In one aspect, provided herein are methods of treating advanced painful diabetic peripheral neuropathy (DPN) in a patient in need thereof, comprising administering to the patient a therapeutically effective amount of (2S,3R)-3-hydroxy-2-((R)-5-isobutyryl-1-oxo-2,5-diazaspiro[3.4]octan-2-yl)butanamide ("NYX-2925"), or a pharmaceutically acceptable salt thereof. In some embodiments, the administering comprises administering orally NYX-2925, or a pharmaceutically acceptable salt thereof. In certain embodiments, administering comprises administering daily NYX-2925, or a pharmaceutically accepted salt thereof. In particular embodiments, administering comprises administering orally NYX-2925, or a pharmaceutically acceptable salt thereof, once daily.

In some embodiments, the patient has suffered from painful DPN for longer than one year, for longer than two years, for longer than three years, for longer than four years, for longer than five years, or more. Such time periods can be indicative of advanced painful DPN.

In some embodiments, the therapeutically effective amount of NYX-2925, or a pharmaceutically acceptable salt thereof, is between about 10 mg and about 200 mg. In some embodiments, the therapeutically effective amount is between about 15 mg to about 180 mg, between about 20 mg to about 160 mg, between about 25 mg to about 140 mg, between about 30 mg to about 120 mg, between about 35 mg to about 100 mg, between about 40 mg to about 80 mg, or between about 45 mg to about 60 mg. In some embodiments, the therapeutically effective amount is between about 44 mg to about 56 mg, between about 45 mg to about 55 mg, between about 46 mg to about 54 mg, between about 47 mg to about 53 mg, between about 48 mg to about 52 mg, or between about 49 mg to about 51 mg. In some embodiments, the therapeutically effective amount is about 50 mg.

In some embodiments, the patient has reduced sleep interference after about 1 week, after about 2 weeks, after about 3 weeks, after about 4 weeks, or after about 5 weeks or more of daily administration of NYX-2925, or a pharmaceutically acceptable salt thereof.

In some embodiments, the patient is not being administered another analgesic. In some embodiments, the patient is being administered another analgesic.

In some embodiments, administering comprises administering daily to the patient a pharmaceutical formulation, wherein the pharmaceutical formulation comprises NYX-2925, or a pharmaceutically acceptable salt thereof, present in a therapeutically effective amount; and a pharmaceutically acceptable excipient, for example, one or more of microcrystalline cellulose; pregelatinized starch, and magnesium stearate.

In some embodiments, the pharmaceutical formulation is encapsulated in a capsule. In some embodiments, the capsule comprises hydroxyl-propyl cellulose. In some embodiments, the capsule comprises about 10 mg of NYX-2925, or a pharmaceutically acceptable salt thereof; about 50 mg of NYX-2925, or a pharmaceutically acceptable salt thereof; about 100 mg NYX-2925, or a pharmaceutically acceptable salt thereof; or about 200 mg NYX-2925, or a pharmaceutically acceptable salt thereof.

In some embodiments, the pharmaceutical formulation is in the form of a tablet. In some embodiments, the tablet comprises about 10 mg of NYX-2925, or a pharmaceutically acceptable salt thereof; about 50 mg of NYX-2925, or a pharmaceutically acceptable salt thereof; about 100 mg NYX-2925, or a pharmaceutically acceptable salt thereof; or about 200 mg NYX-2925, or a pharmaceutically acceptable salt thereof. In some embodiments, the tablet comprises about 20 mg of NYX-2925, or a pharmaceutically acceptable salt thereof; about 25 mg of NYX-2925, or a pharmaceutically acceptable salt thereof; about 30 mg of NYX-2925, or a pharmaceutically acceptable salt thereof; about 40 mg of NYX-2925, or a pharmaceutically acceptable salt thereof.

In some embodiments, the patient is human.

In some embodiments, painful DPN is characterized by a Michigan Neuropathy Screening Instrument (MNSI) score of greater than or equal to 3.

The pharmaceutical methods provided herein can include administration by oral (enteral) administration. That is, in some embodiments, the methods include administering orally a compound or a pharmaceutical formulation disclosed herein.

The methods provided herein may also include chronic administration. Chronic administration refers to administration of a compound or pharmaceutical formulation comprising a compound disclosed herein over an extended period of time, e.g., over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical formulations provided herein may be presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

In certain embodiments, the pharmaceutical formulations provided herein are administered to the patient as a solid dosage form. In some embodiments, the solid dosage form is a capsule.

In certain embodiments, the compounds provided herein can be administered as the sole active agent, or they can be administered in combination with other therapeutically active agents.

In certain embodiments, administering an effective amount of NYX-2925, or a pharmaceutically acceptable salt thereof, comprises administering orally about 50 mg of NYX-2925, or a pharmaceutically acceptable salt thereof, once daily.

In certain embodiments, administering an effective amount of NYX-2925, or a pharmaceutically acceptable salt thereof, comprises administering orally about 75 mg of NYX-2925, or a pharmaceutically acceptable salt thereof, once daily.

In certain embodiments, administering an effective amount of NYX-2925, or a pharmaceutically acceptable salt thereof, comprises administering orally about 100 mg of NYX-2925, or a pharmaceutically acceptable salt thereof, once daily.

In some embodiments, the about 50 mg of NYX-2925 or a pharmaceutically acceptable salt thereof is provided as a unit dose. In some embodiments, the about 50 mg of NYX-2925 or a pharmaceutically acceptable salt thereof is provided as a 25 mg unit dose and a 25 mg unit dose.

In certain embodiments, administering an effective amount of NYX-2925 provides a constant level, or near constant level, of the compound in the blood.

Also provided herein are combination therapies comprising a compound of the disclosure in combination with one or more other active agents. For example, a compound may be combined with one or more analgesics, such as non-steroidal anti-inflammatory agents (NSAIDS), steroidal anti-inflammatory agents, opiates, and cyclo-oxygenase inhibitors. A compound may also be combined with other agents such as antidepressants, such as tricyclic antidepressants, MAO-I's, SSRI's, SNRI's and double and triple uptake inhibitors and/or anxiolytic drugs. Exemplary drugs that may be used in combination with a compound include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In another example, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. In another example, a compound may be combined with an antiepileptic medication. Non-limiting examples of antiepileptics include gabapentin, pregabalin, carbamazepine, clonazepam, lacosamide, lamotrigine, levetiracetam, oxcarbazepine, phenytoin, pregabalin, topiramate, and valproate. Use of any of the drugs named herein can include use of its branded or generic equivalents. It should be understood that combinations of a compound and one or more of the above therapeutics may be used for treatment of any suitable condition and are not limited to use as anti-pain medication.

EXAMPLES

In order that the disclosure described herein may be more fully understood, the following examples are set forth. The synthetic and biological examples described in this application are offered to illustrate the compounds, pharmaceutical formulations, and methods provided herein and are not to be construed in any way as limiting their scope.

The compounds described herein can be prepared in a number of ways based on the teachings contained herein and synthetic procedures known in the art. The following non-limiting examples illustrate the disclosure.

X-ray powder diffraction (XRPD) analysis was carried out on a Stoe Stadi P with Mythen1K detector; Cu-Kα1 radiation; 40 kV and 40 mA tube power; curved Ge monochromator; 0.02° 2θ step size, 12 s step time, 1.5-50.5° 2θ scanning range; detector mode: step scan; 1° 2θ detector step. The sample (about 20 mg) was placed between two acetate foils and clamped in a Stoe transmission sample holder. The sample holder was rotated during the measurement.

X-ray powder diffraction (XRPD) analysis was also carried out on a on a Bruker D8 Advance; Cu-Kα radiation; standard measurement conditions: Bragg-Brentano reflection geometry; 40 kV and 40 mA tube power; LynxEye detector; 0.02° 2θ step size, 37 s step time, 2.5-50.5° 2θ scanning range (about 10 min measurement time. The sample was spread on a silicon single crystal substrate without cavity and flattened to fit to the 0.1 mm depth of the sample holder.

All sample preparation and measurement was done in ambient air at approximately one atmosphere of pressure.

FT-Raman spectroscopy data was collected on a Bruker Multi-RAM with OPUS 6.5 software; Nd:YAG 1064-nm excitation, Ge detector, 3500-50 cm-1 range; typical measurement conditions: 300 mW nominal laser power, 64 scans, 2 cm-1 resolution; samples pressed into the cavity of aluminum sample holders. Differential Scanning calorimetry (DSC) was conducted as follows.

Thermogravimetric FT-IR spectroscopy data was collected on a Netzsch Thermo-Microbalance TG 209 with Bruker FT-IR Spectrometer Vector 22; aluminum crucible (with microhole); $N_2$ atmosphere; 10° C./min heating rate, from 25 to 300° C.

Differential scanning calorimetry (DSC) data was collected on a TA Instruments DSC Q2000; hermetically closed gold crucible; $N_2$ atmosphere; 10° C./min heating rate, from 20 to 200° C. The melting point is understood as the peak onset.

Approximate solubilities were determined by a stepwise dilution of a suspension of about 10 mg of substance in 0.05 mL of solvent. If the substance was not dissolved by addition of a total of at least 10 ml solvent, the solubility was indicated as <1 mg/mL. For all experiments, analytical grade solvents were used.

Single crystal X-ray data collected on D8 Venture Photon 100 CMOS diffractometer using graphite monochromatized Mo-Kα radiation (=0.7107 A) with an exposure per frame of 15 secs. The X-ray generator was operated at 50 kV and 30 mA. A total of 11 data sets were collected having 1589 frames. The optimized strategy used for data collection of consisted different sets of ψ and ω scans with 0.5° steps in ψ/ω. Data integration was carried out by the Bruker SAINT Program and empirical absorption correction for intensity data was carried out by Bruker SADABS. The Programs are integrated in the APEX II package. The data were corrected for Lorentz and polarization effect. The structure was solved by Direct Method using SHELX-97. The final refinement of the structure was performed by full-matrix least-squares techniques with anisotropic thermal data for non-hydrogen atoms on $F^2$. The non-hydrogen atoms were refined anisotropically, whereas the hydrogen atoms were refined at calculated positions as riding atoms with isotropic displacement parameters. Unit cell determination was carried out on a Bruker D8 Venture equipped with a Photon 100 CMOS detector. An initial set of cell constants and an orientation matrix were calculated from total 24 frames.

Chemical Definitions

Herein, the following chemical definitions are used: "Bn" is benzyl, "Boc" is tert-butoxycarbonyl, "BOM" is benzyloxymethyl, "DCM" is dichloromethane, "DIAD" is diisopropyl azodicarboxylate, "DIPEA" is N,N-diisopropylethylamine, "EDCI" is 1-ethyl-3-(3-dimethylaminopropyl) carbodiimide, "HATU" is (1-[Bis(dimethylamino) methylene]-1H-1,2,3-triazolo[4,5-b]pyridinium 3-oxid hexafluorophosphate, "¹H-NMR" is proton nuclear magnetic resonance. "HOBT" is hydroxybenzotriazole, "LCMS" is liquid chromatography-mass spectrometry, "LiHMDS" is lithium bis(trimetlaylsilyl)amide, "RT" is room temperature, "TEA" is triethylamine, "TFA" is trifluoroacetic acid, and "TLC" is thin-layer chromatography.

Example 1: Synthesis of NYX-2925

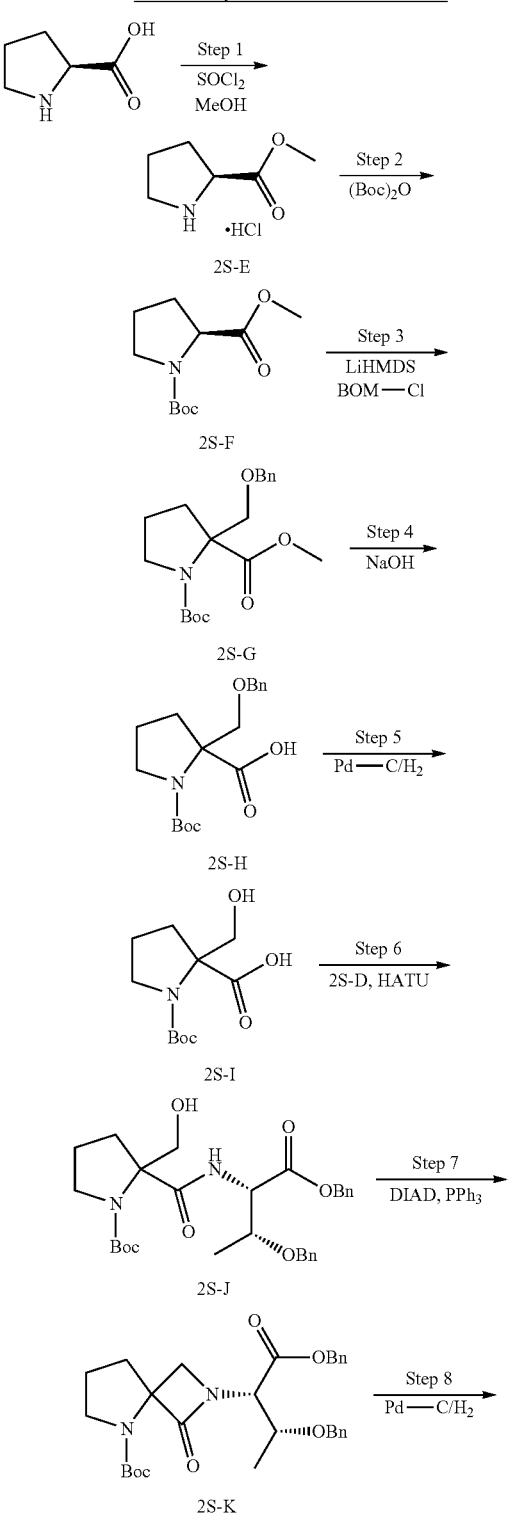

Scheme 1-Synthesis of Intermediate 2S-L

-continued

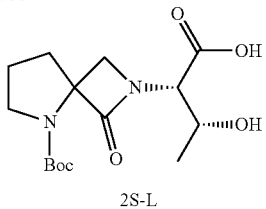 [SMILES: C[C@@H](O)[C@@H](C(=O)O)N1CC2(CCCN2C(=O)OC(C)(C)C)C1=O]

2S-L

Synthesis of methyl pyrrolidine-2-carboxylate (2S-E)

To a stirring solution of L-proline (50 g, 434 mmol) in methanol was added thionyl chloride (37.5 ml, 521 mmol) at 0° C. and heated to 70° C. for 16 h. The reaction mixture was brought to RT and concentrated under vacuum to afford compound 2S-E as (70 g, 99%) as thick syrup (hydrochloride salt).

$^1$H-NMR: (500 MHz, DMSO-$d_6$): δ 4.15-4.13 (m, 1H), 3.65 (s, 3H), 3.35-3.30 (m, 2H), 2.23-2.15 (m, 1H), 1.86-1.78 (m, 3H), 1.41 (s, 9H);

LCMS m/z: 129 [M$^+$+1]

Synthesis of 1-tert-butyl 2-methyl pyrrolidine-1,2-dicarboxylate (2S-F)

To a stirring solution of compound 2S-E (70 g, 422 mmol) in CH$_2$Cl$_2$ (700 mL) were added Et$_3$N (183 mL, 1.26 mol) at 0° C. and stirred for 10 min. After added Boc-anhydride (184 mL, 845 mmol) at 0° C. and the reaction mixture was stirred at RT for 16 h. After consumption of the starting material (by TLC), the reaction was diluted with water (200 mL) and extracted with CH$_2$Cl$_2$ (2×200 mL). The combined organic layer was washed with citric acid (1×150 mL), brine (1×200 mL). The organic layer was dried over Na$_2$SO$_4$ and concentrated under reduced pressure to afford crude compound which was purified by column chromatography by eluting 50% EtOAC/n-hexane to obtain compound 2S-F (80 g, 83%) as thick syrup.

$^1$H-NMR: (400 MHz, DMSO-$d_6$): δ 4.15-4.13 (m, 1H), 3.65 (s, 3H), 3.35-3.30 (m, 2H), 2.23-2.15 (m, 1H), 1.86-1.78 (m, 3H), 1.41 (s, 9H);

LCMS m/z: 229 [(M$^+$+1)-Boc].

Synthesis of 1-tert-butyl 2-methyl 2-((benzyloxy) methyl) pyrrolidine-1,2-dicarboxylate (2S-G)

To a stirring solution of compound 2S-F (25 g, 109 mmol) in THF (250 mL) was added LiHMDS (240 mL, 240 mmol) at –20° C. and stirred for 2 h. To this BOM-chloride (23 mL, 163 mmol) was added drop wise at –30° C. and stirred for 2 h. After consumption of the starting material (by TLC), the reaction was quenched with aqueous NH$_4$Cl solution (100 mL) and extracted with EtOAc (2×200 mL). The combined organic layer was washed with water (2×150 mL) followed by brine solution (2×100 mL). The organic layer was dried over Na$_2$SO$_4$ and concentrated to obtain crude compound which was purified by column chromatography by eluting 10% EtOAc/n-hexane to afford compound 2S-G (30 g, 79%) as thick syrup.

$^1$H-NMR: (500 MHz, DMSO-$d_6$): δ 7.36-7.22 (m, 5H), 4.59-4.48 (m, 2H), 4.02-3.88 (m, 1H), 3.63 (s, 3H), 3.49-3.35 (m, 2H), 3.34-3.30 (m, 1H), 2.31-2.23 (m, 1H), 2.04-1.89 (m, 2H), 1.82-1.78 (m, 1H);

LCMS m/z: 349.4 [(M$^+$+1)-Boc]

Synthesis of 2-((benzyloxy) methyl)-1-(tert-butoxycarbonyl) pyrrolidine-2-carboxylic acid (2S-H)

To a stirring solution of compound 2S-G (30 g, 86 mmol) in methanol (70 mL) was added NaOH solution (6.88 g in 70 mL H$_2$O) at RT. The reaction mixture was heated to 70° C. for 16 h. After consumption of the starting material (by TLC), the solvent from the reaction was evaporated under reduced pressure and diluted with EtOAc (2×200 mL). The separated aqueous layer was acidified using citric acid solution (pH-3) and extracted with EtOAc (2×250 mL). The combined organic layer was dried over Na$_2$SO$_4$ and concentrated to afford crude was triturated with n-hexane to obtain compound 2S-H (25 g, 86.8%) as an off-white solid.

$^1$H-NMR: (400 MHz, DMSO-$d_6$): δ 12.35 (br s, 1H), 7.37-7.29 (m, 5H), 4.56-4.48 (m, 2H), 4.06-4.00 (m, 1H), 3.92-3.89 (m, 1H), 3.66-3.45 (m, 1H), 3.37-3.28 (m, 1H), 2.31-2.20 (m, 1H), 2.05-1.97 (m, 1H), 1.87-1.75 (m, 2H), 1.38 (s, 9H);

LCMS m/z: 335.3 [M$^+$+1]

Synthesis of 1-(tert-butoxycarbonyl)-2-(hydroxymethyl) pyrrolidine-2-carboxylic acid (2S-I)

To a stirring solution of compound 2S-H (25 g, 74 mmol) in methanol (150 mL) was added 50% wet 10% Pd/C (7 g) at RT and stirred for 10 h under H$_2$ atmosphere. After consumption of the starting material (by TLC), the reaction mixture was filtered through a pad of celite and the pad was washed with methanol (100 mL). Obtained filtrate was concentrated under reduced pressure to afford compound 2S-I (15 g, 82.8%) as white solid.

$^1$H-NMR: (400 MHz, DMSO-$d_6$): δ 4.66 (br s, 1H), 3.96-3.83 (m, 1H), 3.63-3.59 (m, 1H), 3.49-3.41 (m, 1H), 3.34-3.25 (m, 1H), 2.30-2.17 (m, 1H), 1.95-1.72 (m, 3H), 1.38 (s, 9H).

Mass (ESI): m/z 245 [M$^+$+1]

Synthesis of tert-butyl 2-(((2S,3R)-1,3-bis (benzyloxy)-1-oxobutan-2-yl) carbamoyl)-2-(hydroxymethyl) pyrrolidine-1-carboxylate (2S-J)

To a stirring solution of compound 2S-I (18 g, 73.4 mmol) in CH$_2$Cl$_2$ (180 mL) were added DIPEA (40 mL, 220 mmol), 2S-D (21.9 g, 73.4 mmol), HATU (41.8 g, 110 mmol) at RT and stirred for 16 h. After consumption of the starting material (by TLC), the reaction mixture was diluted with water (50 mL) and extracted with CH$_2$Cl$_2$ (2×100 mL). The combined organic layer was washed with brine, dried over anhydrous Na$_2$SO$_4$, filtered and concentrated under reduced pressure. Obtained crude material was purified by silica gel column chromatography eluting with 30% EtOAc/n-hexane to afford compound 2S-J (20 g, 52%) as pale yellow thick syrup.

$^1$H-NMR: (400 MHz, DMSO-$d_6$): δ 8.25-8.12 (m, 1H), 7.31-7.27 (m, 10H), 5.85 (t, J=4.8 Hz, 1H), 5.14 (s, 2H), 4.54-4.49 (m, 2H), 4.31-4.20 (m, 1H), 4.15-4.07 (m, 1H), 3.91-3.50 (m, 1H), 3.52-3.37 (m, 1H), 3.31-3.27 (m, 2H), 2.35-2.07 (m, 1H), 1.95-1.90 (m, 1H), 1.73-1.52 (m, 2H), 1.39 (s, 9H), 1.19 (d, J=6.4 Hz, 3H);

Mass (ESI): m/z 527.4 [M$^+$+1]

Synthesis of tert-butyl 2-((2S,3R)-1,3-bis (benzyloxy)-1-oxobutan-2-yl)-1-oxo-2,5-diazaspiro [3.4] octane-5-carboxylate (2S-K)

To a stirring solution of triphenylphosphine (24.7 g, 94 mmol) in THF (100 mL) was added DIAD (15.3 g, 75 mmol) at RT and stirred for 30 min. To this added compound 2S-J (20 g, 37.9 mmol) in (10 mL) THF slowly and reaction mixture was stirred at RT for 2 h. After consumption of the starting material (by TLC), the reaction was concentrated under reduced pressure. The crude material was purified by silica gel column chromatography eluting 25% EtOAc/n-hexane to afford compound 2S-K (17 g, 88%) as pale yellow thick syrup.

$^1$H-NMR: (400 MHz, DMSO-$d_6$): δ 7.33-7.26 (m, 5H), 7.23-7.18 (m, 5H), 5.10 (s, 2H), 4.80-4.73 (m, 2H), 4.60 (s, 2H), 4.31 (s, 2H), 4.05-4.00 (m, 2H), 1.80-1.68 (m, 4H), 1.39 (s, 9H), 1.18 (d, J=6.0 Hz, 3H);

Mass (ESI): m/z 509.4 [M$^+$+1]

Synthesis of (2S,3R)-2-(5-(tert-butoxycarbonyl)-1-oxo-2,5-diazaspiro [3.4] octan-2-yl)-3-hydroxybutanoic acid (2S-L)

To a stirring solution of compound 2S-K (7 g, 13.7 mmol) in methanol (100 mL) was added 10% Pd/C (4 g) at RT and stirred for 6 h under H$_2$ atmosphere. After consumption of the starting material (by TLC), the reaction mixture was filtered through a pad of celite and the pad was washed with methanol (50 mL). Obtained filtrate was concentrated under reduced pressure to obtained crude, which was triturated with n-pentane (50 mL) to afford compound 2S-L (4 g, 88%) as white solid.

$^1$H-NMR: (500 MHz, DMSO-$d_6$): δ 12.80 (br s, 1H), 4.78-4.73 (m, 1H), 4.21-4.19 (m, 1H), 4.09 (s, 2H), 3.55-3.46 (m, 2H), 2.09-2.05 (m, 2H), 1.80 (d, J=7.0 Hz, 1H), 1.38 (s, 9H), 1.35-1.28 (m, 2H), 1.17 (d, J=6.5 Hz, 3H)

LCMS m/z: 329.6 [M$^+$+1]

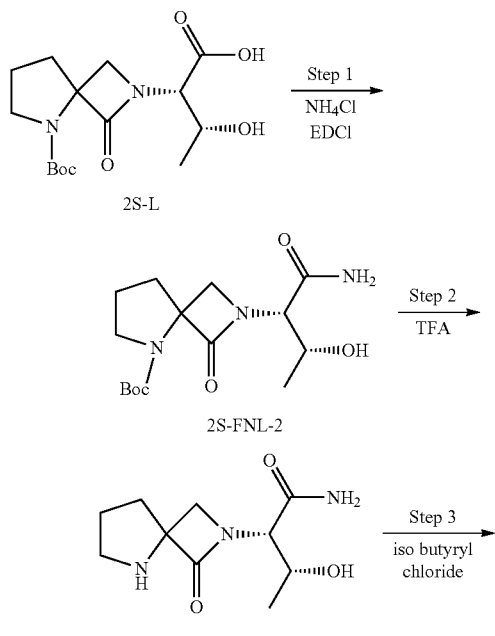

Scheme 2: Synthesis of NYX-2925 from 2S-L

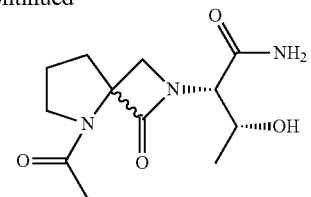

2S-FNL-4

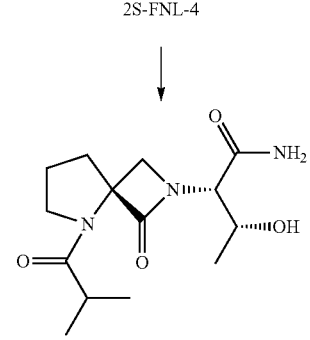

NYX-2925

Synthesis of tert-butyl 2-((2S,3R)-1-amino-3-hydroxy-1-oxobutan-2-yl)-1-oxo-2,5-diazaspiro [3.4] octane-5-carboxylate (2S-FNL-2)

To a stirring solution of compound 2S-L (500 mg, 1.52 mmol) in CH$_2$Cl$_2$ (5 mL) were added DIPEA (0.8 mL, 4.57 mmol), EDCI·HCl (350 mg, 1.82 mmol) followed by HOBt (280 mg, 1.82 mmol), NH$_4$Cl (161 mg, 3.04 mmol) at 0° C. and stirred for 16 h at RT. After consumption of the starting material (by TLC), the reaction mixture was diluted with water (10 mL) and extracted with CH$_2$Cl$_2$ (2×30 mL). The combined organic layer was washed with citric acid solution (2×30 mL). The organic layer was dried over anhydrous Na$_2$SO$_4$, filtered and concentrated under reduced pressure. Obtained crude material was purified by silica gel column chromatography eluting 2% MeOH/DCM to afford compound (2S-FNL-2) (200 mg, 40%) as colorless liquid.

$^1$H-NMR: (500 MHz, DMSO-$d_6$): δ 7.53 (s, 2H), 4.59 (s, 1H), 4.02 (s, 1H), 3.77-3.70 (m, 2H), 3.62-3.53 (m, 2H), 3.46-3.33 (m, 1H), 2.17-2.03 (m, 2H), 1.88-1.71 (m, 2H), 1.38 (s, 9H), 1.18 (d, J=6.5 Hz, 3H);

Mass (ESI): 328.3 [M$^+$+1]

Synthesis of (2S,3R)-3-hydroxy-2-(1-oxo-2,5-diazaspiro [3.4] octan-2-yl) butanamide (2S-FNL-3)

To a stirring solution of compound (2S-FNL-2) (200 mg, 0.61 mmol) in CH$_2$Cl$_2$ (5 mL) was added TFA (0.5 mL, 6.1 mmol) at 0° C. and stirred at RT for 3 h. After completion of reaction (by TLC), the reaction mixture was concentrated under reduced pressure to obtained crude compound which was triturated with n-pentane/diethylether (5 mL/5 mL) to afford compound (2S-FNL-3) (100 mg) as white solid (TFA salt).

$^1$H-NMR: (400 MHz, D$_2$O): δ 4.33-4.29 (m, 2H), 4.09 (d, 1H), 3.95 (d, 1H), 3.57-3.48 (m, 2H), 2.51-2.46 (m, 2H), 2.25-2.19 (m, 2H), 1.31 (d, 3H);

LCMS, m/z: 455 [2M$^+$+1]

Synthesis of (2S,3R)-3-hydroxy-2-(5-isobutyryl-1-oxo-2,5-diazaspiro [3.4] octan-2-yl) butanamide (NYX-2925)

To a stirring solution of (2S-FNL-3) (500 mg (crude), 2.20 mmol) in CH$_2$Cl$_2$ (10 mL) was added TEA (1 mL, 7.70 mmol) followed by isobutyryl chloride (256 mg, 2.42 mmol) at 0° C. and stirred for 16 h at RT. After consumption of the starting material (by TLC), the reaction mixture was diluted with water (10 mL) and extracted with CH$_2$Cl$_2$ (2×30 mL). The combined organic layer was washed with citric acid solution (2×30 mL). The organic layer was dried over anhydrous Na$_2$SO$_4$, filtered and concentrated under reduced pressure. Obtained crude material was purified by silica gel column chromatography eluting 2% MeOH/DCM to afford the two diastereomers of (2S-FNL-4) (100 mg, 15.2%) as white solid. The two 2S-FNL-4 diastereomers were separated by repetitive silica gel column chromatography to provide NYX-2925.

$^1$H-NMR: (500 MHz, DMSO-d$_6$): δ 7.63 (br s, ex with D20, 1H), 7.18 (br s, ex with D20, 1H), 4.77 (d, J=4.0 Hz, ex with D$_2$O, 1H), 4.04-4.00 (m, 1H), 3.95 (d, J=6.5 Hz, 1H), 3.76 (d, J=5.5 Hz, 1H), 3.66-3.63 (m, 1H), 3.53 (q, J=8.0 Hz, 1H), 3.39 (d, J=5.5 Hz, 1H), 2.72 (septet, J=6.5 Hz, 1H), 2.14-2.05 (m, 2H), 1.92-1.86 (m, 2H), 1.10 (d, J=6.0 Hz, 3H), 1.02 (d, J=6.5 Hz, 3H), 0.99 (d, J=6.5 Hz, 3H);

Mass (ESI): 298.4 [M$^+$+1].

Example 2: Form MH

Crystalline, monohydrate Form MH of (2S,3R)-3-hydroxy-2-((R)-5-isobutyryl-1-oxo-2,5-diazaspiro[3.4]octan-2-yl)butanamide was prepared as follows. Saturated solutions of 3-hydroxy-2-(5-isobutyryl-1-oxo-2,5-diazaspiro [3.4]octan-2-yl)butanamide were prepared in pH 2, pH 3, pH 5, pH 7, and pH 8 buffers and were stirred at 25° C. Aliquots were taken after 1 day, 4 days, and 7 days and centrifuged at 12,500 rpm for 15 minutes. The supernatant was analyzed for sample concentration by HPLC, and the residual solids were analyzed by XRPD after 1 day, 4 days, and 7 days. HPLC analysis of each sample indicated that for all instances the material was stable across pH ranges of 2-8 at saturated concentrations of about 50 mg/mL after 7 days. XRPD analysis of each sample indicated that for all instances the material was crystalline with a pattern consistent with the monohydrate Form MH.

Crystalline, monohydrate Form MH of (2S,3R)-3-hydroxy-2-((R)-5-isobutyryl-1-oxo-2,5-diazaspiro[3.4]octan-2-yl)butanamide was also prepared as follows. A 30 gram sample of anhydrous 3-hydroxy-2-(5-isobutyryl-1-oxo-2,5-diazaspiro[3.4]octan-2-yl)butanamide was hydrated by contact with an atmosphere of 80% relative aqueous humidity over 7 days. XRPD analysis of aliquots taken at 5 hours, 24 hours, 4 days, and seven days indicated that conversion of the anhydrous form to the monohydrate Form MH was mostly complete after 4 days, and totally complete after 7 days. XRPD analysis of the sample after 7 days indicated that the material was crystalline with a pattern consistent with the monohydrate Form MH.

Crystalline, monohydrate Form MH was obtained by crystallization of 3-hydroxy-2-(5-isobutyryl-1-oxo-2,5-diazaspiro[3.4]octan-2-yl)butanamide from aqueous solutions under both slow and fast cooling conditions.

The XRPD pattern for crystalline, monohydrate Form MH of (2S,3R)-3-hydroxy-2-((R)-5-isobutyryl-1-oxo-2,5-diazaspiro[3.4]octan-2-yl)butanamide is shown in FIG. 1. Characteristic peaks include one or more of the peaks shown in Table 1, below.

TABLE 1

| Peak Pos. [°2θ] | Peak Height [Cts] | Rel. Int. [%] |
|---|---|---|
| 9.70 | 455 | 1.7 |
| 10.82 | 27534 | 100.0 |
| 11.17 | 337 | 1.2 |
| 13.42 | 18733 | 68.0 |
| 14.52 | 1931 | 7.0 |
| 15.89 | 1682 | 6.1 |
| 16.56 | 3184 | 11.6 |
| 16.85 | 2551 | 9.3 |
| 18.42 | 10726 | 39.0 |
| 18.58 | 3654 | 13.3 |
| 19.25 | 1610 | 5.9 |
| 19.46 | 2077 | 7.5 |
| 20.23 | 141 | 0.5 |
| 20.80 | 7202 | 26.2 |
| 20.99 | 8223 | 29.9 |
| 21.59 | 3288 | 11.9 |
| 22.44 | 694 | 2.5 |
| 23.15 | 2741 | 10.0 |
| 23.83 | 544 | 2.0 |
| 24.32 | 987 | 3.6 |
| 24.53 | 1081 | 3.9 |
| 25.01 | 1355 | 4.9 |
| 25.17 | 6121 | 22.2 |
| 25.61 | 3716 | 13.5 |
| 26.32 | 558 | 2.0 |
| 27.02 | 2402 | 8.7 |
| 28.10 | 1025 | 3.7 |
| 28.58 | 311 | 1.1 |
| 29.18 | 1423 | 5.2 |
| 29.36 | 638 | 2.3 |
| 29.69 | 3338 | 12.1 |
| 29.86 | 2760 | 10.0 |
| 30.24 | 376 | 1.4 |
| 30.38 | 874 | 3.2 |
| 30.79 | 479 | 1.7 |
| 30.98 | 490 | 1.8 |
| 31.30 | 273 | 1.0 |
| 32.08 | 766 | 2.8 |
| 32.53 | 1190 | 4.3 |
| 32.86 | 2074 | 7.5 |
| 33.46 | 196 | 0.7 |
| 33.83 | 1398 | 5.1 |
| 34.37 | 140 | 0.5 |
| 34.92 | 1155 | 4.2 |
| 35.37 | 623 | 2.3 |
| 36.18 | 443 | 1.6 |
| 36.67 | 115 | 0.4 |
| 37.31 | 513 | 1.9 |
| 37.62 | 2371 | 8.6 |
| 38.15 | 380 | 1.4 |
| 39.06 | 314 | 1.1 |
| 39.79 | 428 | 1.6 |

Crystalline, monohydrate Form MH of NYX-2925 is characterized by a Fourier Transform-Raman (FT-Raman) spectrum having at least one or more characteristic aliphatic C—H stretching vibrations between about 2800 cm$^{-1}$ to about 3200 cm$^{-1}$ as well as at least one or more characteristic amide group bands between about 1620 cm$^{-1}$ to about 1740 cm$^{-1}$.

Figure 2:
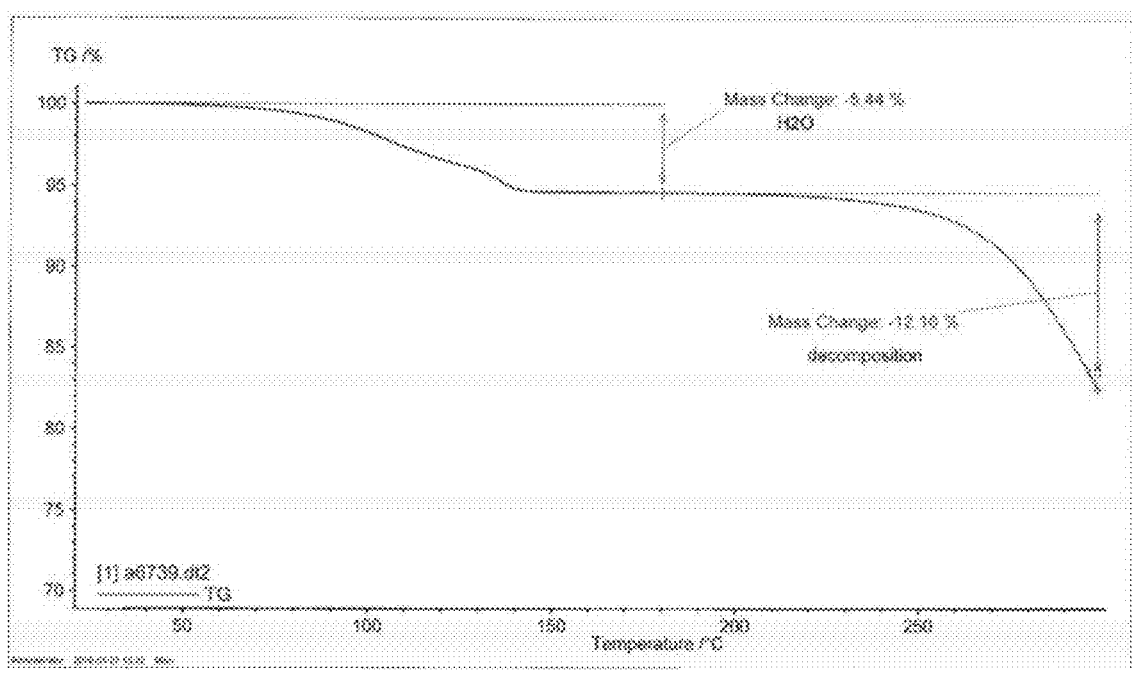
FIG. 2 depicts the TG-FTIR thermogram of Form MH.

FIG. 2 depicts the Thermogravimetric Fourier Transform Infrared (TG-FTIR) thermogram of crystalline, monohydrate Form MH of NYX-2925. As shown in FIG. 2, crystalline, monohydrate Form MH of NYX-2925 is characterized by a TG-FTIR absorption spectrum showing weight loss of about 5.4% in the temperature range of 40-150° C., and a chemical decomposition event starting above 210° C. The rate of heating is 10° C. per minute.

Figure 3:
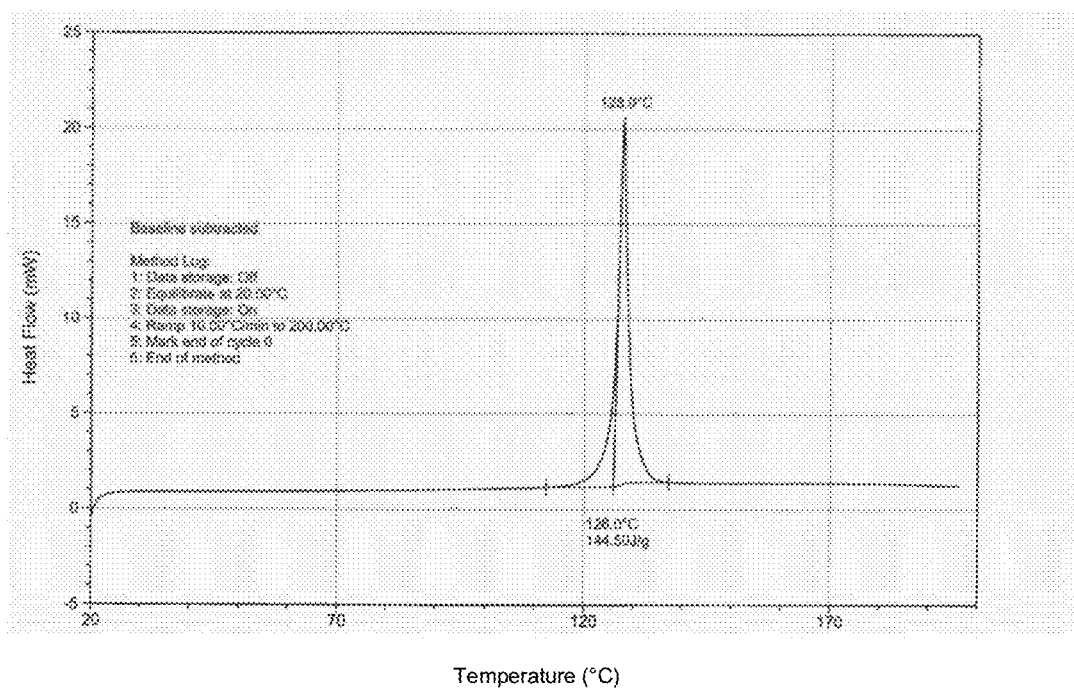
FIG. 3 depicts the characterization of Form MH by differential scanning calorimetry (DSC).

FIG. 3 depicts the differential scanning calorimetry (DSC) profile of crystalline, monohydrate Form MH of NYX-2925. As shown in FIG. 3, crystalline, monohydrate Form MH of NYX-2925 is characterized by a melting point of about 126° C. and a melting enthalpy of about 145 J/g, and is characterized by an sharp endothermic peak in the DSC profile at about 128° C. The rate of heating is 10° C. per minute.

Figure 4:
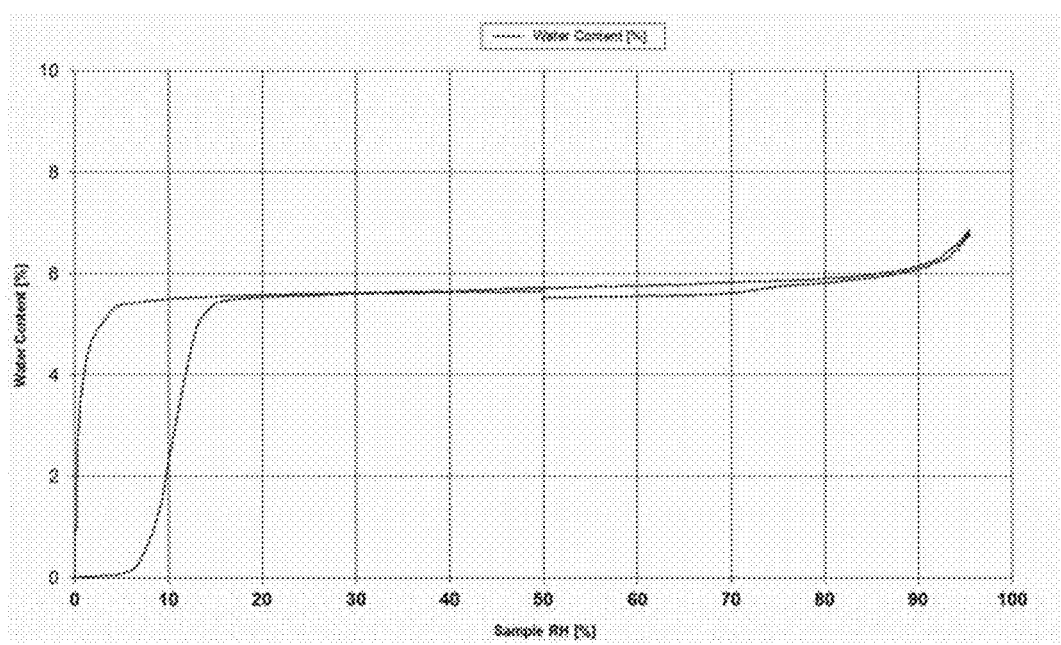
FIG. 4 depicts the dynamic vapor sorption (DVS) profile for Form MH.

FIG. 4 depicts the dynamic sorption vapor (DVS) profile of crystalline, monohydrate Form MH of NYX-2925. As shown in FIG. 4, the DVS profile of crystalline, monohydrate Form MH of NYX-2925 shows continuous uptake of about 1.5 wt. % water from about 50% to about 95% relative humidity, which mainly takes place above 90% relative. This is a fully reversible process and the sample loses this water when decreasing the relative humidity with a negligible hysteresis. At low relative humidity there is the release and uptake of about 5.5 wt. % in the range of about 0% to about 15% relative humidity with about 10% relative humidity hysteresis. The monohydrate Form MH of NYX-2925 retains about 5.7 weight % water content, corresponding to the stoichiometric water content of the, monohydrate, over the range of about 10% to about 80% relative humidity with less than 0.5 wt. % change. There is minimal water uptake above 80% relative humidity and about 1 weight % gain in the 90% to 95% relative humidity range. As shown in FIG. 4, crystalline, monohydrate Form MI-1 of NYX-2925 reversibly loses and takes up its entire water content below about 10% relative humidity.

Single crystals of a NYX-2925 were grown and analyzed by single crystal X-ray analysis. The crystal displayed an orthorhombic system with the unit cell parameters and other crystallographic experimental details shown in Table 2, below.

TABLE 2

| | |
|---|---|
| Empirical formula | $C_{14}H_{23}N_3O_5$ |
| Formula weight | 313.35 |
| Temperature | 296(2)K |
| Wavelength | 0.71073 Å |
| Crystal system | Orthorhombic |
| Space group | $P\,2_1\,2_1\,2_1$ |
| Unit cell dimensions | a = 9.5470(7) Å, α = 90° |
| | b = 11.1504(8) Å, β = 90° |
| | c = 15.8414(11) Å, γ = 90° |
| Volume | 1686.4(2) Å$^3$ |
| Z | 4 |
| Density (calculated) | 1.234 Mg/m$^3$ |
| Absorption coefficient | 0.094 mm$^{-1}$ |
| F(000) | 672 |
| Crystal size | 0.310 × 0.228 × 0.127 mm$^3$ |
| Theta range for data collection | 2.809 to 28.417° |

TABLE 2-continued

| | |
|---|---|
| Index ranges | −12 <= h <= 12, −14 <= k <= 14, −21 <= l <= 21 |
| Reflections collected | 69409 |
| Independent reflections | 4229 [R(int) = 0.0732] |
| Completeness to theta = 25.242° | 99.8% |
| Refinement method | Full-matrix least-squares on F$^2$ |
| Data/restraints/parameters | 4229/0/203 |
| Goodness-of-fit on F$^2$ | 0.917 |
| Final R indices [I > 2sigma(I)] | R1 = 0.0500, wR2 = 0.1275 |
| R indices (all data) | R1 = 0.0828, wR2 = 0.1486 |
| Absolute structure parameter | −0.3(4) |
| Extinction coefficient | n/a |
| Largest diff. peak and hole | 0.390 and −0.203 e. Å$^{-3}$ |

Figure 5:
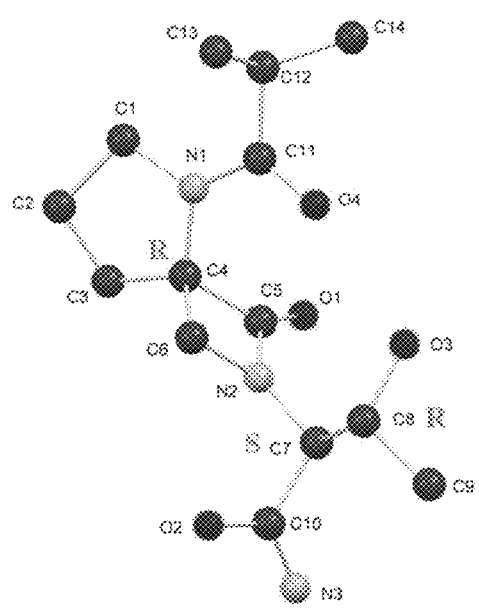
FIG. 5 depicts the molecular structure of Form MH as determined by single X-ray crystallography.

The X-ray crystal structure obtain from the single crystal determination of crystalline, monohydrate Form MH of NYX-2925 is shown in FIG. 5, with hydrogen atoms omitted for clarity. As shown in FIG. 5, the stereogenic centers labelled C4, C7, and C8 were demonstrated to have the configuration of (R), (S), and (R), respectively.

Atomic coordinates (×10$^4$) and equivalent isotropic displacement parameters (Å$^2$×10$^3$) are shown in Table 3, below. U(eq) is defined as one third of the trace of the orthogonalized U$^{ij}$ tensor.

TABLE 3

| Atom | x | y | z | U(eq) |
|---|---|---|---|---|
| O(1) | 6262(2) | 2316(2) | 7688(1) | 41(1) |
| O(2) | 4996(3) | −868(2) 9 | 729(2) | 56(1) |
| O(3) | 3711(3) | 2845(2) | 9544(1) | 48(1) |
| O(4) | 2765(2) | 2861(2) | 7907(1) | 48(1) |
| N(1) | 3237(3) | 1639(2) | 6814(2) | 37(1) |
| N(2) | 4933(2) | 1023(2) | 8541(1) | 31(1) |
| N(3) | 7008(3) | −60(2) | 10167(2) | 43(1) |
| C(1) | 3101(4) | 1204(3) | 5937(2) | 52(1) |
| C(2) | 3775(5) | −31(4) | 5980(3) | 72(1) |
| C(3) | 4862(4) | 68(3) | 6646(2) | 48(1) |
| C(4) | 4241(3) | 925(3) | 7295(2) | 34(1) |
| C(5) | 5333(3) | 1598(2) | 7828(2) | 30(1) |
| C(6) | 3750(4) | 380(3) | 8151(2) | 39(1) |
| C(7) | 5352(3) | 1198(2) | 9411(2) | 29(1) |
| C(8) | 4153(3) | 1753(3) | 9918(2) | 38(1) |
| C(9) | 4570(4) | 2039(4) | 10819(2) | 59(1) |
| C(10) | 5779(3) | −16(3) | 9790(2) | 32(1) |
| C(11) | 2560(3) | 2574(3) | 7163(2) | 37(1) |
| C(12) | 1500(4) | 3241(3) | 6634(2) | 50(1) |
| C(13) | 95(4) | 2592(5) | 6700(3) | 77(1) |
| C(14) | 1386(6) | 4539(4) | 6917(3) | 75(1) |
| O(5) | 6862(3) | 2372(2) | 5878(2) | 54(1) |

Bond lengths (Å) and bond angles (°) are shown in Table 4, below.

TABLE 4

| | | | |
|---|---|---|---|
| O(1)—C(5) | 1.215(3) | C(4)—C(5) | 1.537(4) |
| O(2)—C(10) | 1.214(4) | C(4)—C(6) | 1.557(4) |
| O(3)—C(8) | 1.419(4) | C(6)—H(6A) | 0.9700 |
| O(3)—H(3) | 0.8200 | C(6)—H(6B) | 0.9700 |
| O(4)—C(11) | 1.237(4) | C(7)—C(8) | 1.529(4) |
| N(1)—C(11) | 1.345(4) | C(7)—C(10) | 1.535(4) |
| N(1)—C(4) | 1.460(4) | C(7)—H(7) | 0.9800 |
| N(1)—C(1) | 1.479(4) | C(8)—C(9) | 1.515(4) |
| N(2)—C(5) | 1.354(3) | C(8)—H(8) | 0.9800 |
| N(2)—C(7) | 1.448(3) | C(9)—H(9A) | 0.9600 |
| N(2)—C(6) | 1.474(4) | C(9)—H(9B) | 0.9600 |
| N(3)—C(10) | 1.318(4) | C(9)—H(9C) | 0.9600 |
| N(3)—H(3A) | 0.8600 | C(11)—C(12) | 1.510(4) |
| N(3)—H(3B) | 0.8600 | C(12)—C(14) | 1.519(6) |
| C(1)—C(2) | 1.521(6) | C(12)—C(13) | 1.528(6) |
| C(1)—H(1A) | 0.9700 | C(12)—H(12) | 0.9800 |
| C(1)—H(1B) | 0.9700 | C(13)—H(13A) | 0.9600 |

TABLE 4-continued

| | | | |
|---|---|---|---|
| C(2)—C(3) | 1.484(5) | C(13)—H(13B) | 0.9600 |
| C(2)—H(2A) | 0.9700 | C(13)—H(13C) | 0.9600 |
| C(2)—H(2B) | 0.9700 | C(14)—H(14A) | 0.9600 |
| C(3)—C(4) | 1.523(4) | C(14)—H(14B) | 0.9600 |
| C(3)—H(3C) | 0.9700 | C(14)—H(14C) | 0.9600 |
| C(3)—H(3D) | 0.9700 | C(8)—O(3)—H(3) | 109.5 |
| C(11)—N(1)—C(4) | 121.6(2) | H(3C)—C(3)—H(3D) | 108.9 |
| C(11)—N(1)—C(1) | 126.7(3) | N(1)—C(4)—C(3) | 104.2(2) |
| C(4)—N(1)—C(1) | 111.7(3) | N(1)—C(4)—C(5) | 117.7(2) |
| C(5)—N(2)—C(7) | 130.7(2) | C(3)—C(4)—C(5) | 114.4(3) |
| C(5)—N(2)—C(6) | 95.5(2) | N(1)—C(4)—C(6) | 117.9(3) |
| C(7)—N(2)—C(6) | 132.6(2) | C(3)—C(4)—C(6) | 117.4(3) |
| C(10)—N(3)—H(3A) | 120.0 | C(5)—C(4)—C(6) | 85.2(2) |
| C(10)—N(3)—H(3B) | 120.0 | O(1)—C(5)—N(2) | 132.1(3) |
| H(3A)—N(3)—H(3B) | 120.0 | O(1)—C(5)—C(4) | 135.8(3) |
| N(1)—C(1)—C(2) | 102.5(3) | N(2)—C(5)—C(4) | 92.0(2) |
| N(1)—C(1)—H(1A) | 111.3 | N(2)—C(6)—C(4) | 86.8(2) |
| C(2)—C(1)—H(1A) | 111.3 | N(2)—C(6)—H(6A) | 114.2 |
| N(1)—C(1)—H(1B) | 111.3 | C(4)—C(6)—H(6A) | 114.2 |
| C(2)—C(1)—H(1B) | 111.3 | N(2)—C(6)—H(6B) | 114.2 |
| H(1A)—C(1)—H(1B) | 109.2 | C(4)—C(6)—H(6B) | 114.2 |
| C(3)—C(2)—C(1) | 105.1(3) | H(6A)—C(6)—H(6B) | 111.3 |
| C(3)—C(2)—H(2A) | 110.7 | N(2)—C(7)—C(8) | 110.3(2) |
| C(1)—C(2)—H(2A) | 110.7 | N(2)—C(7)—C(10) | 109.1(2) |
| C(3)—C(2)—H(2B) | 110.7 | C(8)—C(7)—C(10) | 110.5(2) |
| C(1)—C(2)—H(2B) | 110.7 | N(2)—C(7)—H(7) | 109.0 |
| H(2A)—C(2)—H(2B) | 108.8 | C(8)—C(7)—H(7) | 109.0 |
| C(2)—C(3)—C(4) | 104.7(3) | C(10)—C(7)—H(7) | 109.0 |
| C(2)—C(3)—H(3C) | 110.8 | O(3)—C(8)—C(9) | 106.9(3) |
| C(4)—C(3)—H(3C) | 110.8 | O(3)—C(8)—C(7) | 110.5(2) |
| C(2)—C(3)—H(3D) | 110.8 | C(9)—C(8)—C(7) | 112.5(3) |
| C(4)—C(3)—H(3D) | 110.8 | O(3)—C(8)—H(8) | 108.9 |
| C(9)—C(8)—H(8) | 108.9 | C(14)—C(12)—C(13) | 111.6(4) |
| C(7)—C(8)—H(8) | 108.9 | C(11)—C(12)—H(12) | 108.7 |
| C(8)—C(9)—H(9A) | 109.5 | C(14)—C(12)—H(12) | 108.7 |
| C(8)—C(9)—H(9B) | 109.5 | C(13)—C(12)—H(12) | 108.7 |
| H(9A)—C(9)—H(9B) | 109.5 | C(12)—C(13)—H(13A) | 109.5 |
| C(8)—C(9)—H(9C) | 109.5 | C(12)—C(13)—H(13B) | 109.5 |
| H(9A)—C(9)—H(9C) | 109.5 | H(13A)—C(13)—H(13B) | 109.5 |
| H(9B)—C(9)—H(9C) | 109.5 | C(12)—C(13)—H(13C) | 109.5 |
| O(2)—C(10)—N(3) | 123.7(3) | H(13A)—C(13)—H(13C) | 109.5 |
| O(2)—C(10)—C(7) | 119.7(2) | H(13B)—C(13)—H(13C) | 109.5 |
| N(3)—C(10)—C(7) | 116.5(2) | C(12)—C(14)—H(14A) | 109.5 |
| O(4)—C(11)—N(1) | 121.0(3) | C(12)—C(14)—H(14B) | 109.5 |
| O(4)—C(11)—C(12) | 120.5(3) | H(14A)—C(14)—H(14B) | 109.5 |
| N(1)—C(11)—C(12) | 118.5(3) | C(12)—C(14)—H(14C) | 109.5 |
| C(11)—C(12)—C(14) | 110.7(3) | H(14A)—C(14)—H(14C) | 109.5 |
| C(11)—C(12)—C(13) | 108.5(3) | H(14B)—C(14)—H(14C) | 109.5 |

Anisotropic displacement parameters (Å$^2$×10$^3$) are shown in Table 5, below. The anisotropic displacement factor exponent may be expressed in the form: $-2\pi^2[h^2a^{*2}U^{11}+ \ldots +2\,h\,k\,a^*b^*U^{12}]$.

TABLE 5

| Atom | U$^{11}$ | U$^{22}$ | U$^{33}$ | U$^{23}$ | U$^{13}$ | U$^{12}$ |
|---|---|---|---|---|---|---|
| O(1) | 46(1) | 41(1) | 37(1) | 6(1) | 3(1) | −8(1) |
| O(2) | 67(2) | 39(1) | 63(2) | 16(1) | −28(1) | −19(1) |
| O(3) | 62(1) | 45(1) | 37(1) | −4(1) | −4(1) | 20(1) |
| O(4) | 54(1) | 53(1) | 36(1) | −4(1) | −12(1) | 13(1) |
| N(1) | 46(1) | 38(1) | 27(1) | 1(1) | −9(1) | 1(1) |
| N(2) | 36(1) | 30(1) | 26(1) | 2(1) | −4(1) | −3(1) |
| N(3) | 47(2) | 35(1) | 46(2) | 4(1) | −17(1) | 2(1) |
| C(1) | 64(2) | 63(2) | 30(2) | −13(2) | −3(2) | −1(2) |
| C(2) | 87(3) | 74(3) | 56(2) | −27(2) | −24(2) | 17(3) |
| C(3) | 67(2) | 38(2) | 38(2) | −6(2) | −4(2) | 6(2) |
| C(4) | 43(2) | 29(1) | 30(1) | 3(1) | −4(1) | −2(1) |
| C(5) | 36(1) | 27(1) | 27(1) | 3(1) | 1(1) | 4(1) |
| C(6) | 47(2) | 36(1) | 33(1) | 6(1) | −10(1) | −10(1) |
| C(7) | 31(1) | 29(1) | 26(1) | 3(1) | −5(1) | −3(1) |
| C(8) | 41(2) | 43(2) | 31(1) | 1(1) | 0(1) | 1(1) |
| C(9) | 68(2) | 76(3) | 33(2) | −8(2) | −3(2) | 18(2) |
| C(10) | 41(2) | 31(1) | 25(1) | 2(1) | −5(1) | −3(1) |
| C(11) | 37(2) | 42(2) | 33(1) | 8(1) | −6(1) | −3(1) |

TABLE 5-continued

| Atom | U$^{11}$ | U$^{22}$ | U$^{33}$ | U$^{23}$ | U$^{13}$ | U$^{12}$ |
|---|---|---|---|---|---|---|
| C(12) | 47(2) | 63(2) | 40(2) | 12(2) | −7(1) | 14(2) |
| C(13) | 45(2) | 112(4) | 74(3) | −2(3) | −12(2) | −1(2) |
| C(14) | 82(3) | 62(3) | 79(3) | 14(2) | −9(3) | 24(2) |
| O(5) | 63(1) | 53(1) | 47(1) | 3(1) | 11(1) | 18(1) |

Hydrogen bond distances (Å) and angles (°) are shown in Table 6, below.

TABLE 6

| D—H . . . A | d(D—H) | d(H . . . A) | d(D . . . A) | <(DHA) |
|---|---|---|---|---|
| C(3)—H(3C) . . . O(5) | 0.97 | 2.61 | 3.425(5) | 141.9 |
| O(3)—H(3) . . . O(4) | 0.82 | 1.95 | 2.746(3) | 165.2 |
| C(3)—H(3C) . . . O(5) | 0.97 | 2.61 | 3.425(5) | 141.9 |
| O(3)—H(3) . . . O(4) | 0.82 | 1.95 | 2.746(3) | 165.2 |
| C(3)—H(3C) . . . O(5) | 0.97 | 2.61 | 3.425(5) | 141.9 |
| C(3)—H(3C) . . . O(5) | 0.97 | 2.61 | 3.425(5) | 141.9 |
| C(3)—H(3C) . . . O(5) | 0.97 | 2.61 | 3.425(5) | 141.9 |
| O(3)—H(3) . . . O(4) | 0.82 | 1.95 | 2.746(3) | 165.2 |
| O(3)—H(3) . . . N(2) | 0.82 | 2.50 | 2.830(3) | 105.6 |
| C(3)—H(3C) . . . O(5) | 0.97 | 2.61 | 3.425(5) | 141.9 |
| O(3)—H(3) . . . O(4) | 0.82 | 1.95 | 2.746(3) | 165.2 |

TABLE 6-continued

| D—H . . . A | d(D—H) | d(H . . . A) | d(D . . . A) | <(DHA) |
|---|---|---|---|---|
| O(3)—H(3) . . . N(2) | 0.82 | 2.50 | 2.830(3) | 105.6 |
| O(3)—H(3) . . . N(2) | 0.82 | 2.50 | 2.830(3) | 105.6 |
| O(3)—H(3) . . . O(4) | 0.82 | 1.95 | 2.746(3) | 165.2 |
| C(3)—H(3C) . . . O(5) | 0.97 | 2.61 | 3.425(5) | 141.9 |
| O(3)—H(3) . . . O(4) | 0.82 | 1.95 | 2.746(3) | 165.2 |
| C(3)—H(3C) . . . O(5) | 0.97 | 2.61 | 3.425(5) | 141.9 |
| C(3)—H(3C) . . . O(5) | 0.97 | 2.61 | 3.425(5) | 141.9 |

Torsion angles (°) are shown in Table 7, below.

TABLE 7

| | | | |
|---|---|---|---|
| C(11)—N(1)—C(1)—C(2) | −165.1(3) | C(7)—N(2)—C(6)—C(4) | 173.0(3) |
| C(4)—N(1)—C(1)—C(2) | 15.4(4) | N(1)—C(4)—C(6)—N(2) | −123.2(3) |
| N(1)—C(1)—C(2)—C(3) | −30.6(4) | C(3)—C(4)—C(6)—N(2) | 110.9(3) |
| C(1)—C(2)—C(3)—C(4) | 34.7(4) | C(5)—C(4)—C(6)—N(2) | −4.2(2) |
| C(11)—N(1)—C(4)—C(3) | −174.1(3) | C(5)—N(2)—C(7)—C(8) | 109.0(3) |
| C(1)—N(1)—C(4)—C(3) | 5.4(3) | C(6)—N(2)—C(7)—C(8) | −55.5(4) |
| C(11)—N(1)—C(4)—C(5) | −46.2(4) | C(5)—N(2)—C(7)—C(10) | −129.4(3) |
| C(1)—N(1)—C(4)—C(5) | 133.4(3) | C(6)—N(2)—C(7)—C(10) | 66.1(4) |
| C(11)—N(1)—C(4)—C(6) | 53.8(4) | N(2)—C(7)—C(8)—O(3) | −56.4(3) |
| C(1)—N(1)—C(4)—C(6) | −126.7(3) | C(10)—C(7)—C(8)—O(3) | −177.1(2) |
| C(2)—C(3)—C(4)—N(1) | −24.7(4) | N(2)—C(7)—C(8)—C(9) | −175.8(3) |
| C(2)—C(3)—C(4)—C(5) | −154.7(3) | C(10)—C(7)—C(8)—C(9) | 63.5(3) |
| C(2)—C(3)—C(4)—C(6) | 107.8(3) | N(2)—C(7)—C(10)—O(2) | −51.3(4) |
| C(7)—N(2)—C(5)—O(1) | 10.1(5) | C(8)—C(7)—C(10)—O(2) | 70.2(3) |
| C(6)—N(2)—C(5)—O(1) | 178.7(3) | N(2)—C(7)—C(10)—N(3) | 128.5(3) |
| C(7)—N(2)—C(5)—C(4) | −173.4(3) | C(8)—C(7)—C(10)—N(3) | −110.0(3) |
| C(6)—N(2)—C(5)—C(4) | −4.8(2) | C(4)—N(1)—C(11)—O(4) | −0.2(4) |
| N(1)—C(4)—C(5)—O(1) | −60.0(4) | C(1)—N(1)—C(11)—O(4) | −179.6(3) |
| C(3)—C(4)—C(5)—O(1) | 62.9(4) | C(4)—N(1)—C(11)—C(12) | −177.9(3) |
| C(6)—C(4)—C(5)—O(1) | −179.2(3) | C(1)—N(1)—C(11)—C(12) | 2.7(5) |
| N(1)—C(4)—C(5)—N(2) | 123.7(3) | O(4)—C(11)—C(12)—C(14) | 30.4(5) |
| C(3)—C(4)—C(5)—N(2) | −113.4(3) | N(1)—C(11)—C(12)—C(14) | −151.9(3) |
| C(6)—C(4)—C(5)—N(2) | 4.6(2) | O(4)—C(11)—C(12)—C(13) | −92.4(4) |
| C(5)—N(2)—C(6)—C(4) | 4.8(2) | N(1)—C(11)—C(12)—C(13) | 85.3(4) |

Figure 6:
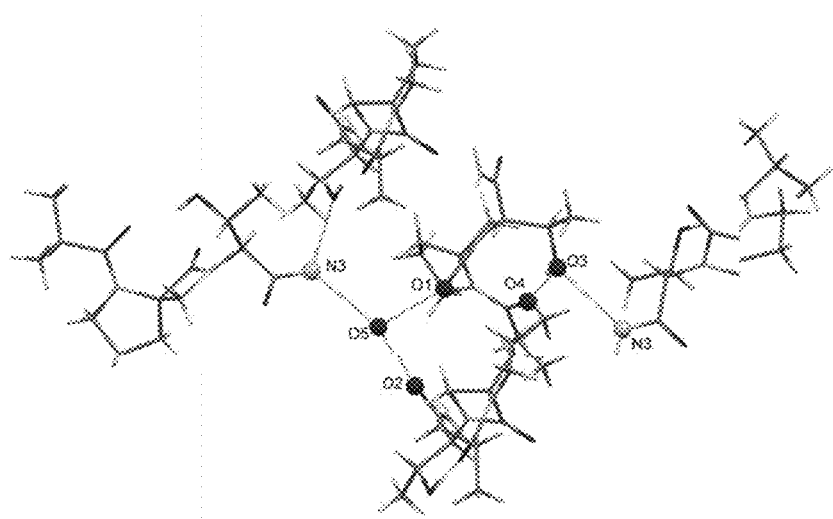
FIG. 6 depicts the hydrogen bonding network in the crystal of Form MH.

FIG. 6 depicts hydrogen bonding interactions in the crystal. As shown in FIG. 6, intermolecular (NH . . . O, OH . . . O) and intramolecular hydrogen bonding (OH . . . O) play a role in stabilizing the molecules in the crystal. The water molecule (O5) in the lattice also plays an important role in forming a complex inside the crystal via NH . . . O and OH . . . O hydrogen bonds.

The approximate solubility of crystalline, monohydrate Form MH of NYX-2925 across a range of solvents and solvent mixtures (expressed in volume ratios measured at about 22° C.) is provided in Table 8, below.

TABLE 8

| Solvent or Solvent Mixture | Solubility S (mg/mL) |
|---|---|
| acetone | 57 < S < 76 |
| aniline | 200 < S |
| anisole | S~3 |
| cyclohexane | S < 1 |
| dichloromethane | 55 < S < 73 |
| diisopropyl ether | S < 1 |
| 1,4-dioxane | 28 < S < 31 |
| dimethylformamide | 200 < S |
| dimethyl sulfoxide | 200 < S |
| ethyl acetate | 13 < S < 15 |
| ethanol | 200 < S |
| heptane | S < 1 |
| acetonitrile | 118 < S < 230 |
| methanol | 200 < S |
| methyl ethyl ketone | 32 < S < 38 |
| isopropyl acetate | 5 < S < 6 |
| isopropanol | 45 < S < 60 |
| tert-butyl methyl ether | S < 1 |
| tetrahydrofuran | 31 < S < 36 |

TABLE 8-continued

| Solvent or Solvent Mixture | Solubility S (mg/mL) |
|---|---|
| toluene | S < 1 |
| triethylamine | S < 1 |
| water | 26 < S <30 |
| 1/1 dichloromethane/methanol | 200 < S |
| 10/1 ethyl acetate/ethanol | 32 < S < 39 |
| ethyl acetate saturated with water | 6 < S < 8 |
| 1/1 ethanol/water | 69 < S < 103 |
| 1/1 methanol/water | 200 < S |

TABLE 8-continued

| Solvent or Solvent Mixture | Solubility S (mg/mL) |
|---|---|
| 1/1 isopropanol/water | 71 < S < 107 |
| 10/1 isopropanol/water | 36 < S < 41 |
| tert-butyl methyl ether saturated with water | S < 1 |

Form MH of NYX-2925 has a solubility in an aqueous solvent (e.g., an aqueous solution that may include a buffer) with a pH of about 2 of about 54.1 mg/mL at ca. 25° C. after about 1 day, about 53.5 mg/mL after about 4 days, and about 53.5 mg/mL after about 7 days. Form MH has a solubility in an aqueous solvent with a pH of about 3 of about 54.2 mg/mL at ca. 25° C. after about 1 day, about 53.2 mg/mL after about 4 days, and about 52.4 mg/mL after about 7 days. Form MH has a solubility in an aqueous solvent with a pH of about 5 of about 52.5 mg/mL at ca. 25° C. after about 1 day, about 53.2 mg/mL after about 4 days, and about 52.4 mg/mL after about 7 days. Form MH has a solubility in an aqueous solvent with a pH of about 7 of about 52.6 mg/mL at ca. 25° C. after about 1 day, about 53.0 mg/mL after about 4 days, and about 52.3 mg/mL after about 7 days. Form MH has a solubility in an aqueous solvent with a pH of about 8 of about 52.7 mg/mL at ca. 25° C. after about 1 day, about 51.6 mg/mL after about 4 days, and about 52.6 mg/mL after about 7 days.

Example 3: Form A

Crystalline, anhydrous Form A material of 3-hydroxy-2-(5-isobutyryl-1-oxo-2,5-diazaspiro[3.4]octan-2-yl)butanamide was prepared by drying crystalline, monohydrate Form MH. A 5 gram sample of crystalline, monohydrate Form MH of NYX-2925 was dried at 50° C. under a stream of dry $N_2$ for 23 h, resulting in a decrease in mass of 5.6%. XRPD analysis indicated that the material obtained was crystalline with a pattern consistent with anhydrous Form A.

Alternatively, a 0.5 gram sample of crystalline, monohydrate Form A of 3-hydroxy-2-(5-isobutyryl-1-oxo-2,5-diazaspiro[3.4]octan-2-yl)butanamide was dried at 70° C. under a dry stream of $N_2$ for 1 h, then at 130° C. for 30 min. XRPD analysis indicated that the material obtained was crystalline with a pattern consistent with anhydrous Form A.

Crystalline, anhydrous Form A material was also prepared by drying the monohydrate Form MH at room temperature in an atmosphere of less than 5% relative humidity.

Crystalline, anhydrous Form A material was further prepared by crystallization of 3-hydroxy-2-(5-isobutyryl-1-oxo-2,5-diazaspiro[3.4]octan-2-yl)butanamide from dry, non-aqueous solutions by slow cooling or slow evaporation. A 200 mg sample of 3-hydroxy-2-(5-isobutyryl-1-oxo-2,5-diazaspiro[3.4]octan-2-yl)butanamide was dissolved in 0.5 mL of dichloromethane (previously dried over molecular sieves with a pore size of 4 Å) at 60° C. (under pressure) and cooled to 0° C. with magnetic stirring. After 30 minutes, the solution was heated to about 40° C. and about half of the solvent was evaporated. The solution was cooled again to 0° C. for 1 hour, brought to room temperature, and stirred at room temperature over two days with slow and complete evaporation of solvent. XRPD analysis indicated that the material obtained was crystalline with a pattern consistent with anhydrous Form A.

The above results indicate that anhydrous Form A is the thermodynamically favored anhydrous polymorphic form under conditions of slow cooling and/or slow evaporation.

Crystalline, anhydrous Form A material readily converts to the monohydrate Form MH in the solid phase within 3 days under ambient temperature and in an atmosphere of greater than 5% relative humidity, indicating that monohydrate Form MI-1 is more stable than anhydrous Form A under conditions of ambient temperature and humidity.

Form A of 3-hydroxy-2-(5-isobutyryl-1-oxo-2,5-diazaspiro[3.4]octan-2-yl)butanamide has a solubility in isopropyl acetate of about 8 mg/mL after 10 minutes, 1 hour, and 6 hours at room temperature.

Characteristic peaks in the XRPD pattern for crystalline, anhydrous Form A of 3-hydroxy-2-(5-isobutyryl-1-oxo-2,5-diazaspiro[3.4]octan-2-yl)butanamide include one or more of the peaks shown in Table 9, below.

TABLE 9

| Peak Pos. [°2θ] | Peak Height [Cts] | Rel. Int. [%] |
| --- | --- | --- |
| 9.70 | 1882 | 14.6 |
| 10.83 | 3108 | 24.1 |
| 11.34 | 11816 | 91.5 |
| 13.44 | 2396 | 18.6 |
| 13.89 | 12911 | 100.0 |
| 14.52 | 293 | 2.3 |
| 14.81 | 1452 | 11.3 |
| 15.52 | 423 | 3.3 |
| 16.02 | 1145 | 8.9 |
| 16.60 | 468 | 3.6 |
| 16.86 | 2695 | 20.9 |
| 18.37 | 1864 | 14.4 |
| 18.88 | 6652 | 51.5 |
| 19.46 | 2194 | 17.0 |
| 19.91 | 1011 | 7.8 |
| 20.89 | 4574 | 35.4 |

TABLE 9-continued

| Peak Pos. [°2θ] | Peak Height [Cts] | Rel. Int. [%] |
| --- | --- | --- |
| 21.52 | 799 | 6.2 |
| 21.88 | 1397 | 10.8 |
| 22.19 | 2181 | 16.9 |
| 23.18 | 278 | 2.2 |
| 23.44 | 240 | 1.9 |
| 24.19 | 2041 | 15.8 |
| 24.76 | 652 | 5.1 |
| 25.16 | 1374 | 10.6 |
| 25.55 | 1910 | 14.8 |
| 26.25 | 1042 | 8.1 |
| 27.08 | 259 | 2.0 |
| 27.98 | 627 | 4.9 |
| 28.43 | 408 | 3.2 |
| 29.18 | 644 | 5.0 |
| 29.41 | 665 | 5.2 |
| 29.89 | 471 | 3.7 |
| 30.64 | 1825 | 14.1 |
| 31.65 | 534 | 4.1 |
| 32.85 | 288 | 2.2 |
| 33.43 | 569 | 4.4 |
| 34.36 | 242 | 1.9 |
| 35.76 | 306 | 2.4 |
| 37.64 | 312 | 2.4 |
| 38.22 | 432 | 3.4 |
| 39.32 | 533 | 4.1 |
| 39.96 | 260 | 2.0 |

Example 4: Form B

Crystalline, anhydrous Form B material of 3-hydroxy-2-(5-isobutyryl-1-oxo-2,5-diazaspiro[3.4]octan-2-yl)butanamide was prepared by drying crystalline, monohydrate Form MH at a temperature above 130° C. (e.g., 150° C.). A 0.5 gram sample of crystalline, monohydrate Form MH of NYX-2925 was dried at 70° C. under a dry stream of $N_2$ for 1 h, then at 130° C. for 30 min, then at 150° for 30 min. XRPD analysis indicated that the material obtained was crystalline with a pattern consistent with anhydrous Form B.

Crystalline, anhydrous Form B material may be obtained by heating anhydrous Form A or monohydrate Form MH above their respective melting points (126° C. and 144° C., respectively), followed by crystallization from the melt.

Crystalline, anhydrous Form B material was further prepared by crystallization of 3-hydroxy-2-(5-isobutyryl-1-oxo-2,5-diazaspiro[3.4]octan-2-yl)butanamide from dry, non-aqueous solutions by fast cooling or fast evaporation. A 200 mg sample of 3-hydroxy-2-(5-isobutyryl-1-oxo-2,5-diazaspiro[3.4]octan-2-yl)butanamide was dissolved in 1.0 ml of isopropanol (previously dried over molecular sieves with a pore size of 4 Å) at 60° C. and immediately cooled to 0° C. with magnetic stirring. Crystallization occurred within 10 minutes. The suspension was stirred for additional 1.5 hours and the solid was filter centrifuged through a 0.20 μm PTFE filter. XRPD analysis indicated that the material obtained was crystalline with a pattern consistent with anhydrous Form B. Crystalline, anhydrous Form B was also obtained by the above-described procedure using tetrahydrofuran or ethyl acetate as solvent.

The above results indicate that anhydrous Form B is the kinetically favored anhydrous polymorphic form under conditions of fast cooling and/or fast evaporation.

Crystalline, anhydrous Form B material readily converts to the monohydrate Form MH in the solid state under ambient temperature and in an atmosphere of greater than or equal to 50% relative humidity, indicating that monohydrate Form MH is more stable than anhydrous Form B under conditions of ambient temperature and humidity.

Form B of 3-hydroxy-2-(5-isobutyryl-1-oxo-2,5-diazaspiro[3.4]octan-2-yl)butanamide has a solubility in isopropyl acetate of about 9 mg/mL after 10 minutes, 1 hour, and 6 hours at room temperature.

Characteristic peaks in the XRPD pattern for crystalline, anhydrous Form B of 3-hydroxy-2-(5-isobutyryl-1-oxo-2,5-diazaspiro[3.4]octan-2-yl)butanamide include one or more of the peaks shown in Table 10, below.

TABLE 10

| Peak Pos. [°2θ] | Peak Height [Cts] | Rel. Int. [%] |
| --- | --- | --- |
| 6.97 | 619 | 2.3 |
| 9.00 | 361 | 1.4 |
| 10.84 | 11797 | 44.7 |
| 13.36 | 2325 | 8.8 |
| 13.96 | 7988 | 30.3 |
| 15.53 | 26389 | 100.0 |
| 16.25 | 764 | 2.9 |
| 16.63 | 8120 | 30.8 |
| 17.28 | 1186 | 4.5 |
| 17.63 | 1793 | 6.8 |
| 18.42 | 8272 | 31.4 |
| 18.65 | 284 | 1.1 |
| 19.68 | 1715 | 6.5 |
| 20.24 | 9824 | 37.2 |
| 20.64 | 4534 | 17.2 |
| 20.99 | 410 | 1.6 |
| 22.27 | 2013 | 7.6 |
| 22.83 | 2418 | 9.2 |
| 23.18 | 269 | 1.0 |
| 23.63 | 193 | 0.7 |
| 24.20 | 1264 | 4.8 |
| 24.66 | 179 | 0.7 |
| 24.91 | 2754 | 10.4 |
| 25.30 | 1275 | 4.8 |
| 26.01 | 2201 | 8.3 |
| 26.61 | 2025 | 7.7 |
| 27.31 | 610 | 2.3 |
| 28.11 | 105 | 0.4 |
| 28.67 | 1052 | 4.0 |
| 28.78 | 1435 | 5.4 |
| 28.95 | 596 | 2.3 |
| 29.62 | 444 | 1.7 |
| 30.17 | 1466 | 5.6 |
| 30.73 | 945 | 3.6 |
| 31.00 | 735 | 2.8 |
| 31.32 | 467 | 1.8 |
| 32.06 | 185 | 0.7 |
| 32.48 | 655 | 2.5 |
| 32.67 | 252 | 1.0 |
| 33.18 | 776 | 2.9 |
| 33.45 | 262 | 1.0 |
| 33.80 | 750 | 2.8 |
| 34.38 | 969 | 3.7 |
| 34.76 | 199 | 0.8 |
| 34.95 | 224 | 0.9 |
| 35.30 | 637 | 2.4 |
| 35.69 | 381 | 1.4 |
| 36.37 | 713 | 2.7 |
| 37.06 | 625 | 2.4 |
| 37.22 | 615 | 2.3 |
| 37.75 | 220 | 0.8 |
| 38.03 | 372 | 1.4 |
| 38.32 | 1629 | 6.2 |
| 38.64 | 627 | 2.4 |
| 39.58 | 245 | 0.9 |
| 39.76 | 533 | 2.0 |
| 39.97 | 230 | 0.9 |

Example 5: Form C

Crystalline, anhydrous Form C material of 3-hydroxy-2-(5-isobutyryl-1-oxo-2,5-diazaspiro[3.4]octan-2-yl)butanamide was prepared as a mixture with anhydrous Form B by crystallization through fast evaporation from non-aqueous solutions (e.g., isopropanol, acetonitrile, and dichloromethane). For example, a 100 mg sample of 3-hydroxy-2-(5-isobutyryl-1-oxo-2,5-diazaspiro[3.4]octan-2-yl)butanamide was dissolved in 1 ml of PrOH (previously dried over molecular sieves with a pore size of 4 Å), and while magnetically stirring the solution the solvent was completely evaporated under a dry $N_2$ stream at RT within less than 16 h. The obtained white solid was kept in closed vial under $N_2$ until testing. XRPD analysis indicated that the material obtained was crystalline with a pattern consistent with a mixture of anhydrous Form B and anhydrous Form C.

Crystalline, anhydrous Form C material of 3-hydroxy-2-(5-isobutyryl-1-oxo-2,5-diazaspiro[3.4]octan-2-yl)butanamide is not stable in comparison to anhydrous Form A or anhydrous Form B under ambient conditions of temperature and humidity. Anhydrous Form C converts to anhydrous Form A in suspension in isopropanol, ethyl acetate, or isopropyl acetate at temperatures less than or equal to 50° C. Anhydrous Form C converts to anhydrous Form B in suspension in isopropanol, ethyl acetate, or isopropyl acetate at temperatures greater than or equal to 75° C. In turn, anhydrous Form A and anhydrous Form B each convert to monohydrate Form MH under the conditions described above. These observations indicate that crystalline, monohydrate Form MH is more stable under ambient conditions of temperature and humidity than anhydrous Forms A, B, and C.

Characteristic peaks in the XRPD pattern for crystalline, anhydrous Form C of 3-hydroxy-2-(5-isobutyryl-1-oxo-2,5-diazaspiro[3.4]octan-2-yl)butanamide include one or more of the peaks shown in Table 11, below.

TABLE 11

| Peak Pos. [° 2θ] | Peak Height [Cts] | Rel. Int. [%] |
| --- | --- | --- |
| 8.76 | 932 | 9.1 |
| 9.58 | 699 | 6.8 |
| 12.64 | 842 | 8.2 |
| 14.32 | 277 | 2.7 |
| 15.74 | 1985 | 19.3 |
| 16.72 | 5629 | 54.6 |
| 17.01 | 878 | 8.5 |
| 17.72 | 7095 | 68.9 |
| 20.46 | 802 | 7.8 |
| 21.92 | 655 | 6.4 |
| 22.46 | 415 | 4.0 |
| 26.42 | 1207 | 11.7 |
| 29.26 | 725 | 7.0 |
| 33.53 | 476 | 4.6 |
| 34.63 | 210 | 2.0 |
| 35.87 | 325 | 3.2 |

Example 6: Amorphous Solid Form

Amorphous material of 3-hydroxy-2-(5-isobutyryl-1-oxo-2,5-diazaspiro[3.4]octan-2-yl)butanamide was prepared by lyophilization of an aqueous solution. For example, 1.52 g of 3-hydroxy-2-(5-isobutyryl-1-oxo-2,5-diazaspiro[3.4]octan-2-yl)butanamide was weighed in a 1 liter round bottom flask and dissolved in 250 ml of water. The clear solution was filtered through a 0.45 μm PTFE filter, frozen in an isopropanol/dry ice mixture and lyophilized at room temperature and 0.008 mbar for 20 h to obtain a white solid. XRPD analysis indicated that the material obtained was amorphous.

Differential scanning calorimetry (DCS) analysis indicated that the amorphous form does not crystallize upon reheating but instead displays a glass transition of the amorphous form at about 59° C.

Figure 15:
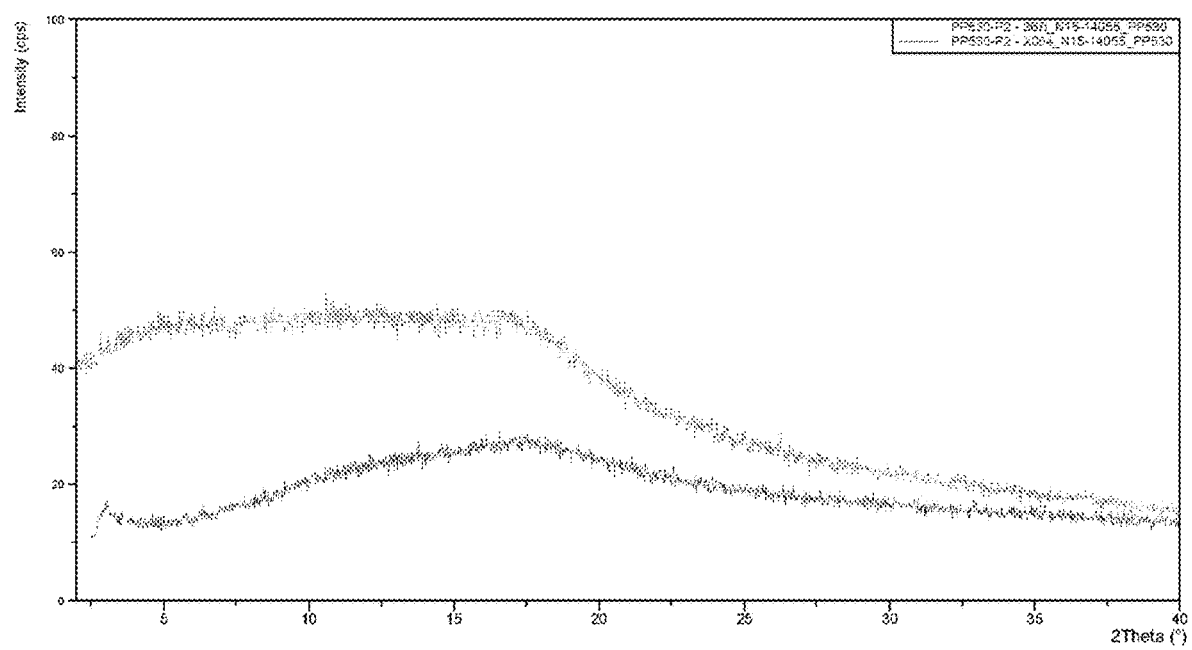
FIG. 15 depicts the XRPD patterns for amorphous NYX-2925 immediately after lyophilization (bottom trace, measured in reflection) and after 6 weeks of storage at −20° C. (top trace, measured in transmission). The patterns have different backgrounds due to the different instrument configurations.

XRPD analysis of a sample of amorphous 3-hydroxy-2-(5-isobutyryl-1-oxo-2,5-diazaspiro[3.4]octan-2-yl)butanamide after about six weeks of storage in a sealed vial at −20° C. indicated that the sample did not crystallize and was still in amorphous form, as shown in FIG. 15.

In solution, the amorphous form of 3-hydroxy-2-(5-isobutyryl-1-oxo-2,5-diazaspiro[3.4]octan-2-yl)butanamide crystallizes into anhydrous Form A from dry, non-aqueous solutions by slow cooling or slow evaporation and crystallized into anhydrous Form B from dry, non-aqueous solutions by fast cooling or fast evaporation. In turn, anhydrous Form A and anhydrous Form B each convert to monohydrate Form MH under the conditions described above.

Example 7: Alternate Stereoisomer

Single crystals of a different stereoisomer of 3-hydroxy-2-(5-isobutyryl-1-oxo-2,5-diazaspiro[3.4]octan-2-yl)butanamide (prepared analogously to NYX-2925 but starting with D-proline instead of L-proline) were grown and analyzed by single crystal X-ray analysis. The crystal displayed an orthorhombic system with the unit cell parameters and other crystallographic experimental details shown in Table 12, below.

TABLE 12

| | |
|---|---|
| Empirical formula | $C_{14}H_{23}N_3O_4$ |
| Formula weight | 297.35 |
| Temperature | 294(2) K |
| Wavelength | 0.71073 Å |
| Crystal system | Orthorhombic |
| Space group | $P2_12_12_1$ |
| Unit cell dimensions | a = 13.8318(12) Å  α = 90°. |
| | b = 15.2814(13) Å  β = 90°. |
| | c = 15.4981(13) Å  γ = 90°. |
| Volume | 3275.8(5) Å$^3$ |
| Z | 8 |
| Density (calculated) | 1.206 Mg/m$^3$ |
| Absorption coefficient | 0.089 mm$^{-1}$ |
| F(000) | 1280 |
| Crystal size | 0.180 × 0.160 × 0.090 mm$^3$ |
| θ range for data collection | 2.381 to 28.310°. |
| Index ranges | −18 <= h <= 18, −20 <= k <= 20, −20 <= l <= 20 |
| Reflections collected | 38115 |
| Independent reflections | 7934 [R(int) = 0.0210] |
| Completeness to theta = 25.242° | 99.9% |
| Refinement method | Full-matrix least-squares on F$^2$ |
| Data/restraints/parameters | 7934/15/409 |
| Goodness-of-fit on F$^2$ | 1.025 |
| Final R indices [I > 2σ(I)] | R1 = 0.0450, wR2 = 0.1211 |
| R indices (all data) | R1 = 0.0565, wR2 = 0.1314 |
| Absolute structure parameter | −0.1(2) |
| Largest diff. peak and hole | 0.273 and −0.152 e.Å$^{-3}$ |
| Measurement | Bruker Smart Apex CCD diffractometer |
| Software Used | SHELXTL-PLUS |

Figure 7:
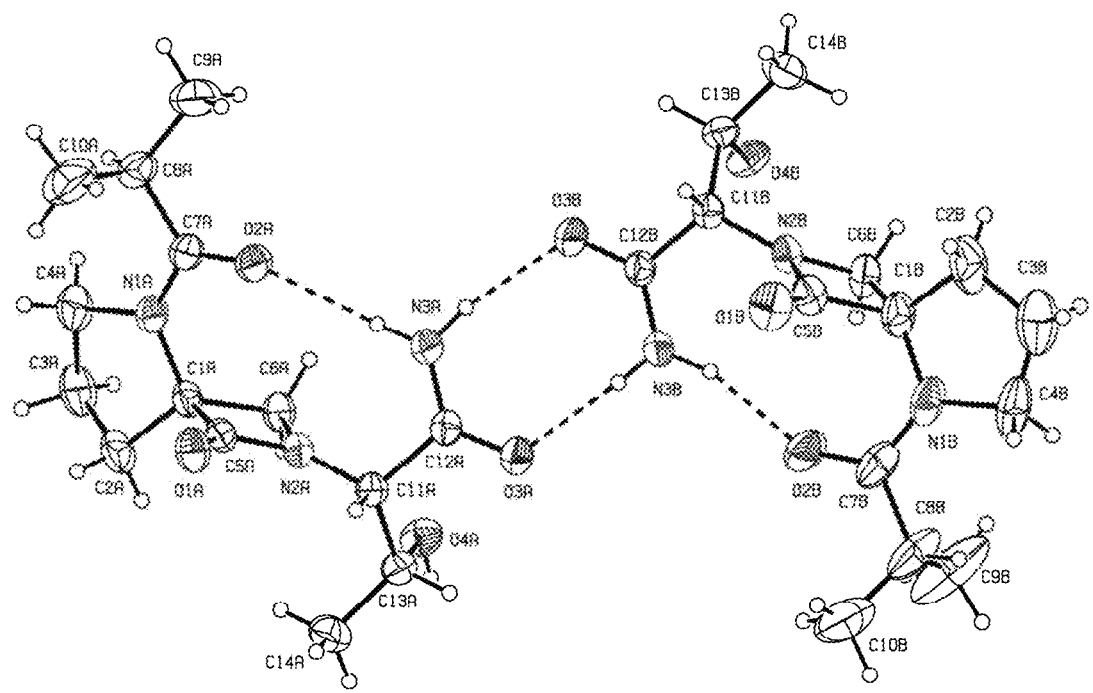
FIG. 7 depicts the X-ray crystal structure of a different stereoisomer of 3-hydroxy-2-(5-isobutyryl-1-oxo-2,5-diazaspiro[3.4]octan-2-yl)butanamide.

The X-ray crystal structure obtained from the single crystal determination of this particular stereoisomer of 3-hydroxy-2-(5-isobutyryl-1-oxo-2,5-diazaspiro[3.4]octan-2-yl)butanamide is shown in FIG. 7, with hydrogen atoms omitted for clarity. As shown in FIG. 7, the stereogenic centers labelled C1A, C11A, C13A, C1B, C11B, and C13B were demonstrated to have the configuration of (S), (S), and (R); and (S), (S) and (R), respectively.

Atomic coordinates (×10$^4$) and equivalent isotropic displacement parameters (Å$^2$×10$^3$) are shown in Table 13, below. U(eq) is defined as one third of the trace of the orthogonalized tensor.

TABLE 13

| Atom | x | y | z | U(eq) |
|---|---|---|---|---|
| C(1A) | 959(2) | 9190(2) | 9153(2) | 50(1) |
| C(2A) | 9(2) | 8751(2) | 8912(2) | 70(1) |
| C(3A) | −125(2) | 9012(3) | 7980(2) | 84(1) |
| C(4A) | 187(2) | 9963(2) | 7967(2) | 80(1) |
| C(5A) | 1134(2) | 9277(1) | 10128(2) | 48(1) |
| C(6A) | 1877(2) | 8604(2) | 9152(2) | 53(1) |
| C(7A) | 1580(2) | 10636(2) | 8791(2) | 57(1) |
| C(8A) | 1417(2) | 11499(2) | 8325(2) | 72(1) |
| C(9A) | 2341(3) | 12002(3) | 8254(3) | 105(1) |
| C(10A) | 634(4) | 12008(3) | 8794(4) | 129(2) |
| C(11A) | 2485(2) | 8377(1) | 10777(2) | 47(1) |
| C(12A) | 3529(2) | 8717(1) | 10752(2) | 47(1) |
| C(13A) | 2442(2) | 7379(2) | 10823(2) | 55(1) |
| C(14A) | 1428(2) | 7055(2) | 10972(3) | 78(1) |
| N(1A) | 958(2) | 9981(1) | 8635(1) | 57(1) |
| N(2A) | 1889(1) | 8717(1) | 10097(1) | 47(1) |
| N(3A) | 3687(2) | 9426(2) | 10287(2) | 61(1) |
| O(1A) | 750(1) | 9650(1) | 10724(1) | 67(1) |
| O(2A) | 7228(2) | 10552(2) | 9323(2) | 68(1) |
| O(3A) | 4148(1) | 8352(1) | 11185(1) | 63(1) |
| O(4A) | 2832(2) | 7081(1) | 10027(1) | 66(1) |
| C(1B) | 8743(2) | 9148(2) | 12627(2) | 69(1) |
| C(2B) | 9688(3) | 9578(4) | 12910(3) | 110(1) |
| C(3B) | 10160(4) | 8936(6) | 13422(6) | 187(4) |
| C(4B) | 9544(3) | 8250(4) | 13692(3) | 107(2) |
| C(5B) | 7882(2) | 9779(2) | 12608(1) | 57(1) |
| C(6B) | 8583(2) | 9071(2) | 11631(2) | 61(1) |
| C(7B) | 7876(3) | 7864(2) | 13137(2) | 86(1) |
| C(8B) | 7866(4) | 7023(3) | 13662(3) | 118(2) |
| C(9B) | 8200(9) | 6297(5) | 13121(5) | 210(3) |
| C(10B) | 6843(5) | 6836(3) | 14013(4) | 140(2) |
| C(11B) | 7210(2) | 10247(2) | 11171(1) | 46(1) |
| C(12B) | 6253(2) | 9784(2) | 10981(1) | 50(1) |
| C(13B) | 7700(2) | 10521(2) | 10337(2) | 52(1) |
| C(14B) | 8632(2) | 11030(2) | 10480(3) | 80(1) |
| N(4B) | 8674(2) | 8366(2) | 13150(2) | 81(1) |
| N(2B) | 7845(1) | 9765(1) | 11740(1) | 48(1) |
| N(3B) | 6094(1) | 9018(1) | 11352(1) | 52(1) |
| O(1B) | 7410(2) | 10191(2) | 13127(1) | 78(1) |
| O(2B) | 7180(2) | 8064(2) | 12690(2) | 92(1) |
| O(3B) | 5671(2) | 10152(2) | 10511(2) | 80(1) |
| O(4B) | 7894(2) | 9754(1) | 9850(1) | 61(1) |

Bond lengths (Å) and bond angles (°) are shown in Table 14, below.

TABLE 14

| | |
|---|---|
| C(1A)-N(1A) | 1.452(3) |
| C(1A)-C(2A) | 1.522(3) |
| C(1A)-C(5A) | 1.535(3) |
| C(1A)-C(6A) | 1.554(3) |
| C(2A)-C(3A) | 1.509(5) |
| C(2A)-H(2A1) | 0.9700 |
| C(2A)-H(2A2) | 0.9700 |
| C(3A)-C(4A) | 1.517(5) |
| C(3A)-H(3A1) | 0.9700 |
| C(3A)-H(3A2) | 0.9700 |
| C(4A)-N(1A) | 1.485(3) |
| C(4A)-H(4A1) | 0.9700 |
| C(4A)-H(4A2) | 0.9700 |
| C(5A)-O(1A) | 1.208(3) |
| C(5A)-N(2A) | 1.351(3) |
| C(6A)-N(2A) | 1.474(3) |
| C(6A)-H(6A1) | 0.9700 |
| C(6A)-H(6A2) | 0.9700 |
| C(7A)-O(2A) | 1.226(3) |
| C(7A)-N(1A) | 1.342(3) |
| C(7A)-C(8A) | 1.520(4) |
| C(8A)-C(9A) | 1.495(5) |
| C(8A)-C(10A) | 1.519(6) |
| C(8A)-H(8A) | 0.9800 |
| C(9A)-H(9A1) | 0.9600 |
| C(9A)-H(9A2) | 0.9600 |
| C(9A)-H(9A3) | 0.9600 |
| C(10A)-H(10A) | 0.9600 |

TABLE 14-continued

| | |
|---|---|
| C(10A)-H(10B) | 0.9600 |
| C(10A)-H(10C) | 0.9600 |
| C(11A)-N(2A) | 1.435(3) |
| C(11A)-C(13A) | 1.528(3) |
| C(11A)-C(12A) | 1.535(3) |
| C(11A)-H(11A) | 0.9800 |
| C(12A)-O(3A) | 1.222(3) |
| C(12A)-N(3A) | 1.319(3) |
| C(13A)-O(4A) | 1.420(3) |
| C(13A)-C(14A) | 1.505(4) |
| C(13A)-H(13A) | 0.9800 |
| C(14A)-H(14A) | 0.9600 |
| C(14A)-H(14B) | 0.9600 |
| C(14A)-H(14C) | 0.9600 |
| N(3A)-H(1N) | 0.88(3) |
| N(3A)-H(2N) | 0.87(4) |
| O(4A)-H(1O) | 0.80(4) |
| C(1B)-N(1B) | 1.448(4) |
| C(1B)-C(2B) | 1.528(5) |
| C(1B)-C(5B) | 1.532(4) |
| C(1B)-C(6B) | 1.565(4) |
| C(2B)-C(3B) | 1.421(8) |
| C(2B)-H(2B1) | 0.9700 |
| C(2B)-H(2B2) | 0.9700 |
| C(3B)-C(4B) | 1.414(8) |
| C(3B)-H(3B1) | 0.9700 |
| C(3B)-H(3B2) | 0.9700 |
| C(4B)-N(1B) | 1.478(4) |
| C(4B)-H(4B1) | 0.9700 |
| C(4B)-H(4B2) | 0.9700 |
| C(5B)-O(1B) | 1.212(3) |
| C(5B)-N(2B) | 1.346(3) |
| C(6B)-N(2B) | 1.481(3) |
| C(6B)-H(6B1) | 0.9700 |
| C(6B)-H(6B2) | 0.9700 |
| C(7B)-O(2B) | 1.226(4) |
| C(7B)-N(1B) | 1.344(5) |
| C(7B)-C(8B) | 1.521(5) |
| C(8B)-C(9B) | 1.467(9) |
| C(8B)-C(10B) | 1.542(9) |
| C(8B)-H(8B) | 0.9800 |
| C(9B)-H(9B1) | 0.9600 |
| C(9B)-H(9B2) | 0.9600 |
| C(9B)-H(9B3) | 0.9600 |
| C(10B)-H(10D) | 0.9600 |
| C(10B)-H(10E) | 0.9600 |
| C(10B)-H(10F) | 0.9600 |
| C(11B)-N(2B) | 1.447(3) |
| C(11B)-C(13B) | 1.519(3) |
| C(11B)-C(12B) | 1.530(3) |
| C(11B)-H(11B) | 0.9800 |
| C(12B)-O(3B) | 1.223(3) |
| C(12B)-N(3B) | 1.321(3) |
| C(13B)-O(4B) | 1.419(3) |
| C(13B)-C(14B) | 1.521(4) |
| C(13B)-H(13B) | 0.9800 |
| C(14B)-H(14D) | 0.9600 |
| C(14B)-H(14E) | 0.9600 |
| C(14B)-H(14F) | 0.9600 |
| N(3B)-H(3N) | 0.91(3) |
| N(3B)-H(4N) | 0.86(3) |
| O(4B)-H(2O) | 0.87(4) |
| N(1A)-C(1A)-C(2A) | 103.3(2) |
| N(1A)-C(1A)-C(5A) | 118.19(19) |
| C(2A)-C(1A)-C(5A) | 114.6(2) |
| N(1A)-C(1A)-C(6A) | 118.7(2) |
| C(2A)-C(1A)-C(6A) | 116.8(2) |
| C(5A)-C(1A)-C(6A) | 85.51(17) |
| C(3A)-C(2A)-C(1A) | 102.9(2) |
| C(3A)-C(2A)-H(2A1) | 111.2 |
| C(1A)-C(2A)-H(2A1) | 111.2 |
| C(3A)-C(2A)-H(2A2) | 111.2 |
| C(1A)-C(2A)-H(2A2) | 111.2 |
| H(2A1)-C(2A)-H(2A2) | 109.1 |
| C(2A)-C(3A)-C(4A) | 103.4(3) |
| C(2A)-C(3A)-H(3A1) | 111.1 |
| C(4A)-C(3A)-H(3A1) | 111.1 |
| C(2A)-C(3A)-H(3A2) | 111.1 |
| C(4A)-C(3A)-H(3A2) | 111.1 |
| H(3A1)-C(3A)-H(3A2) | 109.1 |
| N(1A)-C(4A)-C(3A) | 102.3(3) |
| N(1A)-C(4A)-H(4A1) | 111.3 |
| C(3A)-C(4A)-H(4A1) | 111.3 |
| N(1A)-C(4A)-H(4A2) | 111.3 |
| C(3A)-C(4A)-H(4A2) | 111.3 |
| H(4A1)-C(4A)-H(4A2) | 109.2 |
| O(1A)-C(5A)-N(2A) | 131.7(2) |
| O(1A)-C(5A)-C(1A) | 136.4(2) |
| N(2A)-C(5A)-C(1A) | 91.86(18) |
| N(2A)-C(6A)-C(1A) | 86.61(17) |
| N(2A)-C(6A)-H(6A1) | 114.2 |
| C(1A)-C(6A)-H(6A1) | 114.2 |
| N(2A)-C(6A)-H(6A2) | 114.2 |
| C(1A)-C(6A)-H(6A2) | 114.2 |
| H(6A1)-C(6A)-H(6A2) | 111.4 |
| O(2A)-C(7A)-N(1A) | 120.8(2) |
| O(2A)-C(7A)-C(8A) | 121.3(2) |
| N(1A)-C(7A)-C(8A) | 117.8(2) |
| C(9A)-C(8A)-C(10A) | 112.4(4) |
| C(9A)-C(8A)-C(7A) | 110.8(3) |
| C(10A)-C(8A)-C(7A) | 108.7(3) |
| C(9A)-C(8A)-H(8A) | 108.3 |
| C(10A)-C(8A)-H(8A) | 108.3 |
| C(7A)-C(8A)-H(8A) | 108.3 |
| C(8A)-C(9A)-H(9A1) | 109.5 |
| C(8A)-C(9A)-H(9A2) | 109.5 |
| H(9A1)-C(9A)-H(9A2) | 109.5 |
| C(8A)-C(9A)-H(9A3) | 109.5 |
| H(9A1)-C(9A)-H(9A3) | 109.5 |
| H(9A2)-C(9A)-H(9A3) | 109.5 |
| C(8A)-C(10A)-H(10A) | 109.5 |
| C(8A)-C(10A)-H(10B) | 109.5 |
| H(10A)-C(10A)-H(10B) | 109.5 |
| C(8A)-C(10A)-H(10C) | 109.5 |
| H(10A)-C(10A)-H(10C) | 109.5 |
| H(10B)-C(10A)-H(10C) | 109.5 |
| N(2A)-C(11A)-C(13A) | 111.89(19) |
| N(2A)-C(11A)-C(12A) | 113.61(18) |
| C(13A)-C(11A)-C(12A) | 112.06(19) |
| N(2A)-C(11A)-H(11A) | 106.2 |
| C(13A)-C(11A)-H(11A) | 106.2 |
| C(12A)-C(11A)-H(11A) | 106.2 |
| O(3A)-C(12A)-N(3A) | 124.0(2) |
| O(3A)-C(12A)-C(11A) | 119.4(2) |
| N(3A)-C(12A)-C(11A) | 116.5(2) |
| O(4A)-C(13A)-C(14A) | 112.4(3) |
| O(4A)-C(13A)-C(11A) | 105.3(2) |
| C(14A)-C(13A)-C(11A) | 111.8(2) |
| O(4A)-C(13A)-H(13A) | 109.0 |
| C(14A)-C(13A)-H(13A) | 109.0 |
| C(11A)-C(13A)-H(13A) | 109.0 |
| C(13A)-C(14A)-H(14A) | 109.5 |
| C(13A)-C(14A)-H(14B) | 109.5 |
| H(14A)-C(14A)-H(14B) | 109.5 |
| C(13A)-C(14A)-H(14C) | 109.5 |
| H(14A)-C(14A)-H(14C) | 109.5 |
| H(14B)-C(14A)-H(14C) | 109.5 |
| C(7A)-N(1A)-C(1A) | 121.39(19) |
| C(7A)-N(1A)-C(4A) | 126.8(2) |
| C(1A)-N(1A)-C(4A) | 111.8(2) |
| C(5A)-N(2A)-C(11A) | 130.37(19) |
| C(5A)-N(2A)-C(6A) | 95.76(18) |
| C(11A)-N(2A)-C(6A) | 133.87(19) |
| C(12A)-N(3A)-H(1N) | 121.8(19) |
| C(12A)-N(3A)-H(2N) | 127(2) |
| H(1N)-N(3A)-H(2N) | 111(3) |
| C(13A)-O(4A)-H(1O) | 108(3) |
| N(1B)-C(1B)-C(2B) | 104.5(3) |
| N(1B)-C(1B)-C(5B) | 118.7(3) |
| C(2B)-C(1B)-C(5B) | 113.6(3) |
| N(1B)-C(1B)-C(6B) | 118.8(3) |
| C(2B)-C(1B)-C(6B) | 115.9(3) |
| C(5B)-C(1B)-C(6B) | 85.34(18) |
| C(3B)-C(2B)-C(1B) | 104.8(5) |
| C(3B)-C(2B)-H(2B1) | 110.8 |
| C(1B)-C(2B)-H(2B1) | 110.8 |
| C(3B)-C(2B)-H(2B2) | 110.8 |
| C(1B)-C(2B)-H(2B2) | 110.8 |
| H(2B1)-C(2B)-H(2B2) | 108.9 |
| C(4B)-C(3B)-C(2B) | 113.6(4) |

TABLE 14-continued

| | |
|---|---|
| C(4B)-C(3B)-H(3B1) | 108.8 |
| C(2B)-C(3B)-H(3B1) | 108.8 |
| C(4B)-C(3B)-H(3B2) | 108.8 |
| C(2B)-C(3B)-H(3B2) | 108.8 |
| H(3B1)-C(3B)-H(3B2) | 107.7 |
| C(3B)-C(4B)-N(1B) | 103.5(4) |
| C(3B)-C(4B)-H(4B1) | 111.1 |
| N(1B)-C(4B)-H(4B1) | 111.1 |
| C(3B)-C(4B)-H(4B2) | 111.1 |
| N(1B)-C(4B)-H(4B2) | 111.1 |
| H(4B1)-C(4B)-H(4B2) | 109.0 |
| O(1B)-C(5B)-N(2B) | 130.6(3) |
| O(1B)-C(5B)-C(1B) | 137.1(2) |
| N(2B)-C(5B)-C(1B) | 92.2(2) |
| N(2B)-C(6B)-C(1B) | 85.98(19) |
| N(2B)-C(6B)-H(6B1) | 114.3 |
| C(1B)-C(6B)-H(6B1) | 114.3 |
| N(2B)-C(6B)-H(6B2) | 114.3 |
| C(1B)-C(6B)-H(6B2) | 114.3 |
| H(6B1)-C(6B)-H(6B2) | 111.5 |
| O(2B)-C(7B)-N(1B) | 120.8(3) |
| O(2B)-C(7B)-C(8B) | 120.4(4) |
| N(1B)-C(7B)-C(8B) | 118.8(3) |
| C(9B)-C(8B)-C(7B) | 109.2(4) |
| C(9B)-C(8B)-C(10B) | 110.5(7) |
| C(7B)-C(8B)-C(10B) | 110.7(4) |
| C(9B)-C(8B)-H(8B) | 108.8 |
| C(7B)-C(8B)-H(8B) | 108.8 |
| C(10B)-C(8B)-H(8B) | 108.8 |
| C(8B)-C(9B)-H(9B1) | 109.5 |
| C(8B)-C(9B)-H(9B2) | 109.5 |
| H(9B1)-C(9B)-H(9B2) | 109.5 |
| C(8B)-C(9B)-H(9B3) | 109.5 |
| H(9B1)-C(9B)-H(9B3) | 109.5 |
| H(9B2)-C(9B)-H(9B3) | 109.5 |
| C(8B)-C(10B)-H(10D) | 109.5 |
| C(8B)-C(10B)-H(10E) | 109.5 |
| H(10D)-C(10B)-H(10E) | 109.5 |
| C(8B)-C(10B)-H(10F) | 109.5 |
| H(10D)-C(10B)-H(10F) | 109.5 |
| H(10E)-C(10B)-H(10F) | 109.5 |
| N(2B)-C(11B)-C(13B) | 112.80(18) |
| N(2B)-C(11B)-C(12B) | 114.04(19) |
| C(13B)-C(11B)-C(12B) | 110.50(18) |
| N(2B)-C(11B)-H(11B) | 106.3 |
| C(13B)-C(11B)-H(11B) | 106.3 |
| C(12B)-C(11B)-H(11B) | 106.3 |
| O(3B)-C(12B)-N(3B) | 123.9(2) |
| O(3B)-C(12B)-C(11B) | 118.1(2) |
| N(3B)-C(12B)-C(11B) | 118.0(2) |
| O(4B)-C(13B)-C(11B) | 108.00(18) |
| O(4B)-C(13B)-C(14B) | 109.9(2) |
| C(11B)-C(13B)-C(14B) | 113.3(2) |
| O(4B)-C(13B)-H(13B) | 108.5 |
| C(11B)-C(13B)-H(13B) | 108.5 |
| C(14B)-C(13B)-H(13B) | 108.5 |
| C(13B)-C(14B)-H(14D) | 109.5 |
| C(13B)-C(14B)-H(14E) | 109.5 |
| H(14D)-C(14B)-H(14E) | 109.5 |
| C(13B)-C(14B)-H(14F) | 109.5 |
| H(14D)-C(14B)-H(14F) | 109.5 |
| H(14E)-C(14B)-H(14F) | 109.5 |
| C(7B)-N(1B)-C(1B) | 121.0(2) |
| C(7B)-N(1B)-C(4B) | 127.5(3) |
| C(1B)-N(1B)-C(4B) | 111.4(4) |
| C(5B)-N(2B)-C(11B) | 128.6(2) |
| C(5B)-N(2B)-C(6B) | 95.78(19) |
| C(11B)-N(2B)-C(6B) | 135.48(18) |
| C(12B)-N(3B)-H(3N) | 122(2) |
| C(12B)-N(3B)-H(4N) | 117.8(18) |
| H(3N)-N(3B)-H(4N) | 120(3) |
| C(13B)-O(4B)-H(2O) | 107(2) |

Anisotropic displacement parameters (Å$^2$×10$^3$) are shown in Table 15, below. The anisotropic displacement factor exponent may be expressed in the form: $-2\pi^2[h^2 a^{*2} U^{11} + \ldots + 2 h k a^* b^* U^{12}]$.

TABLE 15

| | $U^{11}$ | $U^{22}$ | $U^{33}$ | $U^{23}$ | $U^{13}$ | $U^{12}$ |
|---|---|---|---|---|---|---|
| C(1A) | 38(1) | 52(1) | 61(1) | −5(1) | −7(1) | −1(1) |
| C(2A) | 45(1) | 71(2) | 92(2) | −11(2) | −13(1) | −9(1) |
| C(3A) | 57(2) | 105(2) | 89(2) | −22(2) | −27(2) | −7(2) |
| C(4A) | 61(2) | 105(2) | 74(2) | 4(2) | −31(1) | −6(2) |
| C(5A) | 38(1) | 48(1) | 59(1) | −1(1) | 0(1) | −2(1) |
| C(6A) | 48(1) | 61(1) | 52(1) | −10(1) | −4(1) | 5(1) |
| C(7A) | 55(1) | 64(1) | 53(1) | 7(1) | −10(1) | −3(1) |
| C(8A) | 77(2) | 75(2) | 63(2) | 21(1) | −15(1) | −6(2) |
| C(9A) | 115(3) | 90(2) | 109(3) | 37(2) | −22(2) | −34(2) |
| C(10A) | 146(4) | 93(3) | 148(4) | 43(3) | 35(3) | 47(3) |
| C(11A) | 45(1) | 48(1) | 47(1) | −2(1) | 1(1) | 2(1) |
| C(12A) | 45(1) | 47(1) | 50(1) | −4(1) | −6(1) | 4(1) |
| C(13A) | 57(1) | 50(1) | 59(1) | 5(1) | 2(1) | 2(1) |
| C(14A) | 67(2) | 63(2) | 105(2) | 6(2) | 7(2) | −13(1) |
| N(1A) | 48(1) | 64(1) | 60(1) | 5(1) | −16(1) | −2(1) |
| N(2A) | 41(1) | 49(1) | 50(1) | −3(1) | −1(1) | 3(1) |
| N(3A) | 47(1) | 59(1) | 79(2) | 14(1) | −14(1) | −6(1) |
| O(1A) | 53(1) | 78(1) | 69(1) | −12(1) | 7(1) | 15(1) |
| O(2A) | 64(1) | 64(1) | 76(1) | 13(1) | −27(1) | −14(1) |
| O(3A) | 52(1) | 63(1) | 74(1) | 10(1) | −14(1) | 1(1) |
| O(4A) | 82(1) | 47(1) | 68(1) | −5(1) | 8(1) | 7(1) |
| C(1B) | 55(1) | 98(2) | 55(1) | 2(1) | −15(1) | 8(2) |
| C(2B) | 65(2) | 157(4) | 108(3) | −4(3) | −41(2) | −4(2) |
| C(3B) | 96(3) | 250(8) | 216(7) | 75(7) | −93(4) | −15(5) |
| C(4B) | 89(2) | 159(4) | 75(2) | −4(2) | −36(2) | 49(3) |
| C(5B) | 54(1) | 79(2) | 38(1) | −5(1) | −7(1) | −2(1) |
| C(6B) | 51(1) | 81(2) | 50(1) | −2(1) | −5(1) | 17(1) |
| C(7B) | 108(3) | 85(2) | 66(2) | 17(2) | −29(2) | 17(2) |
| C(8B) | 172(4) | 92(2) | 90(2) | 31(2) | −51(3) | 25(3) |
| C(9B) | 373(9) | 119(4) | 137(4) | 34(3) | −8(5) | 112(5) |
| C(10B) | 187(5) | 94(3) | 139(4) | 52(3) | −44(3) | −17(3) |
| C(11B) | 44(1) | 53(1) | 41(1) | −4(1) | 1(1) | 4(1) |
| C(12B) | 43(1) | 62(1) | 45(1) | 4(1) | −2(1) | 3(1) |
| C(13B) | 61(1) | 47(1) | 49(1) | 6(1) | 7(1) | 4(1) |
| C(14B) | 69(2) | 64(2) | 108(2) | 1(2) | 25(2) | −9(1) |
| N(1B) | 77(2) | 107(2) | 60(1) | 11(1) | −27(1) | 22(2) |
| N(2B) | 40(1) | 68(1) | 37(1) | −4(1) | −1(1) | 5(1) |
| N(3B) | 40(1) | 61(1) | 54(1) | 6(1) | −3(1) | 1(1) |
| O(1B) | 90(1) | 104(2) | 39(1) | −13(1) | 4(1) | 18(1) |
| O(2B) | 95(2) | 96(2) | 85(2) | 38(1) | −36(1) | −6(1) |
| O(3B) | 57(1) | 84(1) | 99(2) | 33(1) | −30(1) | −7(1) |
| O(4B) | 91(1) | 55(1) | 38(1) | 3(1) | 7(1) | 11(1) |

Hydrogen coordinates (×10$^4$) and isotropic displacement parameters (Å$^2$×10$^3$) are shown in Table 16, below.

TABLE 16

| | x | y | z | U(eq) |
|---|---|---|---|---|
| H(2A1) | 52 | 8120 | 8972 | 83 |
| H(2A2) | −519 | 8965 | 9267 | 83 |
| H(3A1) | −795 | 8951 | 7805 | 101 |
| H(3A2) | 278 | 8660 | 7603 | 101 |
| H(4A1) | 438 | 10129 | 7406 | 96 |
| H(4A2) | −343 | 10349 | 8118 | 96 |
| H(6A1) | 1763 | 8007 | 8964 | 64 |
| H(6A2) | 2428 | 8859 | 8858 | 64 |
| H(8A) | 1186 | 11371 | 7740 | 86 |
| H(9A1) | 2557 | 12166 | 8820 | 157 |
| H(9A2) | 2235 | 12519 | 7914 | 157 |
| H(9A3) | 2823 | 11645 | 7981 | 157 |
| H(10A) | 863 | 12173 | 9356 | 194 |
| H(10B) | 69 | 11648 | 8854 | 194 |
| H(10C) | 474 | 12523 | 8470 | 194 |
| H(11A) | 2206 | 8592 | 11317 | 56 |
| H(13A) | 2856 | 7177 | 11296 | 66 |
| H(14A) | 1019 | 7248 | 10509 | 117 |
| H(14B) | 1190 | 7283 | 11508 | 117 |
| H(14C) | 1429 | 6427 | 10994 | 117 |
| H(1N) | 4260(20) | 9676(19) | 10266(18) | 58(7) |
| H(2N) | 3260(30) | 9720(20) | 9990(20) | 72(9) |
| H(1O) | 2760(30) | 6560(20) | 10010(20) | 76(10) |
| H(2B1) | 10080 | 9733 | 12413 | 132 |
| H(2B2) | 9562 | 10102 | 13245 | 132 |
| H(3B1) | 10691 | 8689 | 13092 | 224 |

TABLE 16-continued

|  | x | y | z | U(eq) |
|---|---|---|---|---|
| H(3B2) | 10433 | 9217 | 13927 | 224 |
| H(4B1) | 9388 | 8304 | 14300 | 129 |
| H(4B2) | 9840 | 7683 | 13592 | 129 |
| H(6B1) | 9136 | 9244 | 11286 | 73 |
| H(6B2) | 8325 | 8512 | 11445 | 73 |
| H(8B) | 8310 | 7089 | 14151 | 142 |
| H(9B1) | 7716 | 6164 | 12696 | 315 |
| H(9B2) | 8312 | 5791 | 13474 | 315 |
| H(9B3) | 8790 | 6460 | 12837 | 315 |
| H(10D) | 6418 | 6702 | 13542 | 210 |
| H(10E) | 6607 | 7343 | 14314 | 210 |
| H(10F) | 6868 | 6348 | 14403 | 210 |
| H(11B) | 7043 | 10789 | 11475 | 55 |
| H(13B) | 7252 | 10890 | 10009 | 63 |
| H(14D) | 9088 | 10668 | 10781 | 120 |
| H(14E) | 8498 | 11543 | 10817 | 120 |
| H(14F) | 8898 | 11200 | 9933 | 120 |
| H(3N) | 6540(20) | 8750(20) | 11690(20) | 60(8) |
| H(4N) | 5530(20) | 8780(17) | 11281(18) | 51(7) |
| H(2O) | 7780(20) | 9880(20) | 9310(20) | 73(9) |

Torsion angles (°) are shown in Table 17, below.

TABLE 17

| N(1A)-C(1A)-C(2A)-C(3A) | 32.3(3) |
|---|---|
| C(5A)-C(1A)-C(2A)-C(3A) | 162.3(2) |
| C(6A)-C(1A)-C(2A)-C(3A) | −100.0(3) |
| C(1A)-C(2A)-C(3A)-C(4A) | −40.9(3) |
| C(2A)-C(3A)-C(4A)-N(1A) | 32.9(3) |
| N(1A)-C(1A)-C(5A)-O(1A) | 59.2(4) |
| C(2A)-C(1A)-C(5A)-O(1A) | −63.0(4) |
| C(6A)-C(1A)-C(5A)-O(1A) | 179.6(3) |
| N(1A)-C(1A)-C(5A)-N(2A) | −124.1(2) |
| C(2A)-C(1A)-C(5A)-N(2A) | 113.7(2) |
| C(6A)-C(1A)-C(5A)-N(2A) | −3.79(18) |
| N(1A)-C(1A)-C(6A)-N(2A) | 123.3(2) |
| C(2A)-C(1A)-C(6A)-N(2A) | −111.9(2) |
| C(5A)-C(1A)-C(6A)-N(2A) | 3.47(16) |
| O(2A)-C(7A)-C(8A)-C(9A) | 28.0(4) |
| N(1A)-C(7A)-C(8A)-C(9A) | −155.5(3) |
| O(2A)-C(7A)-C(8A)-C(10A) | −96.1(4) |
| N(1A)-C(7A)-C(8A)-C(10A) | 80.4(4) |
| N(2A)-C(11A)-C(12A)-O(3A) | −165.9(2) |
| C(13A)-C(11A)-C(12A)-O(3A) | −37.8(3) |
| N(2A)-C(11A)-C(12A)-N(3A) | 17.6(3) |
| C(13A)-C(11A)-C(12A)-N(3A) | 145.6(2) |
| N(2A)-C(11A)-C(13A)-O(4A) | 63.4(2) |
| C(12A)-C(11A)-C(13A)-O(4A) | −65.6(3) |
| N(2A)-C(11A)-C(13A)-C(14A) | −59.1(3) |
| C(12A)-C(11A)-C(13A)-C(14A) | 172.0(2) |
| O(2A)-C(7A)-N(1A)-C(1A) | 6.9(4) |
| C(8A)-C(7A)-N(1A)-C(1A) | −169.6(2) |
| O(2A)-C(7A)-N(1A)-C(4A) | −175.1(3) |
| C(8A)-C(7A)-N(1A)-C(4A) | 8.4(4) |
| C(2A)-C(1A)-N(1A)-C(7A) | 166.2(2) |
| C(5A)-C(1A)-N(1A)-C(7A) | 38.5(3) |
| C(6A)-C(1A)-N(1A)-C(7A) | −62.7(3) |
| C(2A)-C(1A)-N(1A)-C(4A) | −12.0(3) |
| C(5A)-C(1A)-N(1A)-C(4A) | −139.8(2) |
| C(6A)-C(1A)-N(1A)-C(4A) | 119.1(2) |
| C(3A)-C(4A)-N(1A)-C(7A) | 168.9(3) |
| C(3A)-C(4A)-N(1A)-C(1A) | −13.0(3) |
| O(1A)-C(5A)-N(2A)-C(11A) | 0.1(4) |
| C(1A)-C(5A)-N(2A)-C(11A) | −176.8(2) |
| O(1A)-C(5A)-N(2A)-C(6A) | −179.1(3) |
| C(1A)-C(5A)-N(2A)-C(6A) | 4.00(19) |
| C(13A)-C(11A)-N(2A)-C(5A) | 120.6(2) |
| C(12A)-C(11A)-N(2A)-C(5A) | −111.3(2) |
| C(13A)-C(11A)-N(2A)-C(6A) | −60.5(3) |
| C(12A)-C(11A)-N(2A)-C(6A) | 67.6(3) |
| C(1A)-C(6A)-N(2A)-C(5A) | −3.95(18) |
| C(1A)-C(6A)-N(2A)-C(11A) | 176.9(2) |
| N(1B)-C(1B)-C(2B)-C(3B) | 11.4(6) |
| C(5B)-C(1B)-C(2B)-C(3B) | 142.2(5) |
| C(6B)-C(1B)-C(2B)-C(3B) | −121.3(5) |

TABLE 17-continued

| C(1B)-C(2B)-C(3B)-C(4B) | −15.8(9) |
|---|---|
| C(2B)-C(3B)-C(4B)-N(1B) | 13.2(8) |
| N(1B)-C(1B)-C(5B)-O(1B) | 56.5(5) |
| C(2B)-C(1B)-C(5B)-O(1B) | −66.8(5) |
| C(6B)-C(1B)-C(5B)-O(1B) | 177.0(4) |
| N(1B)-C(1B)-C(5B)-N(2B) | 126.8(3) |
| C(2B)-C(1B)-C(5B)-N(2B) | 109.8(3) |
| C(6B)-C(1B)-C(5B)-N(2B) | −6.4(2) |
| N(1B)-C(1B)-C(6B)-N(2B) | 126.1(3) |
| C(2B)-C(1B)-C(6B)-N(2B) | −108.1(3) |
| C(5B)-C(1B)-C(6B)-N(2B) | 5.9(2) |
| O(2B)-C(7B)-C(8B)-C(9B) | 86.2(7) |
| N(1B)-C(7B)-C(8B)-C(9B) | −91.7(7) |
| O(2B)-C(7B)-C(8B)-C(10B) | −35.7(6) |
| N(1B)-C(7B)-C(8B)-C(10B) | 146.4(4) |
| N(2B)-C(11B)-C(12B)-O(3B) | 179.4(2) |
| C(13B)-C(11B)-C(12B)-O(3B) | −52.3(3) |
| N(2B)-C(11B)-C(12B)-N(3B) | 1.0(3) |
| C(13B)-C(11B)-C(12B)-N(3B) | 129.3(2) |
| N(2B)-C(11B)-C(13B)-O(4B) | 67.8(2) |
| C(12B)-C(11B)-C(13B)-O(4B) | −61.1(2) |
| N(2B)-C(11B)-C(13B)-C(14B) | −54.1(3) |
| C(12B)-C(11B)-C(13B)-C(14B) | 176.9(2) |
| O(2B)-C(7B)-N(1B)-C(1B) | −1.2(6) |
| C(8B)-C(7B)-N(1B)-C(1B) | 176.7(3) |
| O(2B)-C(7B)-N(1B)-C(4B) | 175.7(4) |
| C(8B)-C(7B)-N(1B)-C(4B) | −6.5(6) |
| C(2B)-C(1B)-N(1B)-C(7B) | 173.3(4) |
| C(5B)-C(1B)-N(1B)-C(7B) | 45.5(4) |
| C(6B)-C(1B)-N(1B)-C(7B) | −55.7(4) |
| C(2B)-C(1B)-N(1B)-C(4B) | −4.0(4) |
| C(5B)-C(1B)-N(1B)-C(4B) | −131.8(3) |
| C(6B)-C(1B)-N(1B)-C(4B) | 127.0(3) |
| C(3B)-C(4B)-N(1B)-C(7B) | 178.0(5) |
| C(3B)-C(4B)-N(1B)-C(1B) | −4.9(6) |
| O(1B)-C(5B)-N(2B)-C(11B) | −0.5(5) |
| C(1B)-C(5B)-N(2B)-C(11B) | −177.5(2) |
| O(1B)-C(5B)-N(2B)-C(6B) | −176.2(3) |
| C(1B)-C(5B)-N(2B)-C(6B) | 6.8(2) |
| C(13B)-C(11B)-N(2B)-C(5B) | 144.6(3) |
| C(12B)-C(11B)-N(2B)-C(5B) | −88.3(3) |
| C(13B)-C(11B)-N(2B)-C(6B) | −41.5(4) |
| C(12B)-C(11B)-N(2B)-C(6B) | 85.7(3) |
| C(1B)-C(6B)-N(2B)-C(5B) | −6.7(2) |
| C(1B)-C(6B)-N(2B)-C(11B) | 178.1(3) |

Hydrogen bond distances (Å) and angles (°) are shown in Table 18, below. Symmetry transformations used to generate equivalent atoms: #1 x−1/2,−y+3/2,−z+2; #2−x+3/2,−y+2, z−1/2.

TABLE 18

| D-H . . . A | d(D-H) | d(H . . . A) | d(D . . . A) | <(DHA) |
|---|---|---|---|---|
| N(3A)-H(1N) . . . O(3B) | 0.88(3) | 2.12(3) | 2.980(3) | 166(3) |
| N(3A)-H(2N) . . . O(2A) | 0.87(4) | 2.18(4) | 3.044(3) | 175(3) |
| O(4A)-H(1O) . . . O(4B) #1 | 0.80(4) | 2.03(4) | 2.812(3) | 164(4) |
| N(3B)-H(3N) . . . O(2B) | 0.91(3) | 2.07(3) | 2.946(3) | 162(3) |
| N(3B)-H(4N) . . . O(3A) | 0.86(3) | 2.03(3) | 2.889(3) | 173(3) |
| O(4B)-H(2O) . . . O(1B) #2 | 0.87(4) | 1.86(4) | 2.704(2) | 164(3) |

Example 8: Manufacturing Process for 3-Hydroxy-2-(5-isobutyryl-1-oxo-2,5-diazaspiro[3.4]octan-2-yl)butanamide Monohydrate

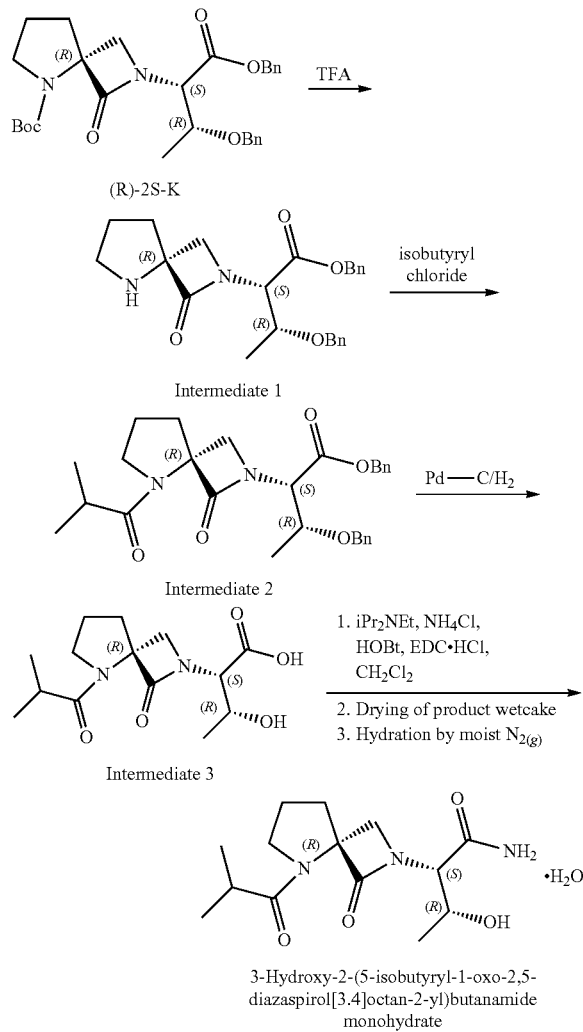

To a solution of (R)-2S-K (obtained from separation of diastereomers in 2S-K) in DCM at 0-10° C. was added TFA and the reaction mixture was warmed to 20-30° C. After the reaction was complete, the reaction mixture was concentrated under vacuum and residual DCM was removed by performing two diisopropyl ether (DIPE) chases with concentration under vacuum. DIPE was added and the resulting suspension was cooled to 15-20° C. and the product was filtered, washed with DIPE, and dried under vacuum at 40-50° C. to afford Intermediate 1 as its TFA salt.

The TFA salt of Intermediate 1 was dissolved in aqueous NaHCO$_3$ solution to generate its free base. The resulting free base was extracted into DCM and then cooled to 0-10° C. Triethylamine was added followed by isobutyryl chloride, and the mixture was kept at 0-10° C. until the reaction was completed. Aqueous NH$_4$Cl solution was added to quench the reaction and the mixture was warmed to 20-30° C. The product-rich organic layer was separated, and the aqueous layer was back-extracted with DCM. The organic layer and the DCM extract were combined and washed with NaHCO$_3$ solution followed by brine solution. The product-rich organic layer was separated, concentrated under vacuum, and residual DCM was removed by performing two n-heptane chases with concentration under vacuum. n-Heptane was added to the concentrate and the resulting suspension was filtered, washed with n-heptane, and dried under vacuum at 40-50° C. to afford Intermediate 2.

A solution of Intermediate 2 in MeOH was subjected to hydrogenation conditions with 10% Pd/C at 20-30° C. After the reaction was complete, the reaction mixture was filtered through a Celite bed and the bed was rinsed with MeOH. The filtrate and MeOH rinse were combined, concentrated under vacuum, and residual MeOH was removed by performing two chases with DIPE chases with concentration under vacuum. DIPE was added to the concentrate and the resulting suspension was filtered, washed with DIPE, and dried under vacuum at less than 45° C. to afford Intermediate 3.

To a solution of Intermediate 3 in DCM at 0-5° C. was slowly added DIPEA, ammonium chloride, 1-hydroxybenzotriazole (HOBt), and 1-ethyl-3-(3-dimethylaminopropyl)-carbodiimide hydrochloride (EDC·HCl) to a reactor which had been inerted with nitrogen. The mixture was warmed to ambient temperature. After the reaction was complete (HPLC, IPC-1, Table 19), brine was added. The organic layer was separated, and the aqueous layer was back-extracted twice with DCM. The product-rich organic layer and the two extracts were combined and tested by IPC-2 (Table 19), and concentrated under vacuum to remove DCM. Water was added to the residue and the resulting mixture containing undissolved solids (HOBt) was filtered. After washing the filtered solids with water, the mother liquor and water washes were combined and cooled to 5-10° C.

While maintaining the temperature below 10° C., aqueous ammonia solution was added to the aqueous product solution to adjust the pH to 10.5-11.0 (IPC-3, Table 19). The aqueous layer was washed three times with DIPE while monitoring the pH of the aqueous layer using IPC-3 (pH 10.5-11.0); if needed, aqueous ammonia solution was added to adjust the pH to 10.5-11.0. Solid sodium chloride was added, and the aqueous product solution was extracted three times with DCM. The DCM extracts were combined and concentrated under vacuum down to 1.5-2.0 volumes with respect to batch size.

DIPE was added to the concentrate. Over time, the product precipitated out of solution as white solids. The product slurry was filtered, and the product solids were washed with DIPE. The washed solids were pulled dry to a wetcake.

The product was purified by two precipitation steps using DCM/DIPE. IPC-4 (Table 19) was used to test the wetcake for purity and yield after each precipitation. If IPC-4 was not met, additional precipitations using DCM/DIPE were carried out.

Residual DCM was removed with ethanol slurry chases of the wetcake. Afterwards, solvent exchange with DIPE was performed to minimize ethanol content in the slurry.

Filtration of the product slurry afforded a wetcake that was dried under vacuum until the product met the residual solvent specification (IPC-5 and IPC-6, Table 19). The yield of anhydrous NYX-2925 obtained as an off-white solid, was 45.9% yield with an HPLC purity of 99.8 area %.

The anhydrous NYX-2925 was hydrated by rotating the solid in a round-bottomed flask at ambient temperature, under a flow of moist nitrogen gas through the flask. The solids were periodically sampled and tested for water content (IPC-7, Table 19). After an extended period of time, the water content reached 5.4% (theoretical moisture content for monohydrate is 5.7%). The yield of NYX-2925 monohydrate, obtained as an off-white solid, was 93.3% yield; the water content of the bulk material when QC release tested was 5.7%.

Example 9: Manufacturing Process for 3-Hydroxy-2-(5-isobutyryl-1-oxo-2,5-diazaspiro[3.4]octan-2-yl)butanamide Monohydrate—Direct Hydration Process The process was performed as described in Example 8 above. After solvent exchange with DIPE was performed to minimize ethanol content in the slurry, a small quantity of water (2.0 equiv) was added to the product slurry and the suspension was stirred for 3 h. The suspension was filtered and the wetcake was washed with DIPE. The wetcake was suction dried under vacuum while on the Buchner funnel; periodically, the product cake was manually agitated. The solids were suction dried until it met the residual solvent specification (IPC-6, Table 19). The water content of the product was found to be 5.7-5.8% (IPC-7, Table 19).

talline cellulose, starch, and magnesium stearate. NYX-2925 monohydrate oral capsules at 10 mg, 50 mg, and 100 mg strengths were placed on stability for 6 months at 40° C./75% relative humidity and for 6 months at 25° C./60% relative humidity; there were no significant changes in the impurity profile or other quality attributes such as appearance, assay, water content, microbial examination, and XRPD.

Example 11: Study of NYX-2925 in Subjects with Neuropathic Pain Associated with Diabetic Peripheral Neuropathy A randomized, double-blind, parallel-group, placebo-controlled, multiple-dose study was conducted to assess the efficacy and safety of NYX-2925 in subjects with neuropathic pain associated with diabetic peripheral neuropathy.

The study was to evaluate the efficacy of multiple dose levels of NYX-2925 versus placebo in treating the neuropathic pain associated with diabetic peripheral neuropathy.

The study was also to assess the effects of multiple dose levels of NYX-2925 versus placebo on pain characteristics, sleep interference, health status, psychological state, and

TABLE 19

In-Process Controls

| IPC | Test Parameter | Acceptance Criteria |
| --- | --- | --- |
| 1 | Content of previous step by HPLC (area %) | Not more than 1.0 |
| 2 | Purity of crude product by HPLC (area %) | Report the result |
|   | Assay of crude product by HPLC | Report the result |
| 3 | pH of aqueous layer washes during workup | Between 10.5 and 11.0 |
| 4 | Related Substances by HPLC (area (1/0): | |
|   | Unknown Impurity at RRT 0.58 | ≤0.20 |
|   | Unknown Impurity at RRT 0.95 | ≤0.40 |
|   | Unknown Impurity at RRT 1.05 | ≤0.40 |
|   | Unknown Impurity at RRT 1.15 | ≤0.40 |
|   | Unknown Impurity at RRT 1.26 | ≤0.40 |
|   | Unknown Impurity at RRT 1.29 | <0.15 |
|   | Unknown Impurity at RRT 1.35 | <0.15 |
|   | Individual unknown impurities ≥0.05% on RRT basis | <0.15 |
|   | Total impurities | <0.30 |
| 5 | Water content by KF (% w/w) | Not More than 7 |
| 6 | Residual solvents by GC-HS (ppm): | |
|   | Method-I | |
|   | Methanol | Not more than 3000 |
|   | Ethanol | Not more than 5000 |
|   | Dichloromethane | Not more than 600 |
|   | Methyl tert-butyl ether | Not more than 5000 |
|   | Hexanes | Not more than 290 |
|   | n-Heptane | Not more than 5000 |
|   | Toluene | Not more than 890 |
|   | Method-II | |
|   | Ethyl acetate | Not more than 5000 |
|   | Diisopropyl ether | Not more than 1500 |
|   | Diisopropylethylamine | Not more than 1500 |
|   | Triethylamine | Not more than 5000 |
| 7 | Water content by KF (% w/w) | Between 4.7 to 7.0 |

Example 10: Stability of Monohydrate Form

NYX-2925 monohydrate drug substance was placed on stability for 6 months at 40° C./75% relative humidity and for 12 months at 25° C./60% relative humidity; there were no significant changes in the impurity profile or other quality attributes such as appearance, assay, water content, microbial examination, and XRPD.

NYX-2925 monohydrate drug product was formulated with the pharmaceutically acceptable excipients: microcrysglobal improvement, and to assess the safety and tolerability of multiple dose levels of NYX-2925.

The study was a 6- to 9-week study, including a 1- to 4-week Screening Period, followed by a 4-week double-blind, randomized, placebo-controlled Treatment Period, and a 1-week Follow-Up Period.

Screening Period (Week −4 to −1)

The subjects were asked to provide informed consent for this study before any required procedures were performed. Subjects were also required to sign an additional consent for their inclusion in a subject registry database. The database used partially-identified subject information to review subjects' research study history within a proprietary, secure platform.

Subjects who met any of the following criteria were not eligible for continued screening: current enrollment in another study, concurrent screening at another research site, violation of the required number of half-lives since the last research study, violation of the washout period between studies, or incorrect age for the NYX-2925-2001 study. Employees, contractors, and volunteers of the study site, or relatives of any employees, contractors, and volunteers of the study site were not eligible to participate.

Subjects with Type 2 diabetes who had been on stable antidiabetic medication for at least 1 month (or had stable glycemic control with diet and exercise alone) and who had been suffering from painful diabetic peripheral neuropathy in the lower extremities for at least 6 months but not more than 10 years were screened for diabetic peripheral neuropathy using the Michigan Neuropathy Screening Instrument and the Masquerading Disorders Tool. Subjects must have had a score of ≥4 and ≤9 on the 11-point Numerical Rating Scale (NRS) for average pain over the past 24 hours at Visit 1.

Subjects were assessed for widespread pain symptoms using the American College of Rheumatology Fibromyalgia Criteria. Additional procedures during Visit 1 included the administration of the Hospital Anxiety and Depression Scale (HADS), completion of the Sheehan Suicidality Tracking Scale (S-STS), adverse event collection which began at the time of informed consent, demographic characteristics, medical history including concomitant medications, complete physical examination (with comprehensive neurological examination), 5-minute electrocardiogram, vital signs (sitting blood pressure and pulse), height, body weight, and collection of blood and urine samples for chemistry, Human immunodeficiency virus (HIV), hepatitis, triglycerides, hematology (including HbA1c), and urinalysis. All subjects underwent urine drug and alcohol screen using a local urine testing kit and breathalyzer, respectively. Subjects who tested positive for marijuana, opioids, benzodiazepines inconsistent with current prescriptions, or alcohol were not allowed to continue in the study. Female subjects of childbearing potential were tested for pregnancy using a local urine testing kit and were counseled to begin or continue using highly effective contraception.

Eligible subjects who met all entry criteria entered a 1- to 4-week Screening Period, during which they discontinued all except 1 (if applicable) of their pharmacologic analgesic treatments for neuropathic pain associated with diabetic peripheral neuropathy, and complete daily pain diaries. The duration of the Screening Period depended upon the analgesic treatment that is being discontinued. The only allowed analgesics for painful diabetic peripheral neuropathy were not an N-methyl-D-aspartate receptor ligand, were required to be non-opioid and non-sedative, and must not interfere with subjects' pain reporting. The allowed analgesics were required to have been taken for at least 1 month (30 days) prior to Visit 1, and subjects were required to be on a stable fixed dose that was not expected to change during the study. Subjects who were already taking no more than 1 allowed concomitant analgesic medication at Visit 1 could directly begin Week −1 of the Screening Period.

During Visit 1, eligible subjects were provided a handheld device, and as a method for ensuring consistency and reliability of pain scoring, subjects were instructed at Visits 1 through 3 on how to record their pain on the device. Subjects were also educated at Visits 1 through 3 on appropriate expectations around their participation in a clinical study and the importance of consistently and accurately reporting their pain throughout the study. Review of these educational materials could be repeated for some or all subjects depending on findings of an ongoing blinded data review (e.g., if pain score variability is increased on a subject or site level).

Subjects were dispensed acetaminophen to be used as rescue medication, and were instructed to take no more than 2 g/daily (one to two 500-mg caplets every 4 to 6 hours as needed) for DPN pain. Beginning immediately after Visit 1, pain intensity and rescue medication use were recorded in the study-issued handheld device daily at bedtime. Subjects entered their average pain intensity, worst pain intensity, pain on walking, and whether rescue medication was used during the past 24 hours. Pain intensity was recorded using an 11-point NRS, with 0 being no pain and 10 being the worst pain imaginable. Every morning upon awakening, subjects completed the Daily Sleep Interference Scale (DSIS) via their study-issued handheld device.

Screening Period (Week −1)

The investigative site staff contacted study subjects by telephone weekly through Week −1 to reinforce the reporting instructions (i.e., diary completion), and to assess adverse events. Subjects were asked a non-leading question to inquire about potential adverse events, "Have you experienced any new or changed symptoms since we last asked/since last week?" Subjects taking no more than 1 allowed concomitant analgesic medication at Visit 1 directly began Week −1 of the Screening Period.

Baseline Visit (Week 0)

At Visit 2 (Baseline Visit), study personnel verified eligibility with the inclusion and exclusion criteria when the subjects were on site, and prior to randomization. Pain scores reported by subjects during the Screening Period were evaluated by the interactive response technology system for raw score and for variability among scores after transmission of pain scores from the handheld devices to determine randomization eligibility. The interactive response technology system notified the site if the subject was "Eligible" or "Not eligible." No other information was provided.

Subjects whose mean of the daily average pain intensity score during the preceding 7 (±1) days was within the protocol-defined algorithm and whose compliance with daily diary completion was at least 85% (≥6 of 7 days in a week) were eligible for randomization. The absolute pain score and variability among scores, as well as the actual percentage required for diary compliance, were masked to investigators and subjects. Subject eligibility for randomization into the study based on these variables was communicated to the investigator via the interactive response technology system.

Subjects were again asked a non-leading question to assess potential adverse events. Use of concomitant medications was documented. Vital signs (blood pressure and pulse) were measured after sitting for 5 minutes and a 5-minute electrocardiogram was performed. Medical history was updated, and a brief physical examination performed. Blood and urine samples were collected for chemistry, hematology, and urinalysis testing. Subjects underwent drug and alcohol screen using a local urine testing kit and breathalyzer, respectively. Subjects who tested positive for marijuana, opioids, benzodiazepines inconsistent with current prescriptions, or alcohol, were not allowed to continue in the study. Female subjects of childbearing potential were tested for pregnancy using a local urine testing kit and were counseled to continue using highly effective contraception.

Eligible subjects were randomized to receive either NYX-2925 10 mg daily, NYX-2925 50 mg daily, NYX-2925 200 mg daily, or placebo for 4 weeks in a 1:1:1:1 allocation. Investigators and subjects were masked to the randomization allocation. Subjects were dispensed a 2-week supply of investigational product and instructed to take 2 capsules by mouth once daily. Subjects were also re-dispensed acetaminophen to use as rescue medication for DPN pain; instructions not to exceed 2 g/day were reinforced. The appropriate use of rescue medication was assessed by inventory of the returned caplets, as well as by subject interview.

Subjects were instructed to continue entering their average pain intensity, worst pain intensity, pain upon walking, and whether they used rescue medication over the past 24 hours into their study-issued handheld devices every night. Every morning upon awakening, subjects completed the DSIS via their study-issued handheld device. Pain diary compliance was reviewed at each study visit by the study staff, and reporting instructions was reinforced.

Quantitative sensory testing was done using the Bedside Sensory Testing Kit. The following scales were completed at the Baseline Visit: Brief Pain Inventory for Diabetic Peripheral Neuropathy (BPI-DPN), the Short-Form McGill Pain Questionnaire version 2 (SF-MPQ-2), the Norfolk Quality of Life Questionnaire-Diabetic Neuropathy (QOL-DN), the HADS, the Insomnia Severity Index, and the S-STS.

One week following the Week 0 visit, subjects were contacted by telephone for an assessment of adverse events and to reinforce diary completion. Adverse events were assessed by asking the subject a non-leading question.

Treatment Period: Week 2

Subjects returned to the clinic at the end of Week 2 for assessment of compliance with study medication, use of rescue medication, and were dispensed the final 2-week supply of investigational product and rescue medication for DPN pain. Pain diary compliance was reviewed by the study staff, and reporting instructions were reinforced. Adverse events were assessed by asking the subjects a non-leading question. Use of concomitant medications was documented. Vital signs (sitting blood pressure and pulse) were measured. Blood samples were collected for liver function testing. Female subjects of childbearing potential were counseled to continue using highly effective contraception. Subjects were instructed to continue entering their average pain intensity, worst pain intensity, pain upon walking, and rescue medication use over the past 24 hours into their study-issued handheld devices every night. Every morning upon awakening, subjects completed the DSIS via their study-issued handheld device. Scales to be completed at the Week 2 visit included the Patient Global Impression of Change (PGI-C), the S-STS, and the Insomnia Severity Index. One week following the Week 2 visit, subjects were contacted by telephone for an assessment of adverse events and to reinforce diary completion.

Treatment Period: Week 4/Early Termination

During the Week 4 or Early Termination Visit, subjects were evaluated for compliance with study medication, and returned all materials and unused study medication/rescue medication to the study site. The study-issued handheld device was returned. Pain diary compliance was reviewed by the study staff. Adverse events were assessed by asking the subjects a non-leading question. Use of concomitant medications was documented. Vital signs (sitting blood pressure and pulse) and body weight was measured, brief physical examination performed, and subjects underwent a 5-minute electrocardiogram. Blood and urine samples were collected for chemistry, hematology, and urinalysis testing. Female subjects of childbearing potential were tested for pregnancy using a local urine testing kit. Subjects underwent drug and alcohol screen using a local urine testing kit and breathalyzer, respectively. Scales completed at the Week 4/Early Termination Visit included BPI-DPN, PGI-C, SF-MPQ-2, HADS, QOL-DN, Insomnia Severity Index, and S-STS.

7 Days Post-Treatment Follow Up Visit (Week 5)

Subjects returned to the study site 7 days following the Week 4/Early Termination visit to assess adverse events and concomitant medication use. The adverse event assessment included any serious adverse events that were ongoing at the time of study completion, and whether any ongoing adverse events had progressed to becoming serious. Blood samples were collected for liver function testing.

Number of Subjects (Planned and Analyzed)

Approximately 300 subjects enrolled in a randomized 1:1:1:1 method with approximately 75 subjects per treatment arm.

Diagnosis and main criteria for inclusion included the following.

Inclusion Criteria: Screening

1. An Institutional Review Board-approved written informed consent and privacy language (Health Insurance Portability and Accountability Act) authorization must be obtained from the subject prior to performing any study related procedures.
2. Subjects who consented to being included in a subject registry database.
3. Male and female subjects ≥18 and ≤75 years of age.
4. Subjects with a diagnosis of Type 2 Diabetes.
5. Subjects with a score of ≥4 and ≤9 on the 11-point NRS for average pain intensity over the past 24 hours at Visit 1.
6. Hemoglobin A1c (HbA1c)≤11% (measured at Visit 1).
7. Stable use of diabetic medications beginning 1 month prior to Visit 1. (Adequate glycemic control with diet and exercise alone is also permitted.)
8. Subjects with diabetic peripheral neuropathy, of symmetrical nature and in lower extremities for ≥6 months to ≤10 years, and diagnosed by a score of ≥3 on Michigan Neuropathy Screening Instrument.
9. Body mass index <40 kg/m2.
10. Calculated creatinine clearance ≥60 mL/minute (Cockcroft-Gault formula).
11. Clinical laboratory values must be within normal limits, or deemed not clinically significant by the investigator and sponsor-designated medical monitor.
12. Female subjects must either:
    Be of non-childbearing potential:
    Post-menopausal (defined as at least 1 year without any menses) prior to Visit 1; or
    Documented as surgically sterile.
    Or, if of childbearing potential:
    Agree not to try to become pregnant during the study and for 28 days after the final administration of investigational product;
    Have a negative urine pregnancy test at Visit 1; and
    If heterosexually active, agree to consistently use 2 forms of highly effective birth control (at least 1 of which must be a barrier method) starting at Visit 1 and continuing throughout the study period and for 28 days after the final administration of investigational product.

13. Female subjects must agree not to breastfeed starting at Visit 1 and continuing throughout the study period and for 28 days after the final administration of investigational product.
14. Female subjects must not donate ova starting at Visit 1 and continuing throughout the study period and for 28 days after the final administration of investigational product.
15. Male subjects must refrain from sperm donation starting at Visit 1 and continuing throughout the study period and for 90 days after the final administration of investigational product.
16. Male subjects who are not surgically sterilized for at least 90 days, and sexually active with a female partner, must use a condom with spermicide during the study, and for 90 days after the last dose of investigational product.
17. Has not participated in an interventional study for at least 30 days. Agrees not to participate in another interventional study while on treatment. Eligibility was reviewed during the study via sponsor participation in a research subject database.
18. Ability to understand the requirements of the study, abide by the study restrictions, as well as concomitant medications exclusions, and agree to return for the required assessments.

Inclusion Criteria: Randomization

Patients were included if diary compliance and daily pain score reporting was within the protocol defined range during the 7 days prior to randomization. Waivers to the inclusion criteria were not allowed.

Exclusion Criteria

1. Subjects who have a current diagnosis of a major psychiatric disorder (including schizophrenia, bipolar disorder, or panic disorder), including those who have required an antipsychotic or mood stabilizer (e.g., lithium, carbamazepine, valproate) for a psychiatric condition in the past year, or subjects who have had a major depressive episode (MDE) in the past 6 months. Subjects with major depressive disorder (MDD) or generalized anxiety disorder (GAD) who have been on stable medication for the past 3 months (and are expected to remain stable for the duration of the trial) and whose condition is currently well-controlled may be included.
2. Subjects who have pain that cannot be clearly differentiated from, or could interfere with the assessment of peripheral diabetic neuropathy, as measured by the Masquerading Disorders Tool at Visit 1.
3. Neurologic disorders unrelated to diabetic neuropathy (e.g., phantom limb from amputation), skin condition in the area of neuropathy that could alter sensation (e.g., plantar ulcer), or other painful conditions (e.g., arthritis) that, in the judgment of the investigator, could interfere with reporting of pain due to diabetic neuropathy.
4. History of hypoglycemia that disturbed consciousness, or ketoacidosis requiring hospitalization within past 3 months.
5. Subjects with history of severe renal impairment defined by renal dialysis or peritoneal dialysis, or who have undergone renal transplant.
6. Impaired hepatic function characterized by a previous known diagnosis of chronic liver disease, and/or the presence of abnormal serum total bilirubin, or alanine transaminase (ALT), aspartate transaminase (AST), or alkaline phosphatase >1.5×upper limit of normal (ULN) at screening.
7. Known history of significant cardiovascular condition, such as myocardial infarction or congestive heart failure; evidence of current uncontrolled cardiac arrhythmias, angina, or electrocardiographic evidence of acute ischemia; or active conduction system abnormalities; QTcF>450 msec (males) or >470 msec (females), or uncontrolled hypertension characterized by resting systolic blood pressure >140 mm Hg or resting diastolic >90 mm Hg.
8. Heart rate <45 bpm or >90 bpm.
9. Fasting triglycerides >250 mg/dL.
10. History of Huntington's disease, Parkinson's disease, Alzheimer's disease, Multiple Sclerosis, or a history of seizures, epilepsy, or strokes.
11. HIV infection, hepatitis, or other ongoing infectious disease that the investigator considers clinically significant.
12. Concomitant use of antiepileptic drugs, non-steroidal anti-inflammatory drugs (except cardiac preventive acetylsalicylic acid), opioids, muscle relaxants, dextromethorphan (except low dose intermittent use for cough), tramadol, topical lidocaine, topical capsaicin, and selective norepinephrine reuptake inhibitors. Subjects are allowed to enter with a maximum of 1 allowed analgesic medication for neuropathic pain that has been taken at a stable dose for at least 1 month (30 days) prior to Visit 1. Allowed analgesics may not be N-methyl-D-aspartate receptor ligands, must be non-opioid and non-sedative, and must not interfere with the subjects' pain reporting. Tricyclic antidepressants may be continued if designated as the single analgesic medication for the treatment of pain.
13. History of or current substance abuse disorder as defined by Diagnostic and Statistical Manual of Mental Disorders—Fifth Edition.
14. Recreational and/or medicinal marijuana use within the past 6 months.
15. Positive urine drug screen for marijuana, opioids, benzodiazepines inconsistent with current prescriptions, or breathalyzer test for alcohol at Visit 1.
16. Positive urine drug screen for marijuana, opioids, benzodiazepines inconsistent with current prescriptions, or breathalyzer test for alcohol at Visit 2.
17. Sensitivity to, allergy to, or concomitant use of N-methyl-D-aspartate receptor ligands including ketamine, amantadine, dextromethorphan (except low dose intermittent use for cough), memantine, methadone, dextropropoxyphene, and/or ketobemidone.
18. Amputations of lower extremities (toe amputation is allowed).
19. Any condition, including serious medical conditions that could interfere with the ability of the subject to participate in the study or could confound study assessments.
20. Subjects with hypersensitivity to multiple medications, in the opinion of the investigator.

21. Subjects who meet the criteria for suicidal intent, plan and/or behavior by scoring 3 or 4 on Questions 2 or 13, or 2 or higher on any Question 1a (only if 1b is coded YES), 3, 4, 5, 6, 7, 8, 9, 10, 11, 12, or 14 based on the S-STS at Visit 1 or Visit 2.

Waivers to the exclusion criteria were not allowed.

Dosing and Administration

The study was a double-blind study. Subjects, study personnel, and the sponsor were blinded to study treatment. Subjects were dispensed blinded investigational product according to the randomization schedule. Investigational product was dispensed at the Week 0 (Baseline) and Week 2 visits; at each of the 2 visits, subjects received a 2-week supply of investigational product. Capsule strengths were 10 mg, 50 mg, and 100 mg. Subjects were instructed to take 2 capsules of investigational product once daily by mouth, in order to maintain study blinding.

There were 4 treatment groups:
10 mg of N X-2925 by mouth once daily for 4 weeks
50 mg of NYX-2925 by mouth once daily for 4 weeks
200 mg of NYX-2925 by mouth once daily for 4 weeks
Placebo by mouth once daily for 4 weeks Subjects were also dispensed 1 bottle of acetaminophen to be used as rescue medication. Rescue medication consisted of 500 mg caplets of acetaminophen. Subjects were instructed that up to 2 g/day of rescue medication was allowed and should be reported daily via their study-issued handheld device.

Investigational Product Description, Appearance, Packaging, and Labeling

NYX-2925 is a small molecule that was provided as capsules for oral administration in strengths of 10 mg, 50 mg and 100 mg NYX-2925 per capsule. Matching placebo capsules were also provided.

The oral formulation of the investigational product comprises inert United States Pharmacopeia (USP)-grade excipients in a capsule made of hydroxyl-propyl cellulose. The content of the capsule is a dry blend of NYX-2925, microcrystalline cellulose, National Formulary (NF), pregelatinized starch, NF, and magnesium stearate USP. Matching placebo capsules contained only the inactive ingredients listed previously.

The investigational product was provided in a blister-pack kit. The labels included "NYX-2925 Oral Capsules or Placebo to Match", capsule count, kit number, storage conditions, retest date, sponsor name, and investigational use statement. Each kit of investigational product included 18 capsules (nine 2-capsule rows) of either matching placebo capsules or 10 mg, 50 mg, or 100 mg NYX-2925 capsules according to the randomization schedule. The investigational product was packaged in a way that each dose will be 2 capsules/row, with the following blinded configuration:
10 mg dose: 1 capsule was placebo and 1 capsule was 10 mg strength
50 mg dose: 1 capsule was placebo and 1 capsule was 50 mg strength
200 mg dose: 2 capsules were 100 mg strength Study of NYX-2925 in Patients with Painful Diabetic Peripheral Neuropathy (DPN)

Key objectives of the study were to evaluate safety and tolerability of NYX-2925 in a DPN patient population, assess the most active dose level across a 20-fold dose range, assess activity of NYX-2925 across multiple endpoints relevant to chronic pain, and identify key patient characteristics to inform inclusion/exclusion criteria for future studies.

Figure 8A:
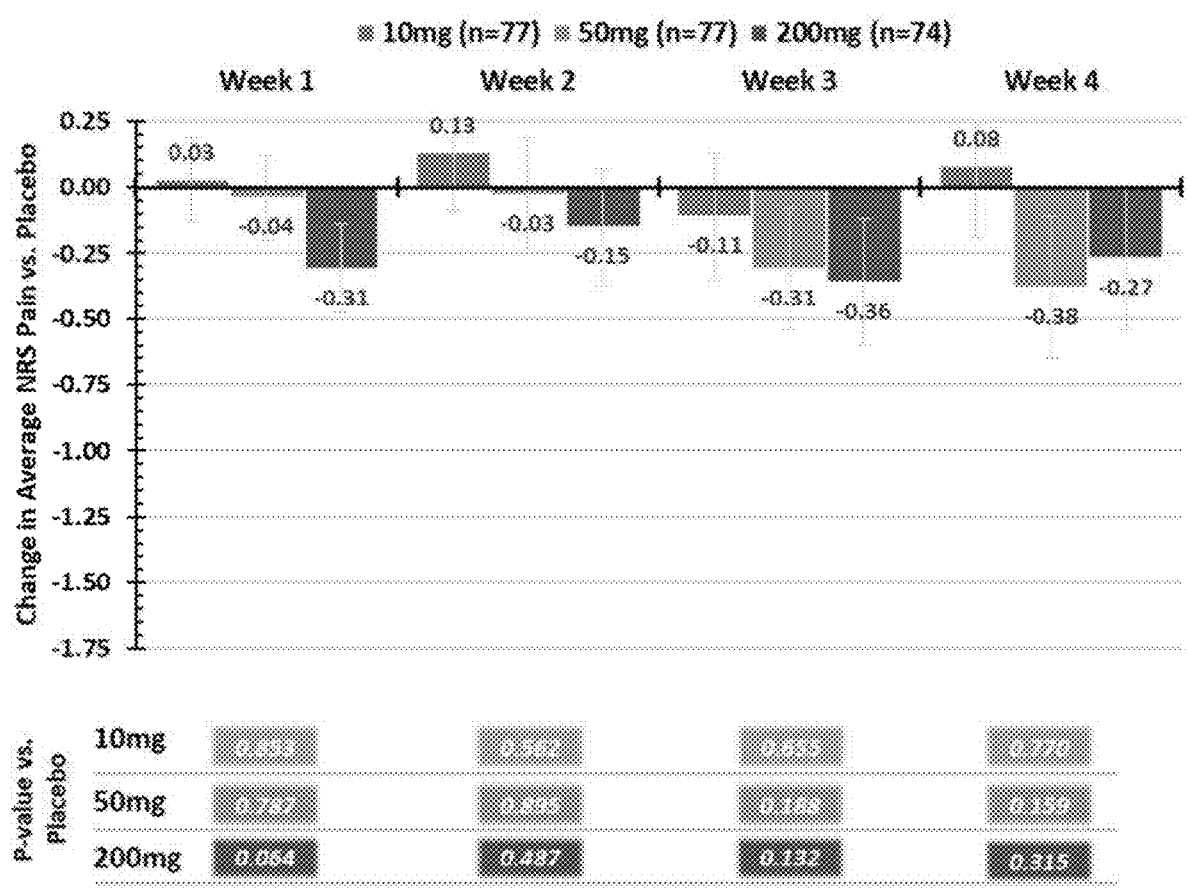
FIG. 8A is a graph of change in average daily pain for patients administered NYX-2925 vs. placebo (total population, n=300) (where the 10 mg bar is on the left, the 50 mg bar is in the middle, and the 200 mg bar is on the right).
Figure 8B:
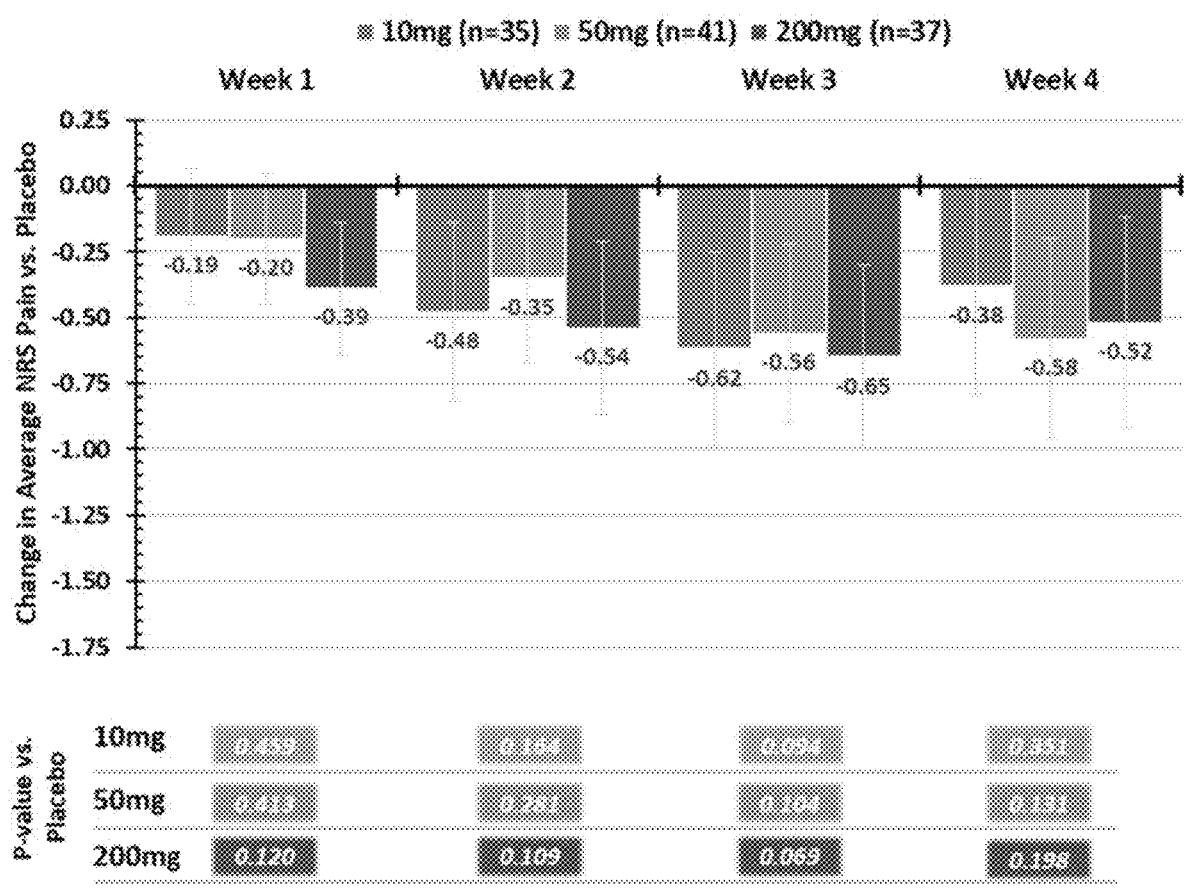
FIG. 8B is a graph of change in average daily pain for patients administered NYX-2925 vs. placebo for patients not using concomitant analgesic (n=148) (where the 10 mg bar is on the left, the 50 mg bar is in the middle, and the 200 mg bar is on the right).

NYX-2925 showed numeric, but not statistically significant, separation from placebo on the primary endpoint in the total patient population (FIG. 8A) and in patients not on a concomitant analgesic (FIG. 8B). Patients not on a concomitant analgesic showed much greater separation from placebo.

Figure 9A:
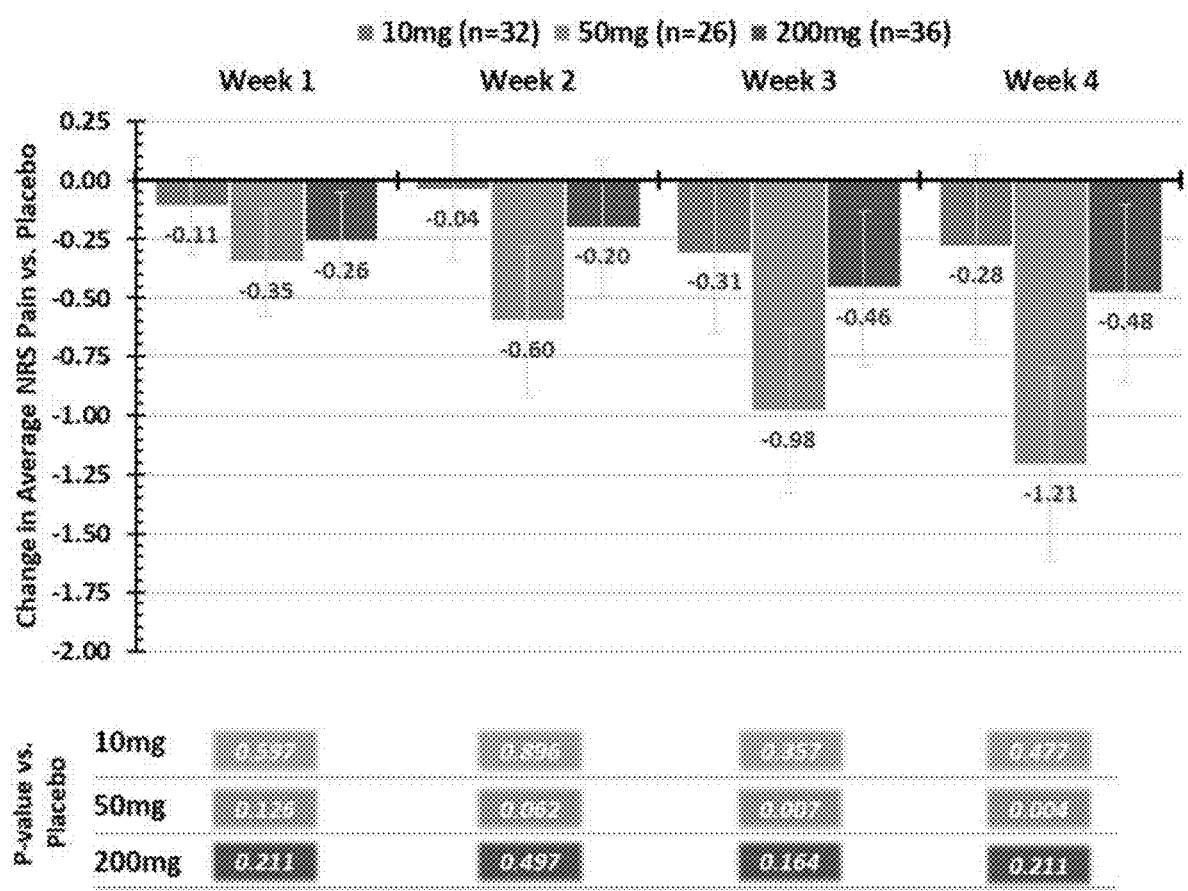
FIG. 9A is a graph of change in average daily pain for patients administered NYX-2925 vs. placebo (post-hoc analysis of advanced DPN population for patients who have had DPN for ≥4 years, n=127) (where the 10 mg bar is on the left, the 50 mg bar is in the middle, and the 200 mg bar is on the right).
Figure 9B:
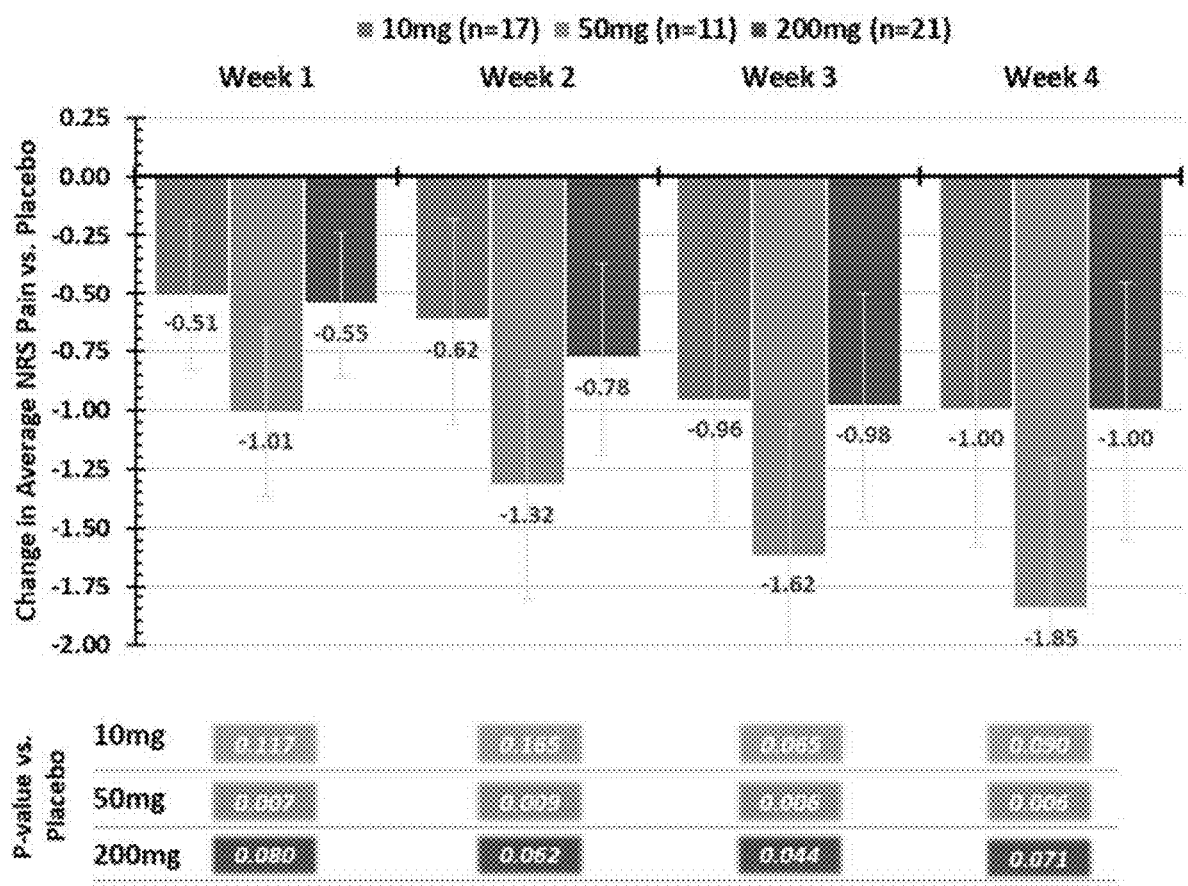
FIG. 9B is a graph of change in average daily pain for patients administered NYX-2925 vs. placebo for patients not using concomitant analgesic (post-hoc analysis of advanced DPN population for patients who have had DPN for ≥4 years, n=64) (where the 10 mg bar is on the left, the 50 mg bar is in the middle, and the 200 mg bar is on the right).

NYX-2925 showed significant effects in patients with advanced DPN, a large and mechanistically relevant patient sub-population (FIG. 9A). NYX-2925 exhibited robust and consistent effects across primary and secondary endpoints in patients with advanced DPN. This was also true for a subset of advanced DPN patients with no concomitant analgesic medication
(FIG. 9B).

Figure 10A:
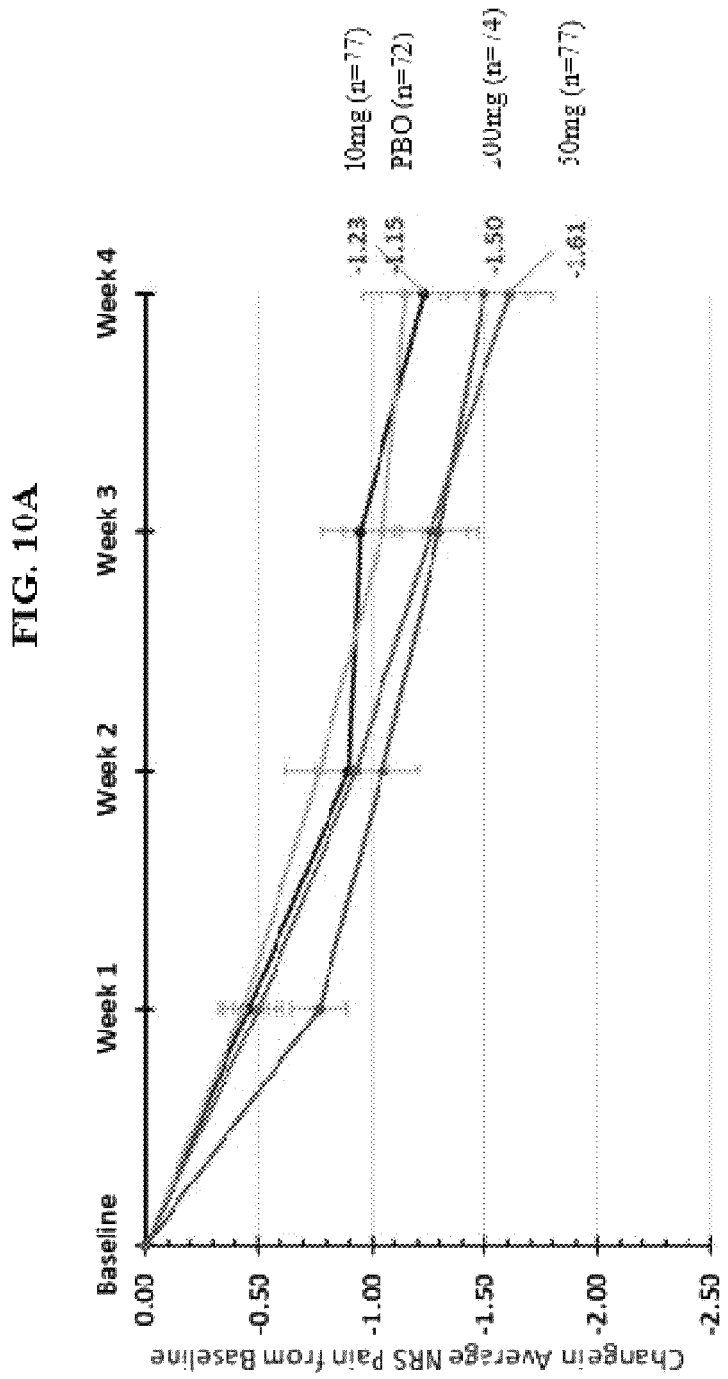
FIG. 10A is a graph of change in average daily pain for patients administered NYX-2925 vs. placebo (total population).
Figure 10B:
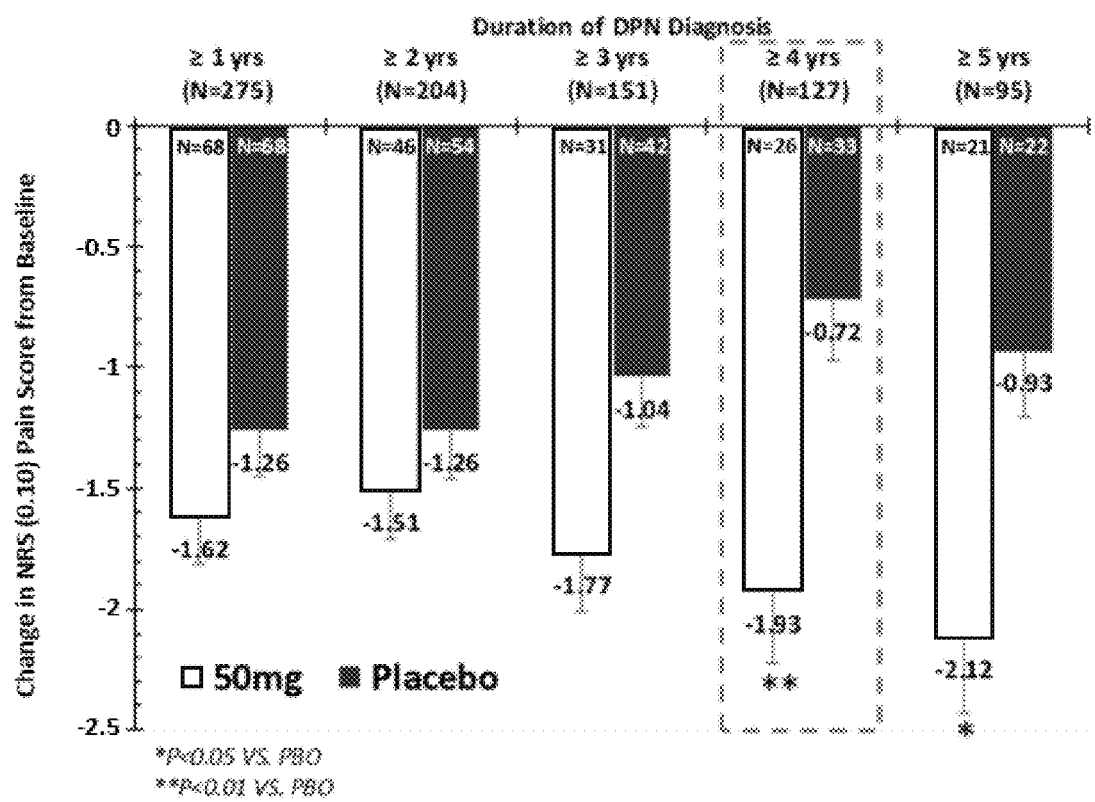
FIG. 10B is a graph of change in average daily pain (from baseline to week 4) for patients administered NYX-2925 vs. placebo broken down by duration of painful DPN (where 50 mg bar is on the left and the placebo (PBO) bar is on the right).

The large and highly relevant sub-population was identified based on mechanistic understanding and time-course of "chronification," i.e., grouping by years of chronic pain. The change in daily pain for the total patient population is shown in FIG. 10A. In contrast, the change in average daily pain from baseline to week 4 is shown for the 50 mg dose and placebo in FIG. 8B for patient groups based on how many years they have suffered painful DPN. The earlier groups include the patients in the later groups, such that the 275 patients in the ≥1 yrs groups includes the patients in the ≥2 yrs, ≥3 yrs, ≥4 yrs, and ≥5 yrs groups. The change from placebo becomes more marked for the patients who have suffered from painful DPN for longer periods, and becomes most significant at ≥4 years. As pain shifts from primarily peripheral sensory processing to more pronounced central manifestation, greater effects are observed with NYX-2925.

Figure 11A:
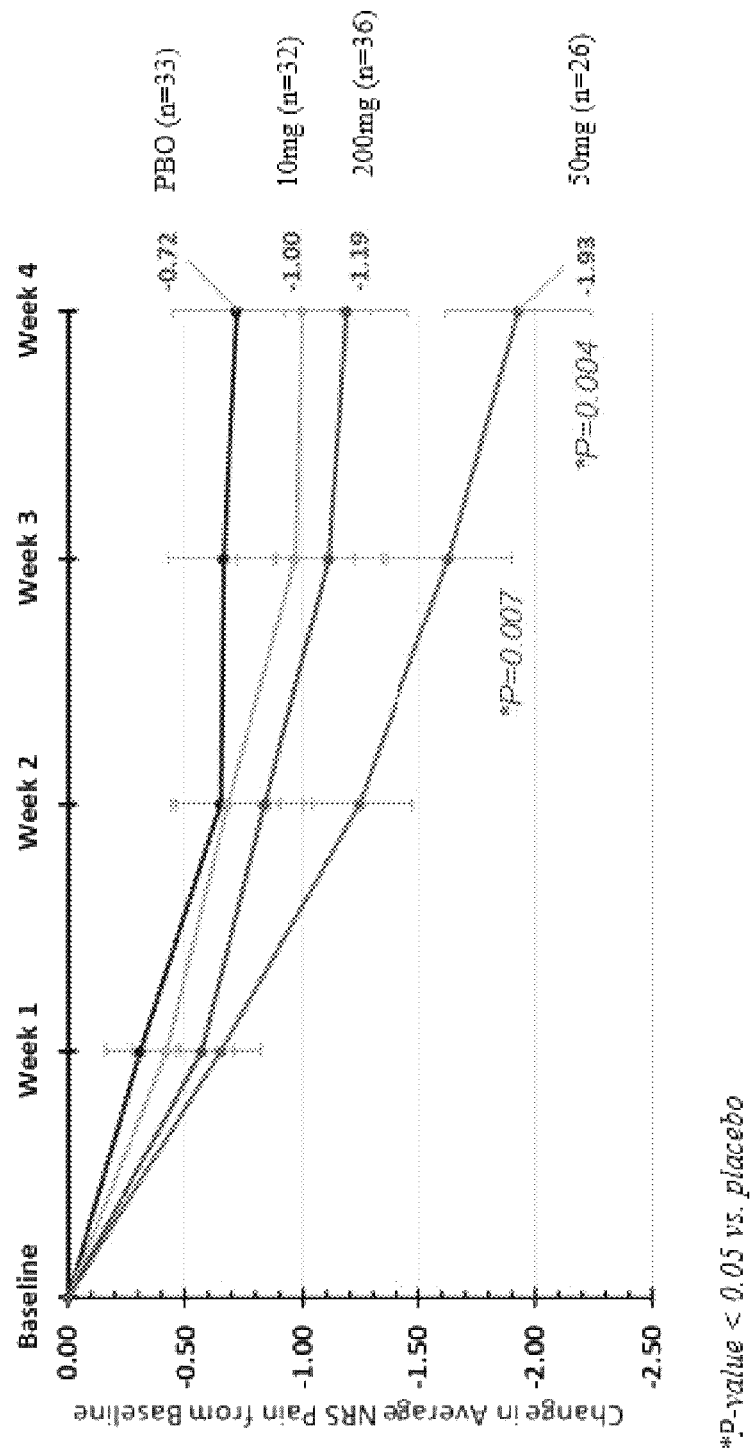
FIG. 11A is a graph of change in average daily pain (NRS) for patients administered NYX-2925 vs. placebo for patients with advanced DPN (post-hoc analysis of advanced DPN population for patients who have had DPN for ≥4 years, n=127).
Figure 11B:
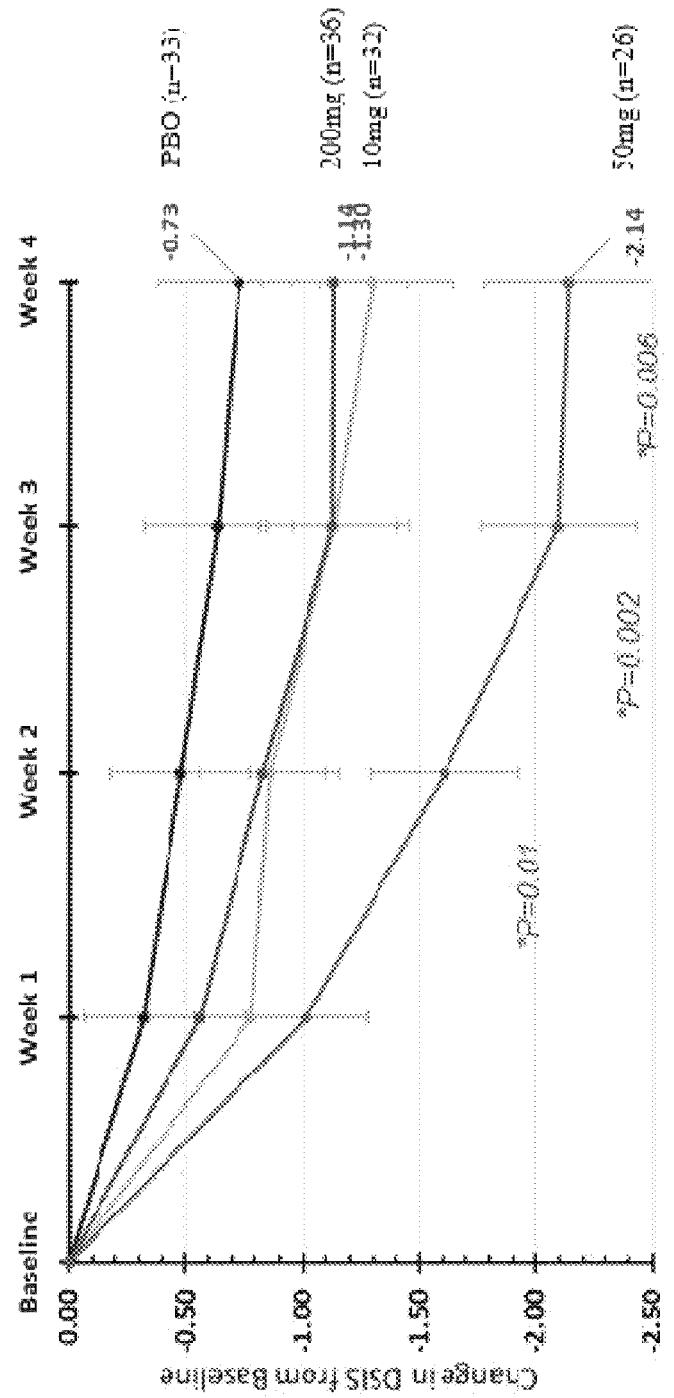
FIG. 11B is a graph of change in daily sleep interference score for patients administered NYX-2925 vs. placebo for patients with advanced DPN (post-hoc analysis of advanced DPN population for patients who have had DPN for ≥4 years).
Figure 11C:
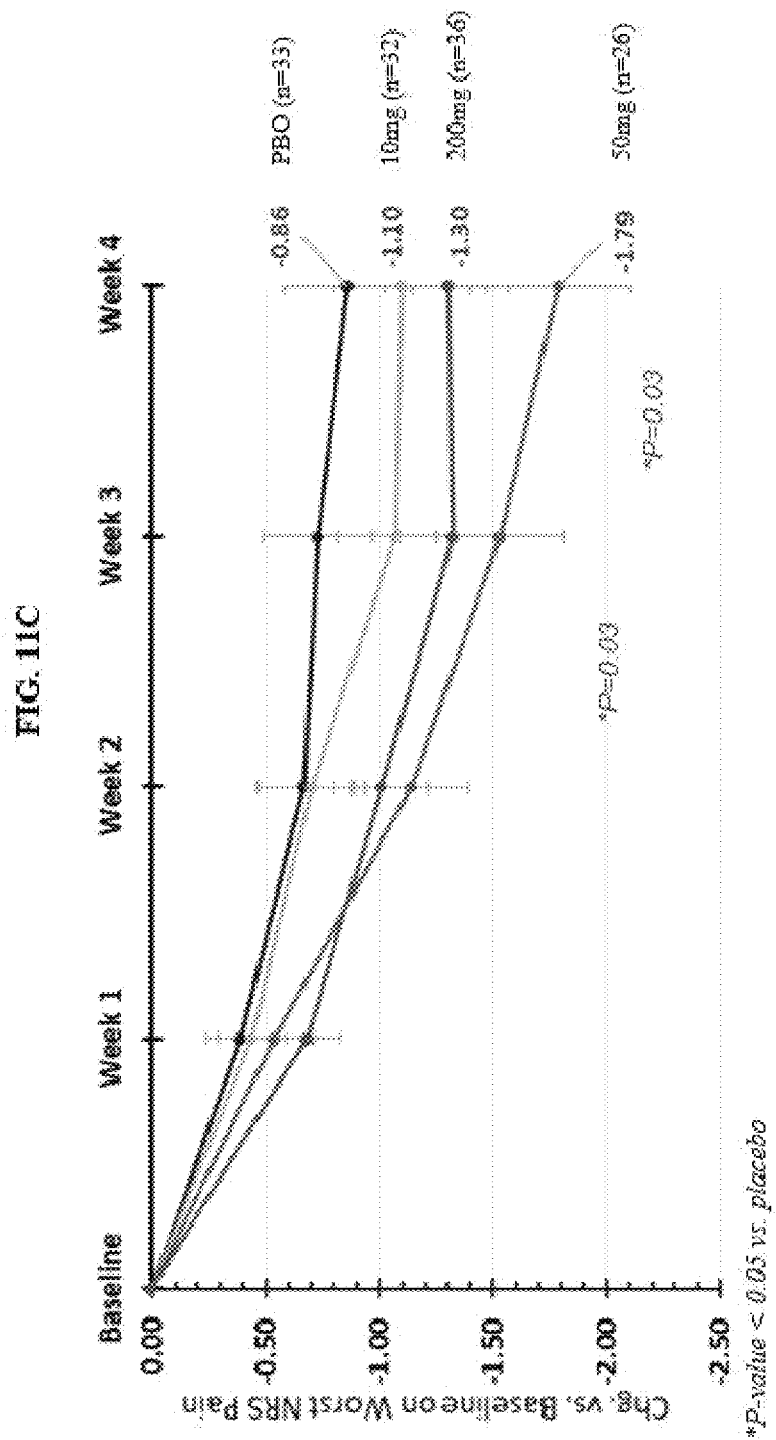
FIG. 11C is a graph of change in worst pain (NRS) from baseline for patients administered NYX-2925 vs. placebo for patients with advanced DPN (post-hoc analysis of advanced DPN population for patients who have had DPN for ≥4 years).
Figure 11D:
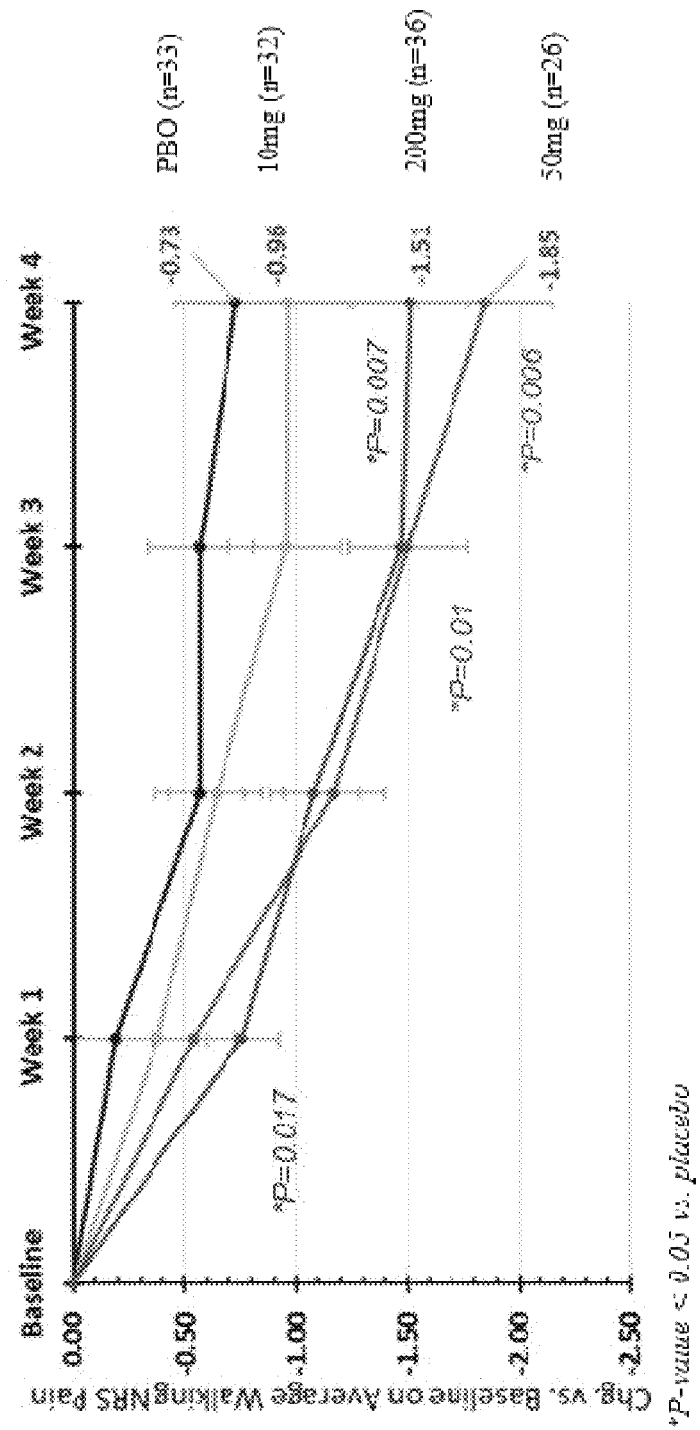
FIG. 11D is a graph of change in pain on walking (NRS) from baseline for patients administered NYX-2925 vs. placebo for patients with advanced DPN (post-hoc analysis of advanced DPN population for patients who have had DPN for ≥4 years).

When looking only at the advanced DPN population of patients who have had DPN for at least 4 years, dosing of NYX-2925 showed significant effects across primary and secondary endpoints. There was improvement in change in average pain (NRS) from baseline (FIG. 11A), change in daily sleep interference score from baseline (FIG. 11B), change in worst pain from baseline (FIG. 11C), and change in pain on walking (NRS) score from baseline (FIG. 11D). Statistical significance for the 50 mg dose was found at least at the 3 and 4 week points for change in average pain, and also at least at the 2, 3 and 4 week points for daily sleep interference.

Figure 12:
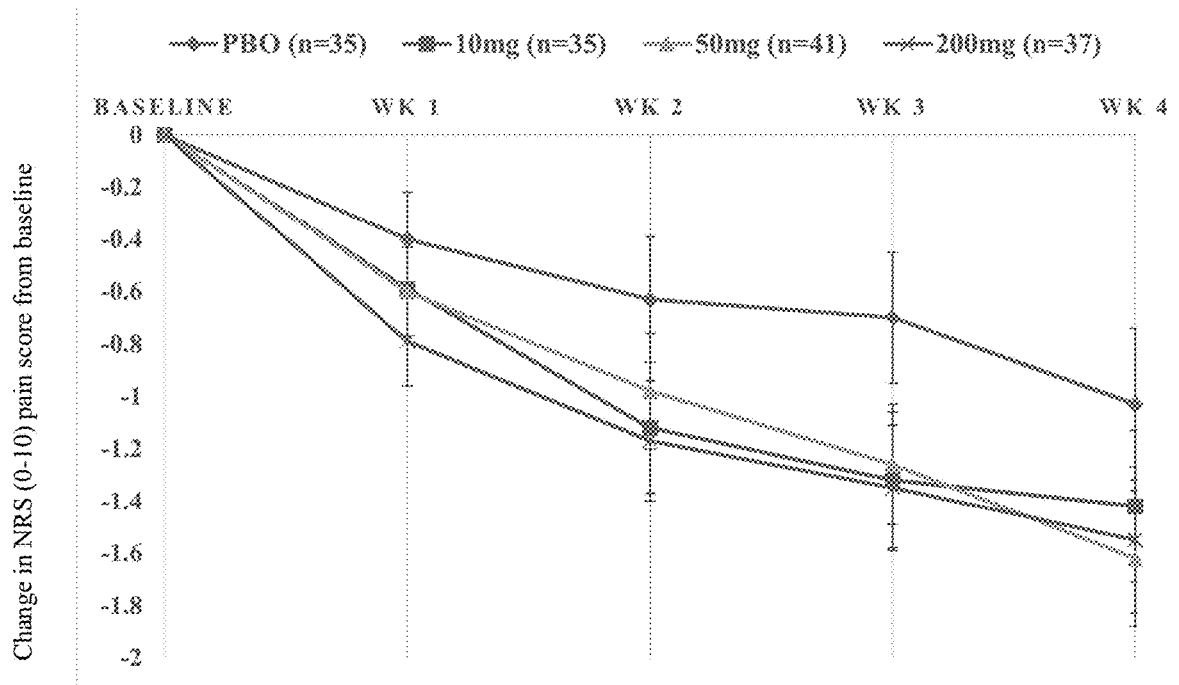
FIG. 12 is a graph of MMRM change in average daily pain for patients administered NYX-2925 vs. placebo for patients not using concomitant analgesic (error bars reflect standard error of mean, n=148).

For the effect of lack of concomitant analgesic use, the effect of NYX-2925 on MMRM change in average daily pain for subjects not using analgesic is shown in FIG. 12.

Figure 13:
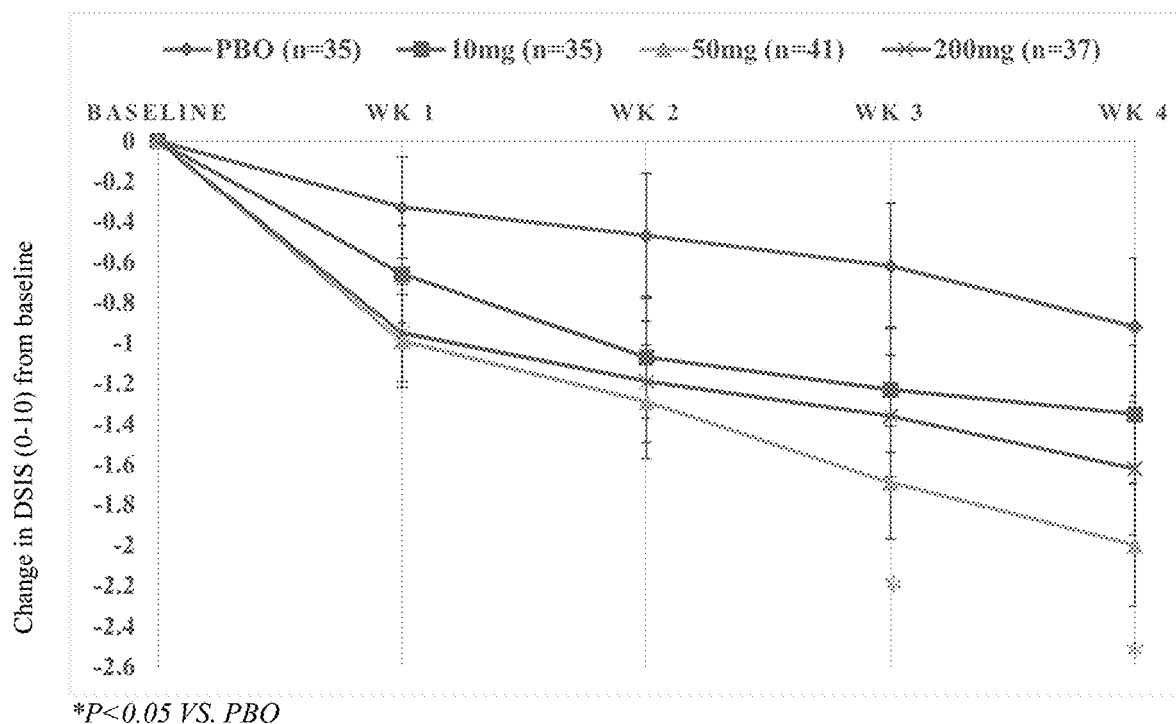
FIG. 13 is a graph of MMRM change in daily sleep interference score for patients administered NYX-2925 vs. placebo for patients not using concomitant analgesic for patients administered NYX-2925 vs. placebo for patients not using concomitant analgesic (error bars reflect standard error of mean, n=148).

The effect of NYX-2925 on MMRM change in daily sleep interference for subjects not using analgesic is shown in FIG. 13, with significance for the 50 mg dose at the 3 and 4 week points.

Other secondary endpoints for the effect of NYX-2925 in patients with at least 4 years of DPN duration is shown in FIG. 14. Improvement is shown for total pain score, insomnia severity, pain severity, pain interference, quality of life, and patient global impression of change (PGI-C).

Summary of Results

NYX-2925 was safe and well tolerated in the study, with no SAEs and an overall AE profile comparable to placebo.

Patients with DPN who were administered NYX-2925 experienced meaningful pain alleviation after four weeks. Patients with advanced DPN showed the greatest treatment benefit.

Mechanism of NYX-2925 treatment addresses the increasing central manifestation of pain perception and processing associated with the prolonged chronic pain these patients experience.

Patients with advanced DPN represented nearly half of the entire study population (N=127).

The 200 mg and 50 mg doses of NYX-2925 showed meaningful separation from placebo. The 50 mg dose was identified as the most active (effective) dose level among the three doses tested.

Evidence of inverted-U-shaped dose response was seen.

In patients with advanced DPN, effect of the 50 mg dose was robust and clinically meaningful. Week 4 change vs. baseline in average daily pain (on 10-point NRS) was 1.93 points. Week 4 change vs. placebo in average daily pain (on 10-point NRS) was 1.21 points (p=0.004).

Robust improvements were consistent across primary and secondary endpoints.

Use of concomitant analgesic does not appear to affect treatment benefit of NYX-2925. However, treatment effects were even more pronounced in patients not on a concomitant analgesic medication.

INCORPORATION BY REFERENCE

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A crystalline form of (2S,3R)-3-hydroxy-2-((R)-5-isobutyryl-1-oxo-2,5-diazaspiro[3.4]octan-2-yl)butanamide monohydrate ("NYX-2925"), wherein the crystalline form of NYX-2925 monohydrate is characterized by a powder X-ray diffraction pattern comprising characteristic peaks at the following diffraction angles in degrees 2θ at 10.8, 13.4, and 18.4.

2. The crystalline form of claim 1, characterized by a powder X-ray diffraction pattern having characteristic peaks in degrees 2θ at 10.8, 13.4, and 18.4, 20.8, 21.0, and 25.2.

3. The crystalline form of claim 1, characterized by a powder X-ray diffraction pattern having characteristic peaks in degrees 2θ at 10.8, 13.4, 16.6, 18.4, 18.6, 20.8, 21.0, 21.6, 25.2, 25.6, 29.7, and 29.9.

4. The crystalline form of claim 1, comprising the powder X-ray diffraction pattern shown in FIG. 1.

5. The crystalline form of claim 1, wherein the powder X-ray diffraction pattern was obtained using Cu Kα radiation.

6. The crystalline form of claim 1, characterized by a differential scanning calorimetry (DSC) profile having a characteristic endothermic peak at about 128° C.

7. The crystalline form of claim 1, wherein the 3-hydroxy-2-(5-isobutyryl-1-oxo-2,5-diazaspiro[3.4]octan-2-yl)butanamide, monohydrate, has a space group of $P2_12_12_1$.

\* \* \* \* \*